(12) United States Patent
Gaynor et al.

(10) Patent No.: US 9,296,535 B2
(45) Date of Patent: **\*Mar. 29, 2016**

(54) FLEXIBLE MULTI-PANEL STERILIZATION ASSEMBLY WITH MASS BALANCING SIDE TABS

(71) Applicant: AVENT, INC., Alpharetta, GA (US)

(72) Inventors: Melissa R. Gaynor, Roswell, GA (US); Eric T. Bricker, Roswell, GA (US); Jeffrey J. Farmer, Roswell, GA (US); Mark T. Pamperin, Cumming, GA (US); Corinna Schwarz, Roswell, GA (US); Catherine J. Turnbow, Cumming, GA (US)

(73) Assignee: Avent, Inc., Alpharetta, GA (US)

( \* ) Notice: Subject to any disclaimer, the term of this patent is extended or adjusted under 35 U.S.C. 154(b) by 233 days.

This patent is subject to a terminal disclaimer.

(21) Appl. No.: 13/629,521

(22) Filed: Sep. 27, 2012

(65) Prior Publication Data

US 2013/0092724 A1      Apr. 18, 2013

Related U.S. Application Data

(60) Provisional application No. 61/541,655, filed on Sep. 30, 2011, provisional application No. 61/677,616, filed on Jul. 31, 2012.

(51) Int. Cl.
*B65D 65/26* (2006.01)
*B65D 27/00* (2006.01)
(Continued)

(52) U.S. Cl.
CPC .............. *B65D 65/22* (2013.01); *A61B 19/02* (2013.01); *A61L 2/26* (2013.01); *A61B 2019/0201* (2013.01); *A61B 2019/0219* (2013.01)

(58) Field of Classification Search
CPC ......................................................... B65D 65/22
USPC .......................... 229/87.05, 92.5, 87.01, 92.7
See application file for complete search history.

(56) References Cited

U.S. PATENT DOCUMENTS 789,957 A  \*  5/1905  Bassinger .................... 229/92.7
1,198,676 A     9/1916  Snyder
(Continued)

FOREIGN PATENT DOCUMENTS

GB           2274823 A     8/1994
WO     WO 2012/104811 A1   8/2012

OTHER PUBLICATIONS

Co-pending U.S. Appl. No. 13/629,488, filed Sep. 27, 2012, by Gaynor et al. for "Flexible Multi-Panel Sterilization Assembly With Side Tabs."

*Primary Examiner* — Jes F Pascua
*Assistant Examiner* — Derek Battisti
(74) *Attorney, Agent, or Firm* — Dority & Manning, P.A.

(57) ABSTRACT

A multi-panel sterilization assembly having a barrier panel, side tabs with grip portions for folding/unfolding the barrier panel, and a fold protection panel. The barrier panel has first and second opposed ends, a first edge and a third edge, each such edge generally perpendicular to the first end, and a second edge that is opposite the first end. A longitudinal axis extends from the first end to the second end bisecting the assembly into a first assembly portion and a second assembly portion. The first assembly portion extends from the longitudinal axis to the first edge and side tab defining a first center of mass, and the second assembly portion extends from the longitudinal axis to the third edge and side tab defining a second center of mass, such that each center of mass is closer to its respective edge than to the longitudinal axis.

19 Claims, 30 Drawing Sheets

(51) Int. Cl.
 B65D 75/00 (2006.01)
 B65D 65/22 (2006.01)
 A61B 19/02 (2006.01)
 A61L 2/26 (2006.01)

(56) References Cited

U.S. PATENT DOCUMENTS

| | | | |
|---|---|---|---|
| 1,565,178 A * | 12/1925 | Mackovjak | 229/92.7 |
| 1,720,721 A | 7/1929 | Frank | |
| 2,224,607 A * | 12/1940 | Petzold | 229/72 |
| 3,073,436 A * | 1/1963 | Burt | 229/203 |
| 3,225,920 A * | 12/1965 | Reilly | 206/299 |
| 3,261,538 A * | 7/1966 | Jones | B65D 75/5838 206/459.5 |
| 3,409,121 A | 11/1968 | Michael | |
| 3,419,136 A * | 12/1968 | Pratt | 206/361 |
| 3,680,772 A * | 8/1972 | Hoover | 229/79 |
| 3,746,152 A | 7/1973 | Allen | |
| 3,780,857 A * | 12/1973 | Rosano et al. | 206/370 |
| 3,783,862 A * | 1/1974 | Schrading et al. | 128/855 |
| 4,099,614 A * | 7/1978 | Heissenberger | 206/299 |
| 4,342,392 A * | 8/1982 | Cox | 206/438 |
| 4,515,270 A | 5/1985 | Alvarado | |
| 5,244,718 A * | 9/1993 | Taylor et al. | 442/208 |
| 5,635,134 A | 6/1997 | Bourne et al. | |
| 6,045,035 A | 4/2000 | Murakami et al. | |
| 6,159,067 A | 12/2000 | Willis et al. | |
| 6,578,348 B1 * | 6/2003 | Banks | 53/425 |
| 7,172,107 B2 | 2/2007 | Kranz | |
| 7,726,547 B2 | 6/2010 | Tachikawa et al. | |
| 7,922,983 B2 * | 4/2011 | Prokash et al. | 422/294 |
| 8,261,963 B2 | 9/2012 | Gaynor et al. | |
| 2001/0036519 A1 | 11/2001 | Bayer | |
| 2005/0163654 A1 | 7/2005 | Stecklein et al. | |
| 2006/0144911 A1 | 7/2006 | Sierra-Gomez et al. | |
| 2011/0033137 A1 | 2/2011 | Gaynor et al. | |
| 2013/0081355 A1 * | 4/2013 | Gaynor et al. | 53/167 |

* cited by examiner

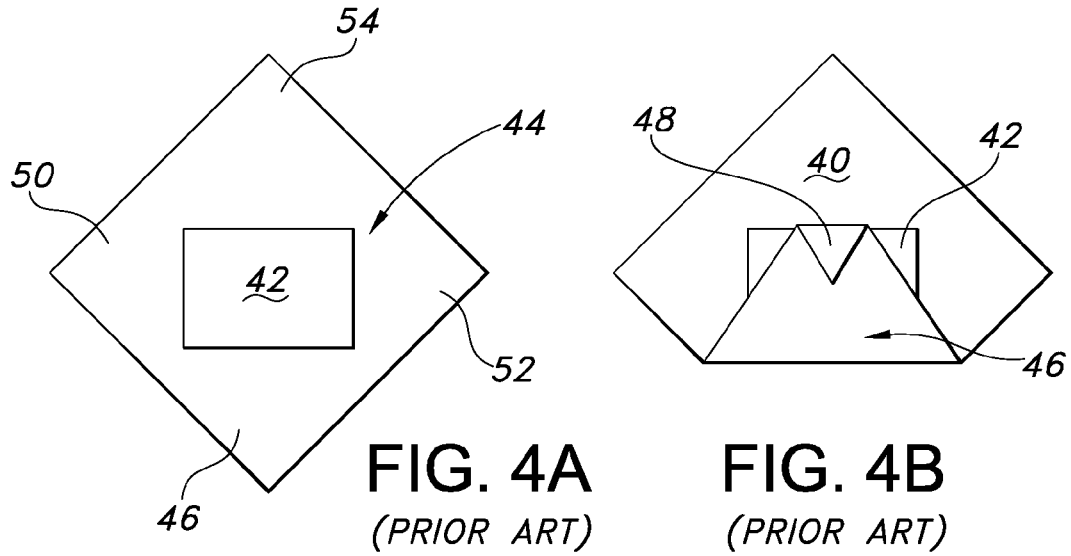
FIG. 4A
*(PRIOR ART)*
FIG. 4B
*(PRIOR ART)*
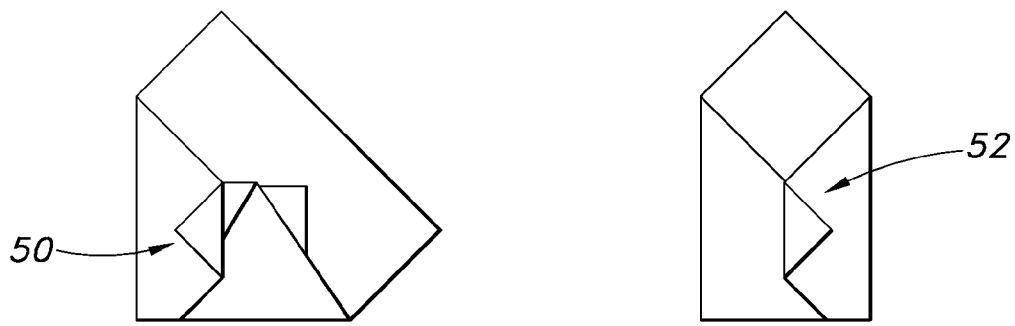
FIG. 4C
*(PRIOR ART)*
FIG. 4D
*(PRIOR ART)*
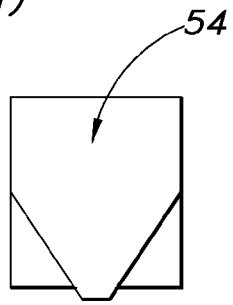
FIG. 4E
*(PRIOR ART)*

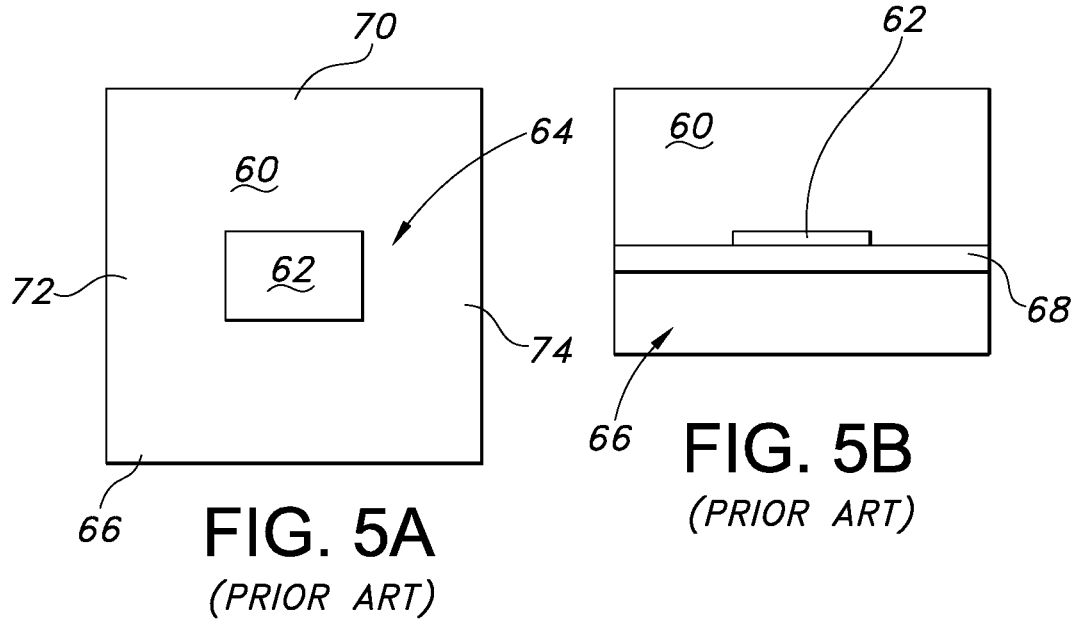
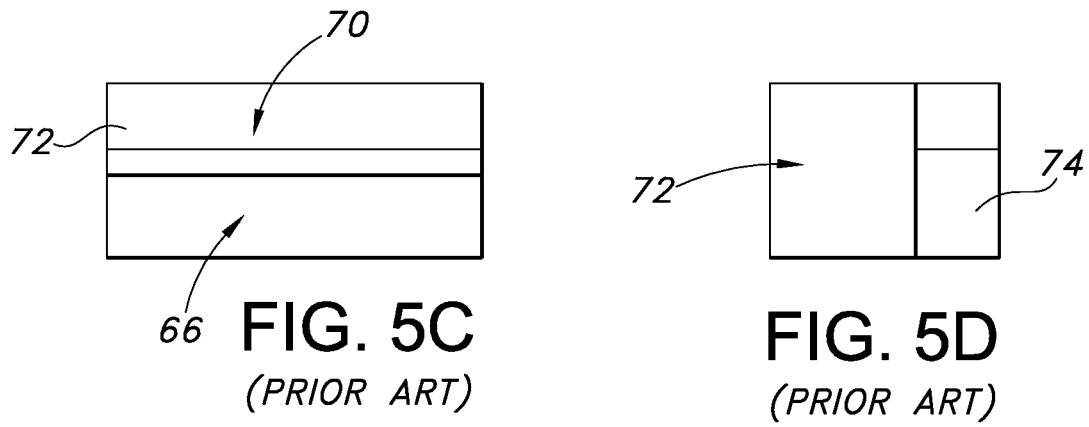
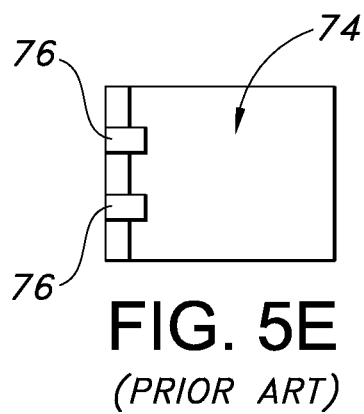

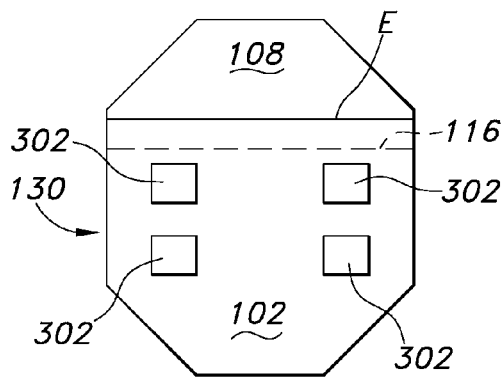
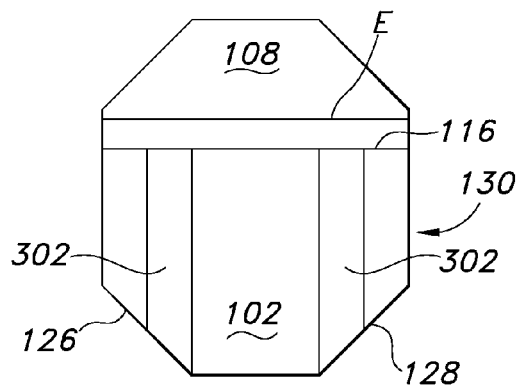
FIG. 11A    FIG. 11B
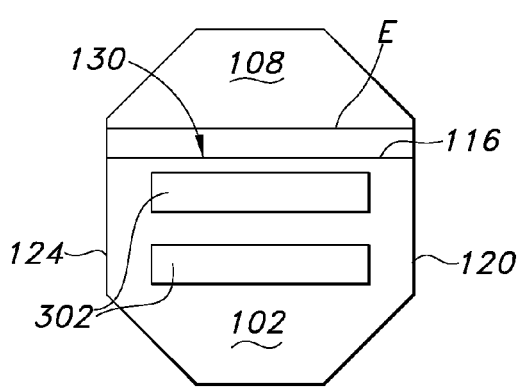
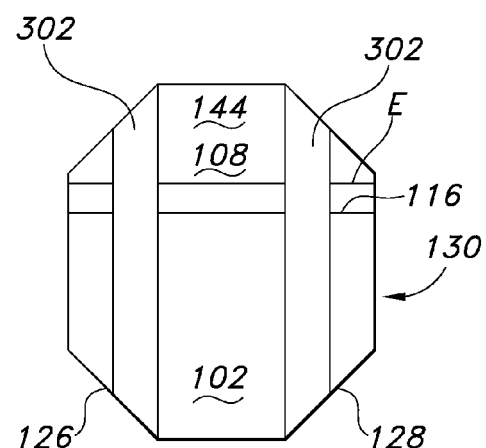
FIG. 11C    FIG. 11D
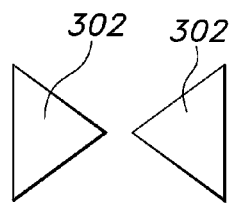
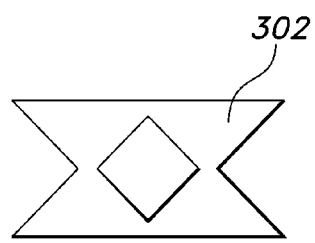
FIG. 12A    FIG. 12B

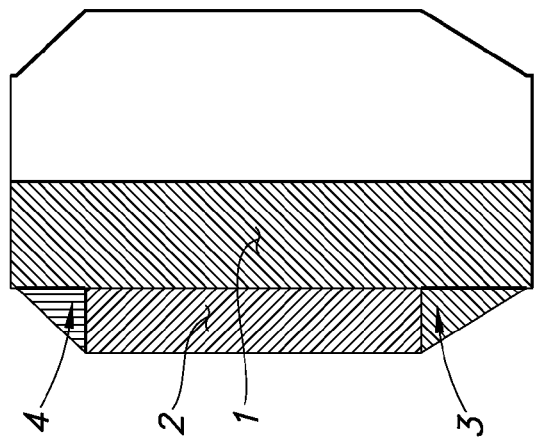
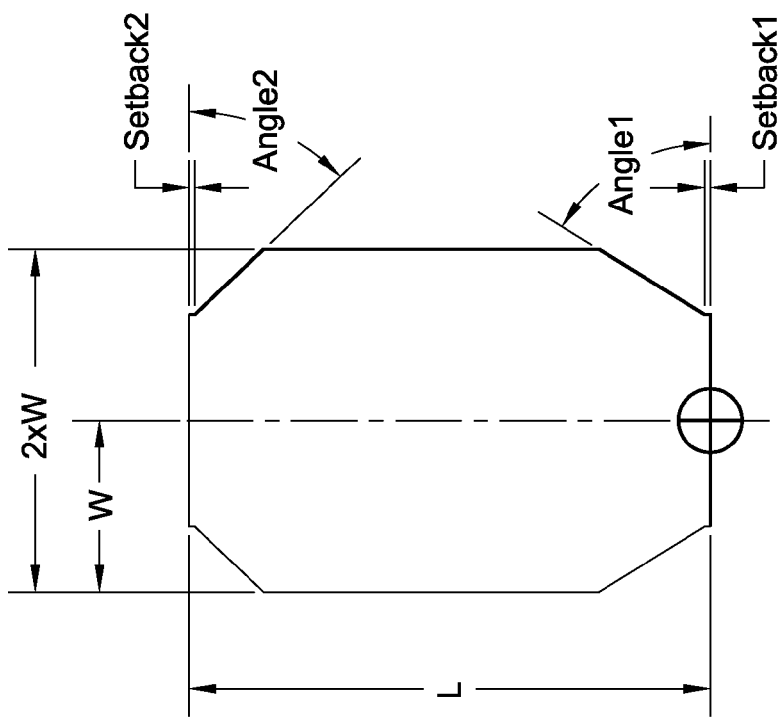
FIG. 15B
FIG. 15A

FLEXIBLE MULTI-PANEL STERILIZATION ASSEMBLY WITH MASS BALANCING SIDE TABS

This application claims the benefit of priority from U.S. Provisional Application No. 61/541,655 filed on Sep. 30, 2011 and from U.S. Provisional Application No. 61/677,616 filed on Jul. 31, 2012.

FIELD OF THE INVENTION

The present invention relates in general to disposable wraps used to contain content to be sterilized and store that content aseptically until use.

BACKGROUND OF THE INVENTION

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are wrapped in suitable barrier fabric and then sterilized and stored for subsequent use. Such fabric is typically cut into predetermined rectangular shapes and sold as sterilization wraps.

Traditional wrapping of a sterilization tray or similar articles in a conventional disposable sterilization wrap often involves a large amount of redundant material as excess corners and overlapping plies are gathered, folded, and secured together at the top of the sterilization tray.

Conventional disposable sterilization wrap is a flat, featureless sheet of material that may occasionally contain one or more additional layers of material for strength or absorbency. This flat, featureless configuration provides no information or guidance to a person wrapping an article with the flat sheet of material on how to wrap an article.

Conventional disposable sterilization wrap is frequently made of inexpensive, relatively impermeable material such as, for example, paper and the like. The properties of these materials have generally influenced folding techniques and wrapping configurations to ensure the sterility of the wrapped tray or article.

For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. Patent Application Publication No. 2001/0036519 by Robert T. Bayer discloses a two ply sterilization wrap that is formed of a single sheet of sterilization wrap material which is folded to form two similarly sized, superposed panels that are bonded to each other. As yet another example, U.S. Patent Application Publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

Generally speaking, in these and other examples, articles or content to be sterilized, e.g. trays with surgical instruments and/or supplies, singular instruments, absorbents, basins, etc., are centered on large sheets of conventional disposable sterilization wrap and the uncovered portions of the sterilization wrap are folded around the articles to create large expanses of overlapping materials using one or two standard fold techniques. These conventional techniques and the resulting fold configurations require manipulating excess amount of materials during the wrapping and unwrapping process. Additionally the use of these fold techniques provide for touch points or grip locations of the sterilization wrap material for subsequent unfolding. It takes experience and a certain level of skill to wrap a tray or similar article quickly and reliably. Because of scheduling and cost pressures, medical equipment needed for some procedures may require immediate turnaround and must be processed, sterilized and available for use within hours of its use in a previous procedure. As turnaround times continue to compress, there is a corresponding increase in the need to wrap an article even more quickly while ensuring the integrity of the fold configuration of the sterilization wrap (the wrapping) around the sterilized article. There is also a corresponding increase in the need to quickly unwrap a sterilized article while preserving the sterility of the sterilized article.

Large sheets of conventional disposable sterilization wrap in combination with standard fold techniques do provide an advantage during unwrapping of an item after sterilization, particularly when the sterilization wrap is formed from a material that may stiffen or take a set during the sterilization process. For example, when sterilization wrap composed of nonwoven material made from certain thermoplastic polymers are used in an extended or enhanced steam or heat sterilization process, the nonwoven material may take on a set or an "imprint" of the shape of the wrapped article or tray. During unwrapping of the article or tray, imprinted creases, folds or other deformations must be overcome during unfolding so the sterilization wrap can lay flat. If the sterilization wrap does not lie flat, it is possible for unfolded portions of the sterilization wrap to fold back up towards the sterilized article or tray while other portions of the wrap are being unfolded. This would compromise the sterility of the article. The large expanses of material and the rectangular shape of the sheets in combination with standard folding techniques generally keep the sterilization wrap from folding back onto itself during unwrapping. However, the use of large sheets of conventional disposable sterilization wrap with standard fold techniques provides large expanses of overlapping materials and multiple folds which require using and manipulating excessive amounts of material during the wrapping and unwrapping process, adding difficulty that slows the wrapping and unwrapping process, and creating waste.

When large sheets of conventional sterilization wrap are reduced in size, the reduction in material amplifies the problem of unfolded portions of the sterilization wrap folding back up towards the sterilized article or tray while other portions of the wrap are being unfolded. Moreover, this problem can also be amplified by altering the geometry of the sheet of sterilization wrap so the sheet is less square (e.g., in order to reduce the amount of material in the sheet). Regardless of the size of conventional sterilization wrap, during unwrapping the sterilization wrap material must be grasped to unfold the overlapping expanses.

Accordingly, there is an unmet need for an easy to use assembly, package or system that reduces the amount of sterilization wrap material needed for the sterile processing of an instrument tray or article and eliminates the need to grasp the sterilization wrap material to unfold wrap. There is also an unmet need for an easy to use assembly, package or system that reduces the amount of sterilization fabric and simplifies the task of unwrapping a sterilized instrument tray or article while reducing or avoiding the likelihood that the sterilization fabric will fold back onto itself during unwrapping. The need is particularly apparent for an assembly, package or system that reduces the amount of sterilization fabric, that can be used in an extended or enhanced steam or heat sterilization process, and that simplifies the task of unwrapping a sterilized instrument tray or article while reducing or avoiding the likelihood that the sterilization fabric will fold back onto itself during unwrapping.

BRIEF SUMMARY OF THE INVENTION

The problems described above are addressed by the present invention which encompasses a flexible multi-panel sterilization assembly. The flexible multi-panel sterilization assembly (sterilization assembly) includes a barrier panel composed of a permeable sheet material having barrier properties, side tabs that include grip portions for folding or unfolding the barrier panel; and a fold protection panel.

The barrier panel includes: a first surface and a second opposing surface; a first end and a second end opposite the first end; at least a first edge and a third edge, each such edge being generally perpendicular to the first end; and a second edge that is away from or generally opposite the first end.

The fold protection panel is in juxtaposed communication with the barrier panel. That is, the fold protection panel desirably extends from the barrier panel. The fold protection panel includes: a proximal end generally adjacent, adjoining, or extending from the first end of the barrier panel; a distal end generally opposite the proximal end; and at least a first edge portion and a second edge portion extending from the proximal end toward the distal end.

The sterilization assembly has a longitudinal axis extending from at least the first end to the second end of the barrier panel such that it bisects the assembly into a first portion and a second substantially equal portion. That is, the longitudinal axis represents a bisecting axis of symmetry, and each portion has a respective center of mass. According to the invention, the center of mass of the first portion is closer to the first edge than to the longitudinal axis and the center of mass of the second portion is closer to the third edge than to the longitudinal axis.

Generally speaking, the side tabs are located between the first end and a midpoint of the barrier panel and at or near (e.g., adjacent) the first and third edges of the barrier panel and the side tabs are selected and positioned to shift the respective centers of mass in a manner that ensures aseptic opening after the assembly is wrapped around contents to be sterilized. That is, through proper selection and positioning, the side tabs prevent the first and third edges of the barrier panel from folding back on itself during unfolding of the barrier panel, particularly after extended steam or heat sterilization.

According to the invention, the side tabs are selected and positioned to provide weight beyond the side edges of the assembly and also towards the first end of the barrier panel that is adjacent the proximal end of the fold protection panel. The appropriate weight and positioning on the side tabs shift the centers of mass for each combined portion (that is, the first portion of the assembly plus its side tab and the second portion plus its side tab) by at least a minimal distance away from the longitudinal axis and at least a minimal distance in the direction towards the first end. Proper positioning of the side tabs adjacent the barrier panels have a part of each side tab within the upper boundary of the content receiving region. Embodiments that position a side tab along the first and third edges so that a part of each side tab is at or above the pre-determined fold line or reference line is necessary for proper positioning. Additionally, an attached side tab that adjoins the content receiving region and with a weight of only 0.028 ounce has been found to be insufficient to shift the center of mass of the first or second portion to ensure aseptic opening of the assembly after wrapping and sterilizing; the weight contribution of the side tab, inclusive of any panel attachment means, needs to be greater than 0.028 ounce. That is, the weight contribution of the side tab, inclusive of any panel attachment means, may range from just above 0.028 ounce up to several ounces. While heavier weights may be contemplated, they may not provide particular advantage to offset the cost and complexity of provided the additional weight.

The multi-panel sterilization assembly may optionally include a panel attachment means to join the side tabs to each other or to a portion of the content covering region after the barrier panel has been folded at or near its midpoint such that its second end is brought towards its first end. The panel attachment means may be adhesive tape, double-sided adhesive tape, cleavable release tapes, layered release tapes, cohesive materials, hooks of hook and loop fastening systems, mechanical fastening systems including, but not limited to, snaps, clips, magnets, catches, slots and tabs, interlocking arrays and combinations thereof.

According to an aspect of the invention, the barrier panel further may further include indicia between the first edge and the third edge of the barrier panel. The indicia (which may be referred to as a "pre-determined fold line" or a "reference line") is desirably aligned generally parallel to the extremity of the first end of the barrier panel and is located away from the extremity in the direction toward the midpoint of the barrier panel. The indicia define an upper boundary of the content receiving region. The side tabs are positioned along the barrier panel first and third edges so that they desirably span to both sides of the pre-determined fold line. The side tab edge that is closest to the first end of the barrier panel can be aligned with this first end but does not extend farther away from the pre-determined fold line and beyond this first end.

Barrier panel attachment means may be used to join the side tabs to each other or to a portion of the content covering region after the barrier panel has been folded at or near its midpoint such that its second end is brought near its first end. At least one barrier panel attachment means is desirably located on a portion of the side tab within the upper boundary of the content receiving region which may desirably by defined by the indicia.

In an aspect of the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments. The permeability of the sheet material of the barrier panel (or the barrier panel itself) may range from 25 to about 500 cubic feet per minute (CFM) as characterized in terms of Frazier permeability. For example, the permeability of the sheet material barrier panel may range from 25 to about 400 cubic feet per minute. As yet another example, the permeability of the sheet material of the barrier panel may range from 25 to about 300 cubic feet per minute. Alternatively and/or additionally, the permeability of the barrier panel may range from about 10 to about 30 cubic feet per minute when the barrier panel is composed of multiple plies or layers of a nonwoven laminate material.

The sterilization assembly may also include at least one pull tab. The pull tab provides a feature that aids the user to unwrap the sterilized article within the folded flexible multi-panel sterilization assembly aseptically. That is, during the unwrapping of an article, a person may use the pull tab to avoid reaching over the sterile field generally presented by unwrapping and spreading out the sterile content-contacting surface of the barrier panel. The pull tab may be unitary with the barrier panel or it may be attached to the barrier panel. Desirably, the pull tab is located at or near the second end of the barrier panel forming the content covering region and may desirably be located on the second surface of the barrier panel. The pull tab may be formed of the same material as the barrier panel, one or more different materials, or even the same piece of material as the barrier panel. Desirably, the pull tab or pull tabs provide for spaced apart pull locations. In an aspect of the invention, panel attachment means may attach to the content covering region between the spaced apart pull locations. For example, panel attachment means located on the side tabs may be configured to attach to the content covering region between the spaced apart pull locations.

The sterilization assembly may further include one or more discrete reinforcement elements. These elements are desirably in the content receiving region and define an area for receiving content to be sterilized. The reinforcement element(s) may include one or more layers of materials selected from fibrous webs, impermeable films, permeable or porous films, apertured films, foams, foils and combinations thereof. One or more of these reinforcement elements may extend beyond the second end of the barrier panel to provide a pull tab having spaced apart pull locations.

According to an aspect of the invention, the sterilization assembly may further include indicia or instructions on the sterilization assembly itself to inform the proper folding of the assembly into a package. Alternatively and/or additionally, the sterilization assembly may further include indicia or instructions on the sterilization assembly itself to inform the proper unfolding or unwrapping of the assembly after it has been folded into a package and sterilized.

In an aspect of the invention, there is provided a flexible multi-panel sterilization assembly that includes a barrier panel formed from a sheet of barrier material (e.g., barrier fabric) having at least one panel edge. The barrier panel is configured to be folded into side portions and an end portion to form a package around content to be sterilized. Side tabs generally extend diametrically from a portion of the barrier panel for sequentially positioning the side portions of the barrier panel in a folded configuration around content to be sterilized and provide grips for simultaneously unfolding the folded side portions of the barrier panel. The assembly further includes a fold protection panel extending from the barrier panel. The fold protection panel includes a proximal end generally adjacent the barrier panel and a distal end generally opposite the proximal end such that the distal end of the fold protection panel covers the one or more panel edges of the barrier panel after folding the side and end portions of the barrier panel. The fold protection panel may have barrier properties.

According to the invention, the side tabs may include panel attachment means. These may be selected from adhesive tape, double-sided adhesive tape, cohesive materials, hook and loop fastening systems, mechanical fastening systems, snaps, clips, magnets, catches, slots and tabs, and combinations thereof.

In an aspect of the invention, the sterilization assembly may further include a pull tab feature that comprises at least one pull tab and provides spaced apart pull locations. Panel attachment means that may be located on the side tabs may desirably be configured to attach to the barrier panel between the spaced apart pull locations. The sterilization assembly may further include discrete reinforcement elements on the barrier panel.

According to an aspect of the invention, the sterilization assembly may have a longitudinal axis extending from at least the first end to the second end of the barrier panel such that it bisects the assembly into a first portion and a second substantially equal portion whereby the center of mass of the first portion is closer to the first edge than to the longitudinal axis and the center of mass of the second portion is closer to the third edge than to the longitudinal axis.

The sterilization assembly has a longitudinal axis extending from at least the first end to the second end of the barrier panel such that it bisects the assembly into a first portion and a second substantially equal portion, wherein each portion has a common boundary along the longitudinal axis and the first portion has least a first portion edge that is generally opposite the longitudinal axis and the second portion has at least a second portion edge that is also generally opposite the longitudinal axis. That is, the longitudinal axis represents a bisecting axis of symmetry, and each portion has a respective center of mass located between the longitudinal axis and its respective portion edges. According to the invention, the center of mass of the first portion is closer to the first portion edge than to the longitudinal axis and the center of mass of the second portion is closer to the second portion edge than to the longitudinal axis.

Generally speaking, the side tabs are located on each portion of the barrier panel and at or near (e.g., adjacent) the first portion edge and second portion edge and are selected and positioned to shift the respective centers of mass in a manner that ensures aseptic opening after the assembly is wrapped around contents to be sterilized. That is, through proper selection and positioning, the side tabs prevent the first portion edge and second portion edges from folding back on itself during unfolding of the barrier panel, particularly after extended steam or heat sterilization.

According to the invention, the side tabs are selected and positioned to provide weight beyond the side edges of the assembly and also towards the first end of the barrier panel that is adjacent the proximal end of the fold protection panel. The appropriate weight and positioning on the side tabs shift the centers of mass for each combined portion (that is, the first portion of the assembly plus its side tab and the second portion plus its side tab) from the centers of mass without the side tabs by at least a minimal distance away from the longitudinal axis and at least a minimal distance in the direction towards the first end. The shift in each respective center of mass for the corresponding combined portion results from the contribution of the side tab. Proper positioning of the side tabs adjacent the barrier panels have a part of each side tab within the upper boundary of the content receiving region.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Invention with reference to the accompanying drawing figures, in which like reference numerals denote similar structure and refer to like elements throughout, and in which:

FIGS. 4A to 4E are illustrations of a sequence of folding an exemplary prior art sterilization wrap system using a conventional envelope fold.

FIGS. 5A to 5E are illustrations of a sequence of folding an exemplary prior art sterilization wrap system using a conventional square fold.

FIG. 10D shows the assembly including side and pull tabs unfolded and flat.

FIGS. 11A to 11D are illustrations of exemplary flexible multi-panel sterilization assemblies showing exemplary reinforcing elements.

FIGS. 12A to 12B are illustrations of exemplary reinforcing elements.

FIGS. 15A and 15B are illustrations of a top view showing regions and areas of a portion of an exemplary assembly for determining center of mass values.

DEFINITIONS

Figure 1:
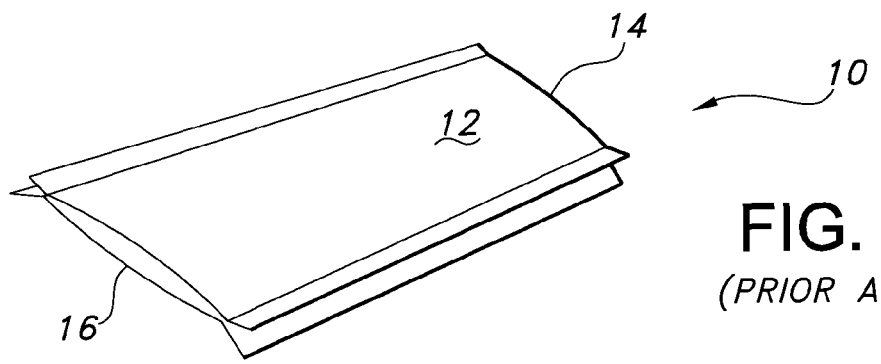
FIG. 1 is an illustration of an exemplary prior art sterilization wrap system.

As used herein, the term "basis weight" refers to the weight of a material per specified unit of surface area. This measure is usually associated with relatively thin, flat, sheet-like materials such as, for example, fabrics, films, papers, webs and the like. Basis weights of the materials discussed herein were determined essentially in accordance with Method 5041 of Federal Test Method Standard No. 191A. Basis weight may also be measured using test procedure ASTM D 3776-96 or TAPPI Test Method T-220. Basis weight is expressed in units of weight per unit of area (e.g., grams per square meter or ounces per square yard). These units may be abbreviated as "gsm" or "osy", respectively.

As use herein, the term "center of mass" refers to the weighted average location of all the mass in a body. With reference to the sterilization assembly of the present invention, the center of mass refers to that point in a flat, unfolded assembly at which the whole mass may be considered as concentrated. A flat, unfolded assembly refers to an assembly with the barrier panel and the fold protection panel fully unfolded and the side tabs 400 fully extended outward—away from the edges and center of the assembly as illustrated at, for example FIG. 8C or FIG. 10D. It is noted that that pull tab(s) 300 are excluded from consideration in determining the center of mass because a pull tab 300 is grasped by a user last—after releasing the side tabs 400). Since the assembly in the flat, unfolded state is intended to have at least one axis of symmetry, the point of the center of mass of the assembly is: along the longitudinal axis that bisects the assembly into the first and second substantially equal portions; between the second end of the barrier panel and the distal end of the fold protection panel. In terms of the center of mass for each first and second portion of the assembly, the respective mass of the portion is half that for the whole assembly and the point at which this mass may be considered concentrated is a distance away from the bisecting longitudinal axis. One way to determine the center of mass for each first or second portion is to subdivide the shape of the portion into simpler shapes (e.g. rectangles, triangles), obtain their respective mass and center of mass, then calculate the center of mass for the whole portion as the average of their respective center of mass position weighed by their respective masses (also referred to as the weighted average of the centers of mass). A conventional mathematical representation of such weighed averaging of centers of mass for an assembly is:

$$\vec{r}_{cm} = \frac{\sum \vec{r}_i m_i}{m_{total}}$$

where $\vec{r}_{cm}$ is the center of mass for the assembly, $\vec{r}_i$ represents the center of mass for each subdivided area shape, and $m_i$ is the mass for each subdivided area shape. Also, a conventional expression of $\vec{r}$ is via x, y, and z coordinates relative to some defined reference origin. For relatively flat and thin assemblies, such as those of the invention, the z coordinate is very small and changes due to the additional or omission of a side tab per the invention is essentially negligible, thus $\vec{r}_{cm}$ and $\vec{r}_i$ can be accurately represented by x and y coordinates relative to a designated reference origin.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "machine direction" or MD means the length of a material or fabric in the direction in which it is produced. For example, the machine direction of a nonwoven web may be the planar dimension of the nonwoven web which is in the direction of travel of the forming surface onto which fibers and/or filaments are deposited during formation of the web. The term "cross machine direction" or CD means the direction generally perpendicular to the MD (which would be the width of fabric that has a machine direction along its length). For example, the cross-machine direction of a nonwoven web may be the planar dimension of the nonwoven web which is in the direction that is perpendicular to direction of travel of the forming surface onto which fibers and/or filaments are deposited during formation of the web.

As used herein, the term "meltblown" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, these fibers are carried by the high-velocity gas stream and are deposited on a collecting surface to form a web or fabric of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, the terms "multi-panel sterilization assembly" or "sterilization assembly" or "assembly" refer to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven" refers to a web or fabric that has a structure of individual fibers or filaments which are interlaid, but not in an identifiable repeating manner. Nonwovens have been, in the past, formed by a variety of processes known to those skilled in the art such as, for example, meltblowing, spunbonding and bonded carded web processes.

As used herein "point bonding" means bonding one or more layers of fabric at a plurality of discrete bond points. For example, thermal point bonding generally involves passing a fabric or web of fibers to be bonded between a heated roll assembly such as, for example, a heated calender roll and an anvil roll. The calender roll is usually patterned in some way so that the entire fabric is not bonded across its entire surface, and the anvil roll is usually smooth. As a result, various patterns for calender rolls have been developed for functional and/or aesthetic reasons. One example of a pattern has points and is the Hansen Pennings or "H&P" pattern with about a 30% bond area with about 200 bonds/square inch (31 bonds/square cm) as taught in U.S. Pat. No. 3,855,046 to Hansen and Pennings. Another example is shown in U.S. Design Pat. No. 239,566 to Vogt. Typically, the percent bonding area varies from around 5% to around 30% of the area of the fabric laminate web. Spot bonding holds the laminate layers together as well as imparts integrity to each individual layer by bonding filaments and/or fibers within each layer without destroying the breathability or hand of the fabric.

As used herein, the term "spunbonded fabric" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbond nonwoven fabrics is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, "ultrasonic bonding" means a process performed, for example, by passing the fabric between a sonic horn and anvil roll as illustrated in U.S. Pat. No. 4,374,888 to Bornslaeger, the entire contents of which is incorporated herein by reference.

DETAILED DESCRIPTION OF INVENTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIG. 1, there is shown an exemplary conventional disposable sterilization wrap 10 having a multiple-ply configuration which is formed by joining one or more sheets 12 of sterilization wrap together to form two similarly sized, superposed panels 14 and 16 that allow convenient dual wrapping of an article. While one sheet may be folded back on itself to provide the multiple-ply configuration, two separate sheets are more typically used.

Figure 2:
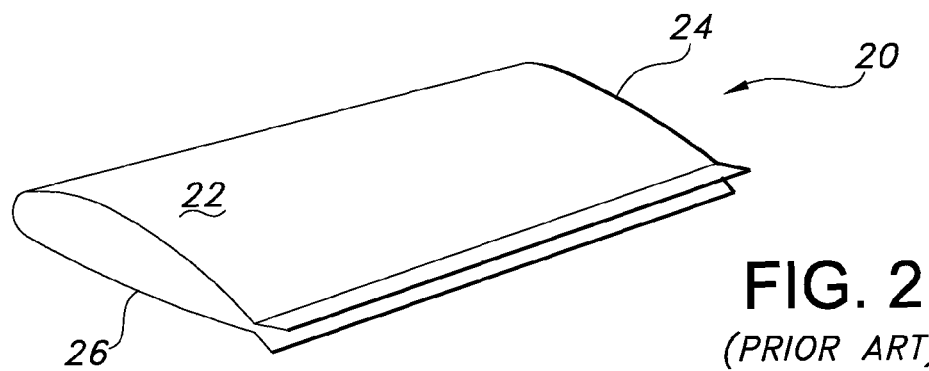
FIG. 2 is an illustration of an exemplary prior art sterilization wrap system.

FIG. 2 is an illustration of an exemplary conventional disposable sterilization wrap 20 as generally disclosed in U.S. Patent Application Publication No. 2001/0036519 by Robert T. Bayer. The conventional disposable sterilization wrap 20 is a two ply sterilization wrap formed of a single sheet 22 of sterilization wrap material which is folded to form two similarly sized, superposed panels 24 and 26 that are bonded to each other.

Figure 3:
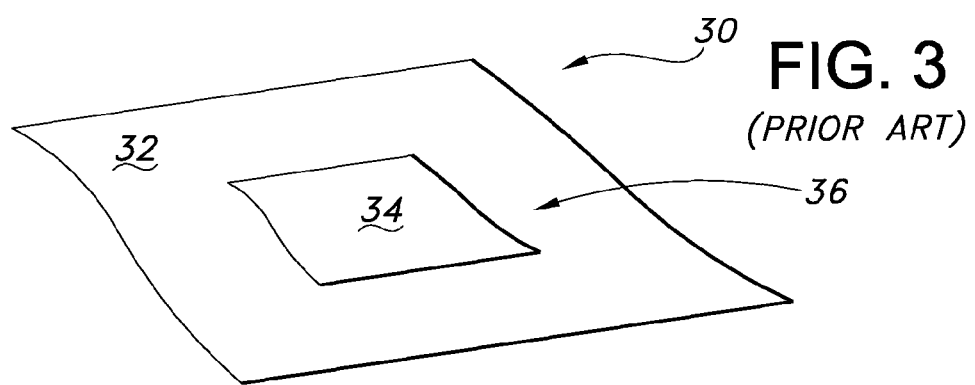
FIG. 3 is an illustration of an exemplary prior art sterilization wrap system.

FIG. 3 is an illustration of yet another example of a conventional disposable sterilization wrap 30 as generally disclosed in U.S. Patent Application Publication No. 2005/0163654 by Stecklein, et al. The conventional disposable sterilization wrap 30 has a first main panel 32 and a second panel 34 that is much smaller than the main panel 32. The second panel 34 is superposed and bonded to the central portion 36 of the main panel 32 to reinforce the main panel 32 and/or provide additional absorbency.

Generally speaking, in these and other examples, large sheets of conventional disposable sterilization wrap are typically used to create large expanses of overlapping materials using one or two standard fold techniques. These standard techniques and the resulting fold configurations require manipulating excess amount of materials during the wrapping and unwrapping process. It takes experience and a minimum level of skill to reliably wrap a tray or similar article quickly.

FIGS. 4A through 4E illustrate an exemplary sequence of steps in wrapping an article utilizing a conventional sterilization wrap. As illustrated in FIG. 4A, a square or generally rectangular wrap 40 is spread out flat and an article 42 to be wrapped is placed in a central region 44 of the wrap 40 in a generally diagonal relationship to the orientation of the wrap 40 in a pattern conventionally referred to as an envelope fold. Referring to FIG. 4B, a first end 46 of the wrap is folded up at the base of the article 42 and brought over the article 42. Generally speaking, the sterilization wrap must be sufficiently large in area to provide enough material to substantially cover the article in the initial fold. The first folded end 46 is back-folded to create a small tail 48. This sequence is time consuming, requires the worker to pay careful attention to the size of the tail, and is generally repeated for each of the remaining second end 50 and the third end 52. Again, the sterilization wrap must be sufficiently sized in area to provide enough material for the second end 50 and the third end 52 to substantially overlap such that the entire or substantially the entire second end 50 is covered by the third end 52. The fourth end 54 is folded over and taped to form a wrapped package.

FIGS. 5A through 5E illustrate another exemplary sequence of steps in wrapping an article utilizing a conventional sterilization wrap. As illustrated in FIG. 5A, a square or generally rectangular wrap 60 is spread out flat and an article 62 to be wrapped is placed in a central region 64 of the wrap 60 in a generally parallel relationship to the orientation of the wrap 60 in a pattern conventionally referred to as a square fold. Referring to FIG. 5B, a bottom end 66 of the wrap is folded up at the base of the article 62 and brought over the article 62. Generally speaking, the sterilization wrap must be sufficiently large in area to provide enough material to substantially cover the article in the initial fold. The folded bottom end 66 is back-folded to create a folded edge 68. This sequence is generally repeated for the remaining top end 70 and the left side end 72. Again, the sterilization wrap must be sufficiently sized in area to provide enough material for the top end 70 and the left side end 72 to substantially overlap such that the entire or substantially the entire bottom end 70 is covered by the left side end 72. The right side end 74 is folded over and taped 76 to form a wrapped package.

A typical sterilization tray with the dimensions of 10 inches (25.4 cm) by 20 inches (50.8 cm) by 5 inches tall (12.7 cm) typically requires a square piece of sterilization fabric having each side measuring 45 inches for wrapping and sterile processing. This large size piece is needed so that the corner of the fabric can be folded all the way across the top of the tray with some additional excess material so that the preparer of the tray feels confident that the contents are covered and that the piece of fabric will stay down and not spring back. Using a 45 inch square piece of fabric means that 2025 square inches of material (approximately 13,064 square centimeters) is being used to enclose a tray with a surface area of just 700 square inches (approximately 4,516 square centimeters). In other words, this traditional method requires almost three square inches of material to cover every square inch of a tray of surgical instruments.

The present invention encompasses a multi-panel sterilization assembly which addresses the problems generally described above and which also addresses a problem discovered when the dimensions of the sterilization fabric are reduced—namely unfolded portions of the sterilization fabric can partially re-fold or fold back on itself during unfolding of other portions of the sterilization assembly. An exemplary multi-panel sterilization assembly 100 is illustrated in FIG. 6.

The multi-panel sterilization assembly includes a barrier panel 102 composed of a permeable sheet material 104 having barrier properties (e.g., a barrier fabric), panel attachment means 106 (not shown in FIG. 6) for securing the barrier panel 102 into a package; and a fold protection panel 108. Generally speaking, the "barrier panel" is the portion of a multi-panel sterilization assembly that is formed from a material that is sufficiently permeable to permit a sterilizing gas to pass through it to effect sterilization and has barrier properties sufficient maintain that content in an aseptic condition after sterilization. A barrier panel should also be sufficiently flexible or conformable to that it is configured to receive and subsequently enfold or enclose content to be sterilized thereby forming a package. Generally speaking, the barrier panel may be a barrier fabric. The "fold protection panel" is the portion of a multi-panel sterilization assembly that is formed from a material covers and protects at least a portion of the folded edges of the barrier panel. The fold protection panel is the last panel or part of the multi-panel sterilization assembly that is folded or wrapped around the package (formed by the barrier panel around content to be sterilized) and is the first part of the multi-panel sterilization assembly that is unfolded or unwrapped. The barrier panel and fold protection panel are each desirably made of a material that provides the required properties yet is so inexpensive that is can be economically disposed of or recycled after a single use. Exemplary materials are polyolefin based nonwoven materials. As noted previously, such inexpensive materials can take a set during heat or steam sterilization such that they have creases or folds that can resist unwrapping and urge portions of the barrier panel back towards a folded position that may compromise aseptic opening of the package.

The barrier panel includes: a first surface 110 and a second opposing surface 112; a first end 114 having an extremity or edge "E"; a second end 118 opposite the first end 114; a first edge 120 that is generally perpendicular to the first end 114; a second edge 122 that is generally opposite the first end 114; and a third edge 124 that is generally perpendicular to the first end 114. The barrier panel 102 may include indicia 116 that may be located towards the extremity "E", but within the first end 114 of the barrier panel. The barrier panel also has a midpoint "M" along the length "L" and extending between the first edge 120 and the third edge 124 or, in some embodiments, additional edges to generally delineate the barrier panel 102 into a content receiving region 130 extending from indicia 116 to the midpoint "M" and a content covering region 132 extending from the midpoint "M" to the second edge 122. Of course, it is contemplated that additional edges may be added or that edges may be curvilinear or may include curvilinear portions.

The indicia 116 may be aligned generally parallel to the edge or extremity "E" of the first end 114 of the barrier panel 102. The indicia 116 is desirably located on the first surface 110 away from the extremity "E" of first end 114 in a direction toward the midpoint "M" of the barrier panel to define an upper boundary of the content receiving region 130. This upper boundary may also be referred to as a "pre-determined fold line". Generally speaking, the indicia 116 (also called the pre-determined fold line) is offset from the extremity "E" of the first end 114 but it is contemplated that the indicia 116 may contact the extremity "E" if the either the indicia or the extremity "E" is non-linear. Just as the extremity "E" defines a boundary or transition between the barrier panel 102 and the fold protection panel 108, the indicia 116 identifies the desired upper boundary of the content receiving region 130 for placing the content to be sterilized within the first end 114 of the barrier panel 102. Placement of an article (content to be sterilized) along the indicia 116 offsets the article from the extremity "E" of the first end 114 in order to provide a sufficient amount of barrier panel to fully surround the article after folding is complete. The indicia 116 may be offset from the boundary or transition defined by extremity "E" between the barrier panel 102 and the fold protection panel 108 by about by about 0.5 inch (~13 mm) to about 10.5 inches (~267 mm). Desirably, the indicia 116 are offset from the boundary or transition boundary or transition defined by extremity "E" by at least 1.5 inches (~38 mm) and may desirably be offset by about 4 inches (~102 mm) or more (e.g., from about 4 inches to about 10.5 inches; from about 4.5 inches to about 9.5 inches; from about 5 inches to about 9 inches). The indicia may be in various forms. The indicia 116 may be in the form of a seam (or seams) such as, for example, a stitched seam, an ultrasonic bond seam, adhesive bond seam, thermo-mechanical bond seam (e.g., a bar seal seam) or combinations thereof, that results from joining layers or plies together to form the barrier panel and the fold protection panel—or the seam(s) may result from joining pieces together if the barrier and fold protection panels are discrete pieces. Alternatively and/or additionally, the indicia 116 may be in the form of printing, or by an imprint such as a thermo-mechanical bond line (e.g., bar seal line) or pattern or other marks, or identified by a visible crease or other suitable distinguishing feature. The indicia 116 may be an intermittent line and it may be provided directly on the barrier panel, it may be provided on only a portion or portions of the barrier panel, or it may be provided on one or more reinforcement elements or other features if such are present.

As noted above, an important feature of the indicia 116 is to help delineate where the content to be wrapped and ultimately sterilized should be placed. That is, content to be wrapped and sterilized should be placed adjacent only one side of the indicia. As discussed subsequently, other features of the present invention signal to a user which side of the indicia is the appropriate side to place content. Yet another feature of the indicia 116 is that it helps defines an additional boundary, reference line, limit, or pre-determined fold line for the user during the wrapping of content to be sterilized. That is, during wrapping, as part of the barrier panel (i.e., the second end 118) is brought over to cover the content to be sterilized, this part of the barrier panel should not be extended substantially across or beyond the indicia 116. In contrast to conventional sterilization wrap systems where the content is placed at the center of the sterilization barrier, the multi-panel sterilization assembly requires placement of the content from the indicia 116 and towards the midpoint "M" rather than near the edge or extremity "E" of the first end 114 of the barrier panel. This is initially counterintuitive for users and is quite different from conventional sterilization wrap systems.

Figure 6A:
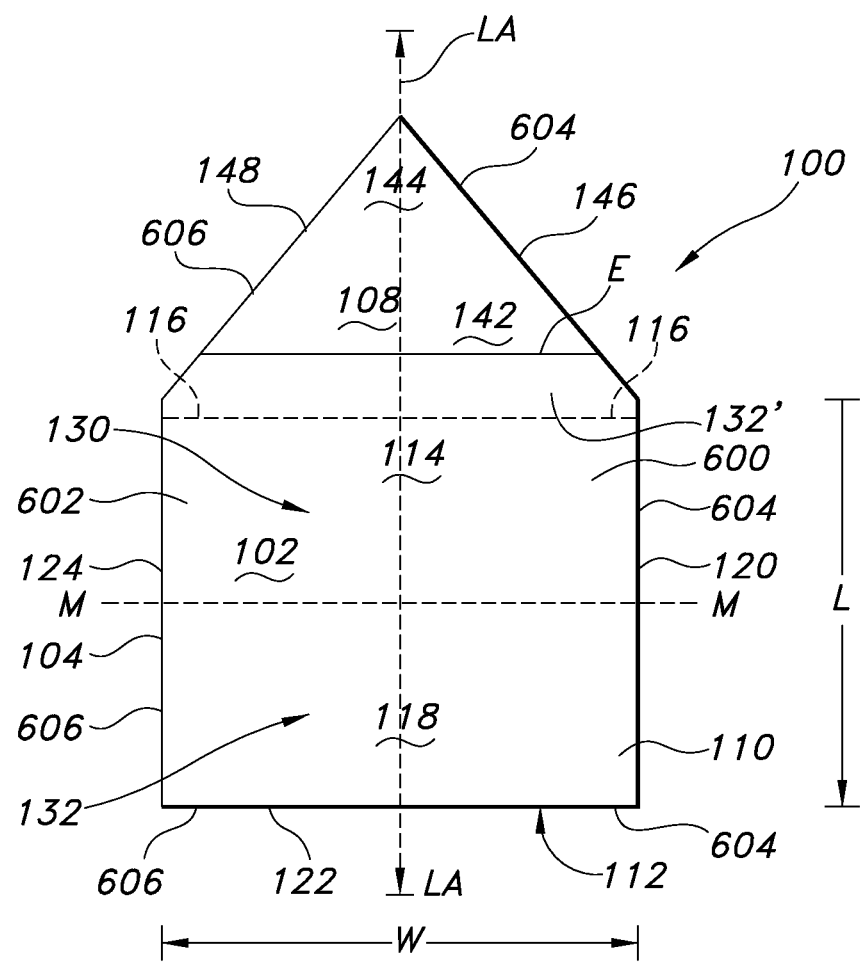
FIG. 6A is a top view illustration of an exemplary flexible multi-panel sterilization assembly including side tabs and pull tabs that are folded over onto the barrier panel (not shown in the top view).
Figure 6B:
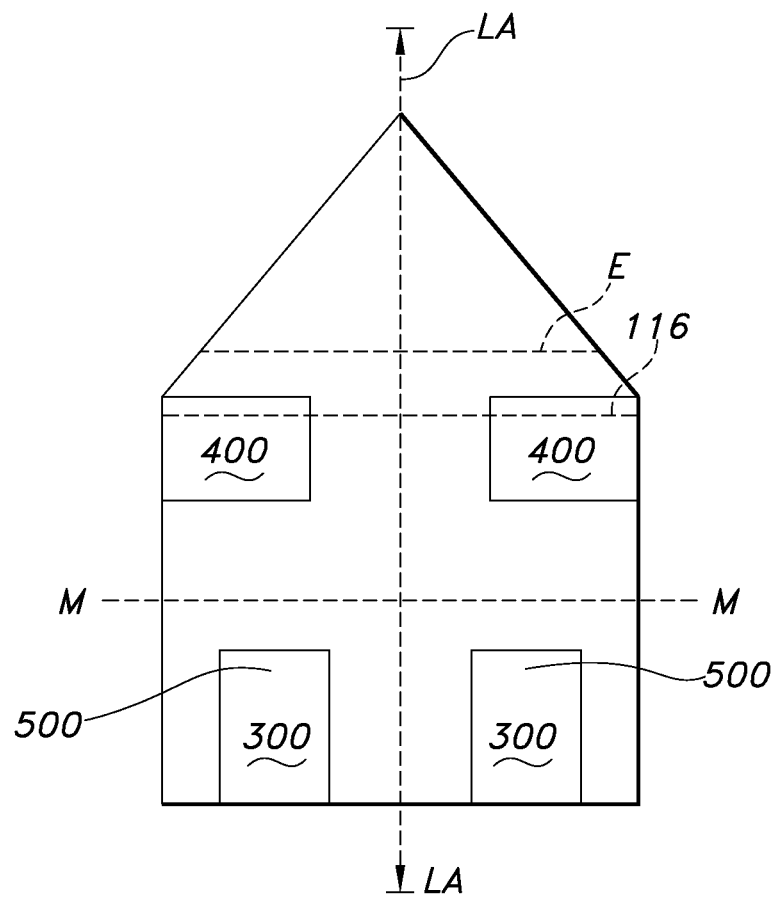
FIG. 6B is a bottom view illustration of an exemplary flexible multi-panel sterilization assembly including side tabs and pull tabs that are folded over onto the barrier panel.

The sterilization assembly 100 also has a longitudinal axis "LA" extending from at least the first end 114 to the second end 118 of the barrier panel 102, and more desirably, from the distal end 144 of the fold protection 108 to the second end 118 of the barrier panel, such that it bisects the assembly into a first portion 600 and a second substantially equal portion 602 (or second portion 602). Each portion has a common boundary along the longitudinal axis "LA" and the first portion 600 has least a first portion edge 604 (which in FIG. 6A is the first edge 120 and one-half of the second edge 122 of the barrier panel 102 along with the first edge 146 of the fold protection panel 108) and the second portion 602 has at least a second portion edge 606 (which in FIG. 6A is the third edge 124 and one-half of the second edge 122 of the barrier panel 102 along with the second edge 148 of the fold protection panel 108) that is generally a mirror image of the first portion edge 604. That is, the longitudinal axis "LA" represents a bisecting axis of symmetry, and each respective portion 600, 602 of the assembly 100 has a respective center of mass located between the longitudinal axis "LA" and its respective portion edge 604, 606. When side tabs 400 are considered in an unfolded flat position so as not to cover the portions 600 and 602, the respective centers of mass for portions 600 and 602 shift to reflect the weight and position contributions from the side tabs. According to the invention, the center of mass of the first portion 600 and an appropriately positioned side tab is closer to the first portion edge 604 than to the longitudinal axis "LA" and the center of mass of the second portion 602 and an appropriately positioned side tab is closer to the second portion edge 606 than to the longitudinal axis "LA".

While the barrier panel 102 of FIG. 6 is generally shown as having a square shape, the barrier panel 102 may be rectangular or may desirably have additional edges to define a non-square or non-rectangular shape. Portions of the edges may be arcuate or may otherwise be non-linear. Alternatively and/or additionally, the first edge 120 and the third edge 124 may converge or diverge so the edges are not parallel, thereby defining a barrier panel 102 having a more trapezoidal shape. It is also contemplated that other combinations of opposite edges may converge or diverge.

Figure 7A:
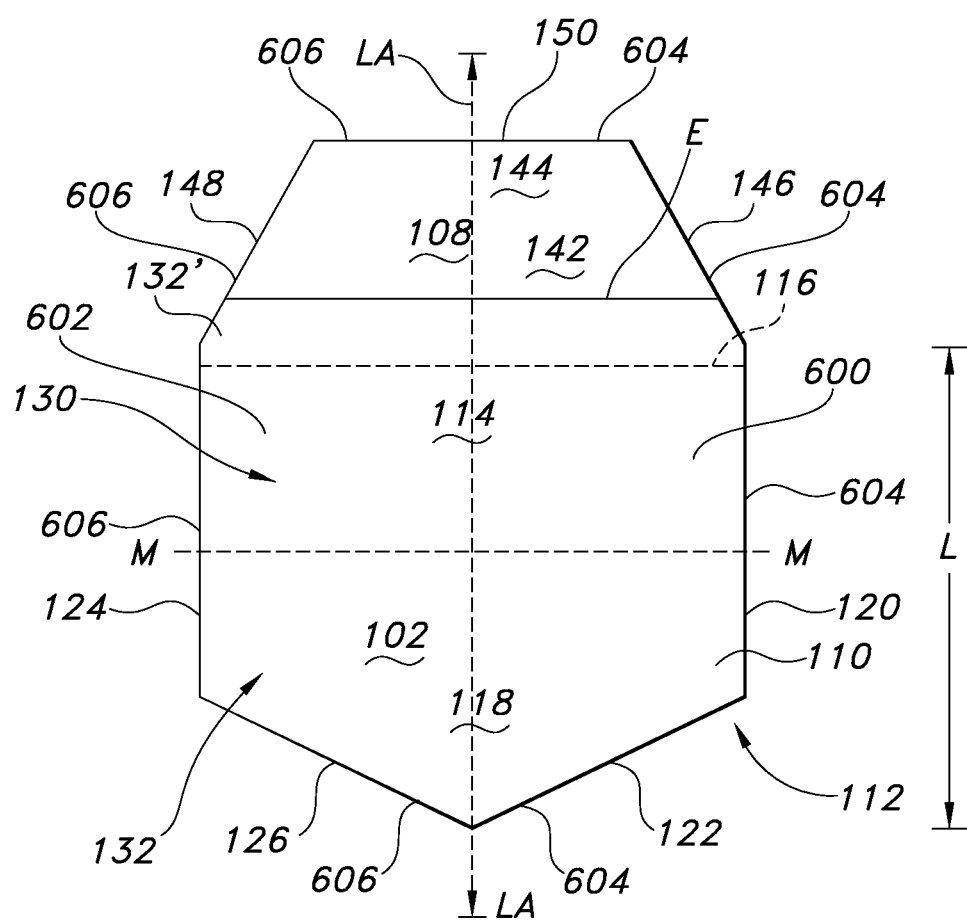
FIG. 7A is a top view illustration of an exemplary flexible multi-panel sterilization assembly including side tabs that are folded over onto the barrier panel (not shown in the top view).

For example and referring to FIG. 7A, the barrier panel may have a fourth edge 126 to define a non-square or non-rectangular shape. In such an exemplary configuration, the two edges 122 and 126 are generally opposite the pre-determined fold line 116 such that the second edge 122 and the fourth edge 126 form an apex or vertex. Thus, the barrier panel 102 may have a first surface 110 and a second opposing surface 112; a first end 114 having an edge or extremity "E" and that contains a pre-determined fold line 116 (also called indicia 116); a second end 118 opposite the first end 114; a first edge 120 that is generally perpendicular to the pre-determined fold line 116; a second edge 122 that is generally opposite the pre-determined fold line 116; a third edge 124 that is generally perpendicular to the pre-determined fold line; and a fourth edge 126 located between the second edge 122 and the third edge 124.

Figure 7B:
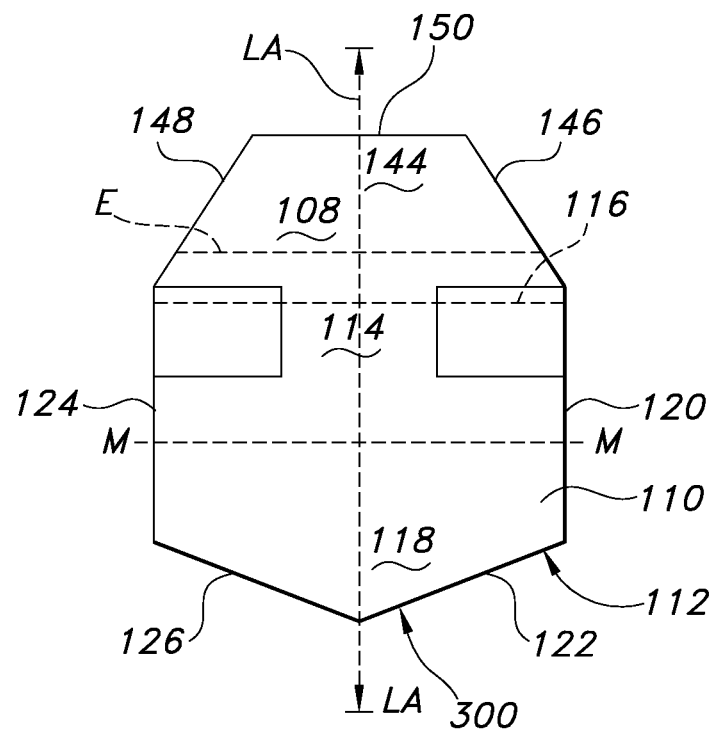
FIG. 7B is a bottom view illustration of an exemplary flexible multi-panel sterilization assembly including side tabs that are folded over onto the barrier panel.
Figure 7C:
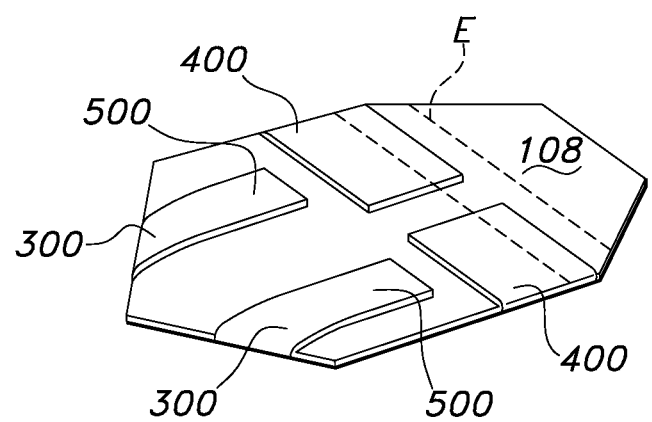
FIG. 7C is a bottom perspective view illustration of an exemplary flexible multi-panel sterilization assembly including side tabs and pull tabs with spaced apart pull locations; the side tabs and pull tabs are folded over onto the barrier panel.

As illustrated in FIGS. 7A and 7B, the sterilization assembly also has a longitudinal axis "LA" extending from at least the first end 114 to the second end 118 of the barrier panel 102, and more desirably, from the distal end 144 of the fold protection 108 to the second end 118 of the barrier panel, such that it bisects the assembly into a first portion 600 and a second substantially equal portion 602 (or second portion 602). Each portion has a common edge along the longitudinal axis "LA" and the first portion 600 has least a first portion edge 604 (which in FIG. 7A is the first edge 120 and the second edge 122 of the barrier panel 102 along with the first edge 146 and one-half of the third edge 150 of the fold protection panel 108) and the second portion 602 has at least a second portion edge 606 (which in FIG. 7A is the third edge 124 and the fourth edge 126 of the barrier panel 102 along with the second edge 148 and one-half of the third edge 150 of the fold protection panel 108) that is generally a mirror image of the first portion edge 604.

Figure 8A:
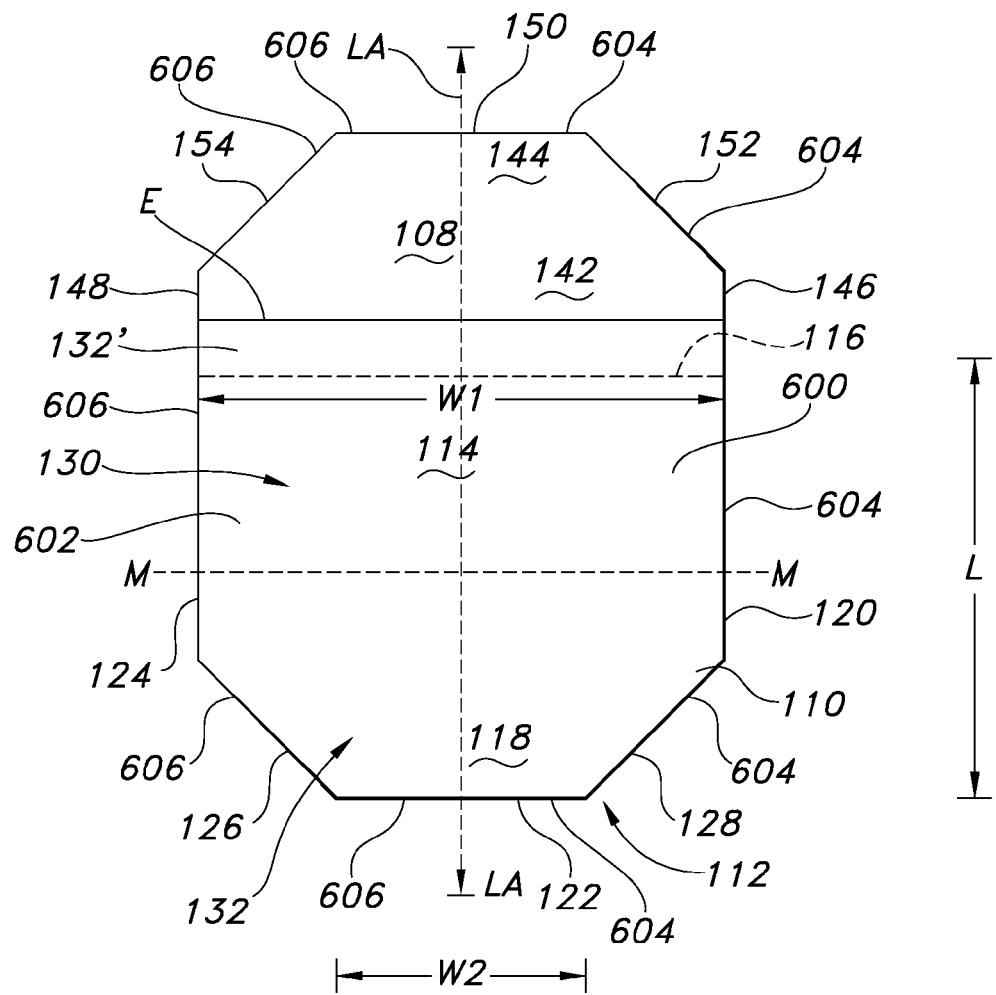
FIG. 8A is a top view illustration of an exemplary flexible multi-panel sterilization assembly including side tabs that are folded over onto the barrier panel (not shown in the top view).
Figure 8B:
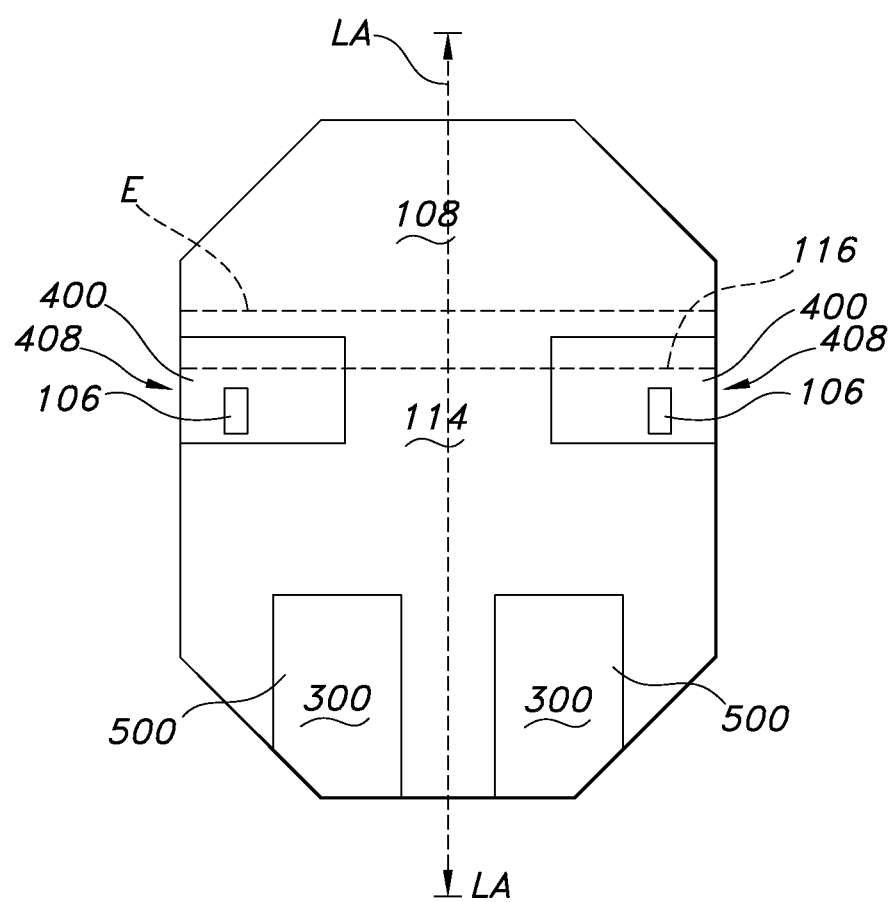
FIG. 8B is a bottom view illustration of an exemplary flexible multi-panel sterilization assembly including side tabs and pull tabs with spaced apart pull locations; the side tabs and pull tabs are folded over onto the barrier panel.

Referring to FIGS. 8A and 8B, the barrier panel 102 may have a fourth edge 126 and a fifth edge 128 to define a non-square or non-rectangular shape such that, for example, the fourth edge 126 and a fifth edge 128 generally converge toward the second edge 226 such that the second end 118 of the barrier panel is narrower than the first end 114 of the barrier panel. Thus, the barrier panel 102 may have a first surface 110 and a second opposing surface 112; a first end 114 having an edge or extremity "E" and that contains a pre-determined fold line 116; a second end 118 opposite the first end 114; a first edge 120 that is generally perpendicular to the pre-determined fold line; a second edge 122 that is generally parallel to the pre-determined fold line 116; a third edge 124 that is generally perpendicular to the pre-determined fold line 116; a fourth edge 126 located between the second edge 122 and the third edge 124; and, a fifth edge 128 located between the first edge 120 and the second edge 122. The barrier panel has a first width "W1" that is the distance from the first edge 120 to the third edge 124 in the first end 114 (e.g., preferably measured along the pre-determined fold line 116) and a second width "W2" that is the distance along the second edge 122 from the fourth edge 126 to the fifth edge 128 (e.g., preferably measured between the locations where the fourth edge 126 and the fifth edge 128 meet the second edge 122. The barrier panel also has an overall length that is the distance from the extremity "E" of the first end 114 to the extremity of the second end (e.g., at the second edge 122). In addition, the barrier panel has a length "L" from the pre-determined fold line 116 (or indicia 116) to the extremity of the second end 118 (e.g., at the second edge 122). An approximate midpoint "M" is located along this length "L" and is oriented from the first edge 120 and the third edge 124 or, in some embodiments, the fourth edge 126 and the fifth edge 128 to generally delineate the barrier panel 102 into a content receiving region 130 extending from the indicia 116 (also referred to as the pre-determined fold line 116) to the midpoint "M" and a content covering region 132 extending from the midpoint "M" to the second edge 122. Of course, it is contemplated that additional edges may be added or that edges may be curvilinear or may include curvilinear portions.

As illustrated in FIG. 8A, the sterilization assembly also has a longitudinal axis "LA" extending from at least the first end 114 to the second end 118 of the barrier panel 102, and more desirably, from the distal end 144 of the fold protection 108 to the second end 118 of the barrier panel, such that it bisects the assembly into a first portion 600 and a second substantially equal portion 602 (or second portion 602). Each portion has a common edge along the longitudinal axis "LA" and the first portion 600 has least a first portion edge 604 (which in FIG. 8A is the first edge 120, the fifth edge 128 and one-half of the second edge 122 of the barrier panel 102 along with the first edge 146, the fourth edge 152 and one-half of the third edge 150 of the fold protection panel 108) and the second portion 602 has at least a second portion edge 606 (which in FIG. 8A is the third edge 124, the fourth edge 126 and one-half of the second edge 122 of the barrier panel 102 along with the second edge 148, the fifth edge 154 and one-half of the third edge 150 of the fold protection panel 108) that is generally a mirror image of the first portion edge 604.

Referring again to FIG. 6A, the barrier panel 102 may have a width "W" that is the distance from the first edge 120 to the third edge 124 and an overall length that is the distance from the extremity "E" of first end 114 to the extremity of the second end 118 (e.g., at the second edge 122). The barrier panel also has a length "L" from the pre-determined fold line 116 (or indicia 116) to the extremity of the second end 118 (e.g., at the second edge 122). An approximate midpoint "M" along this length "L" is oriented from the first edge 120 and the third edge 124 to generally delineate the barrier panel 102 into a content receiving region 130 extending from the pre-determined fold line 116 to the midpoint "M" and a content covering region 132 extending from the midpoint "M" to the second edge 122. Generally speaking the content receiving region is the portion of the barrier panel onto which a tray or other content to be sterilized is initially placed. Unlike conventional sterilization wrap in which a tray or content to be sterilized is placed in the central portion of the barrier material that forms the sterilization wrap, the content receiving region is between the indicia 116 (also referred to as the pre-determined fold line 116) and the midpoint "M" of the barrier panel. This asymmetric placement on the barrier panel is not intuitive. Content covering regions are the portions of the barrier panels that are folded up and over contents after the contents have been placed on the content receiving regions. Referring to FIGS. 6A, 7A and 8A, when the extremity "E" of the first end 114 of the barrier panel does not coincide with the indicia 116 (also referred to as the pre-determined fold line 116), an additional content covering region 132' may be present between the indicia 116 and the "E" of the first end 114 of the barrier panel. That is, in another aspect of the invention, the content covering portion of the barrier panel 102 also includes the portion of the barrier panel 132' located between the pre-determined fold line 116 (also called the indicia 116) and the extremity "E" of the first end 114 that defines a boundary or transition between the barrier panel 102 and the fold protection panel 108.

In an aspect of the invention, the barrier panel of the various illustrated configurations may have a width of from about 12 inches (~30 cm) to about 50 inches (~127 cm). Desirably, the barrier panel may have a width of from about 18 inches (~46 cm) to about 40 inches (~102 cm). Even more desirably, the barrier panel may have a width of from about 20 inches (~51 cm) to about 48 inches (~122 cm). The barrier panel may have a length of from about 7 inches (~18 cm) to about 70 inches (~178 cm). Desirably, the barrier panel may have a length of from about 15 inches (~39 cm) to about 70 inches (~178 cm). Even more desirably, the barrier panel may have a length of from about 20 inches (~64 cm) to about 70 inches (~178 cm).

According to an aspect of the invention, the surface area of the content receiving region 130 may be from about 25 percent to about 49 percent of the total surface area of the barrier panel 102. For example, the surface area of the content receiving region 130 may be from about 35 percent to about 45 percent of the total surface area of the barrier panel 102. This is important because the content covering region or regions of the barrier panel should be larger to provide additional surface area to properly cover the content.

Figure 8C:
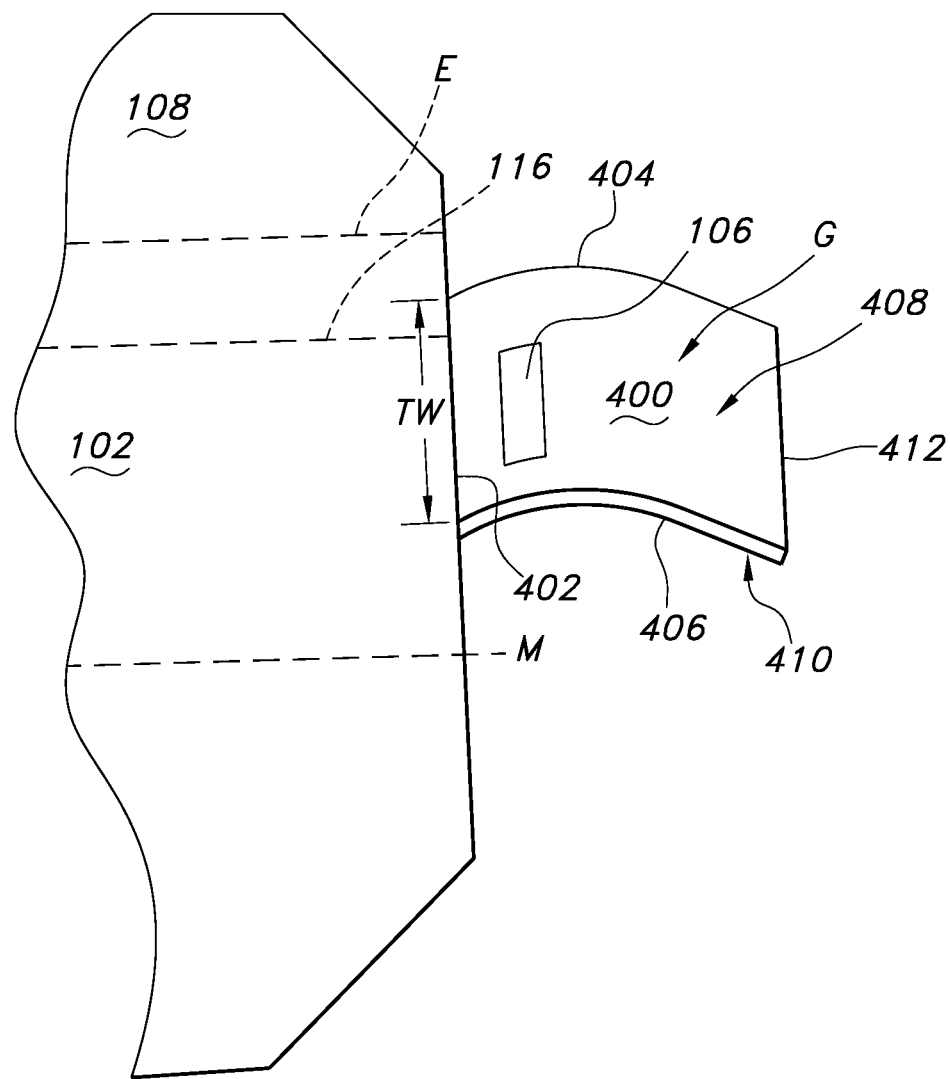
FIG. 8C is an illustration of a detail of an exemplary unfolded side tab located on a flexible multi-panel sterilization assembly.
Figure 8D:
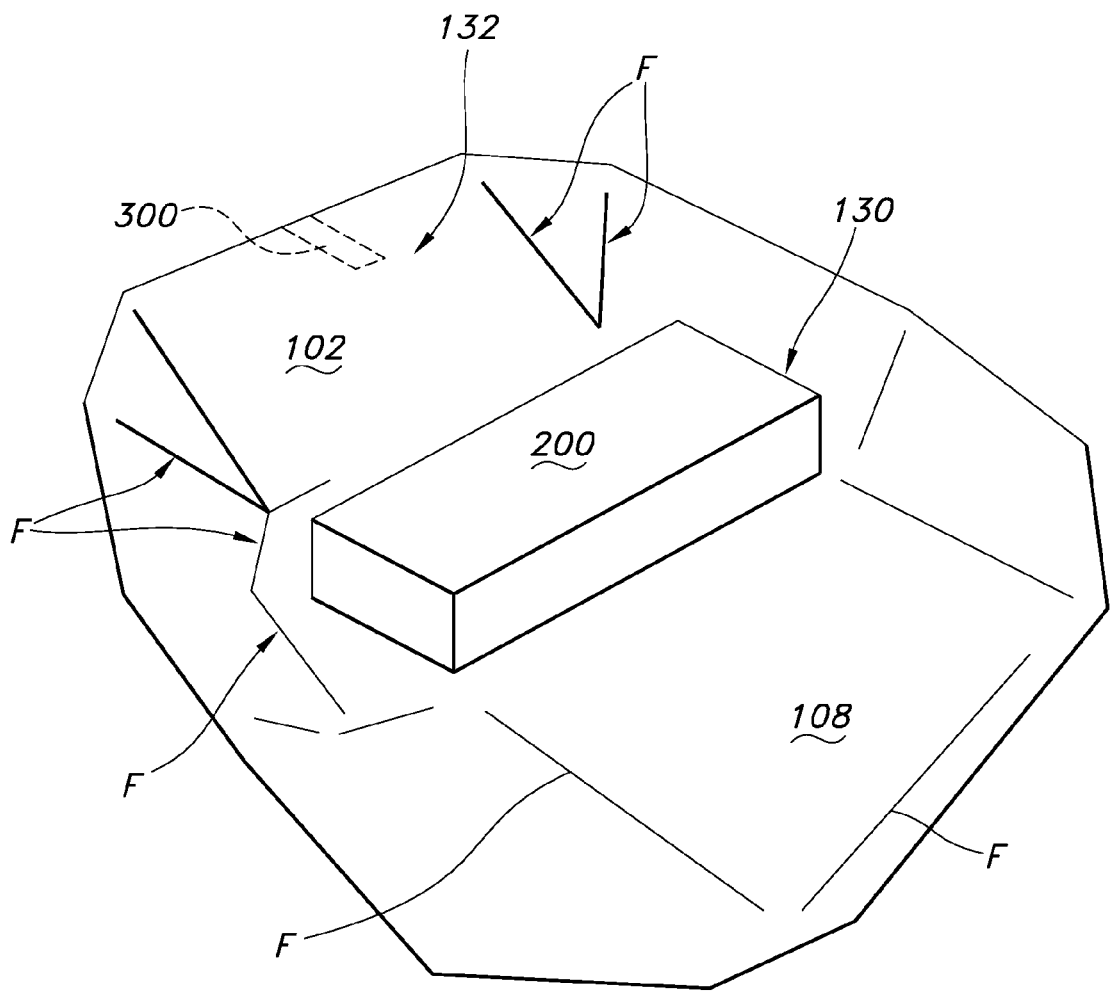
FIG. 8D is in illustration of sterilization assembly during unfolding highlighting imprinted creases, folds and other deformations that prevent portions of the assembly from laying flat during unfolding.
Figure 8E:
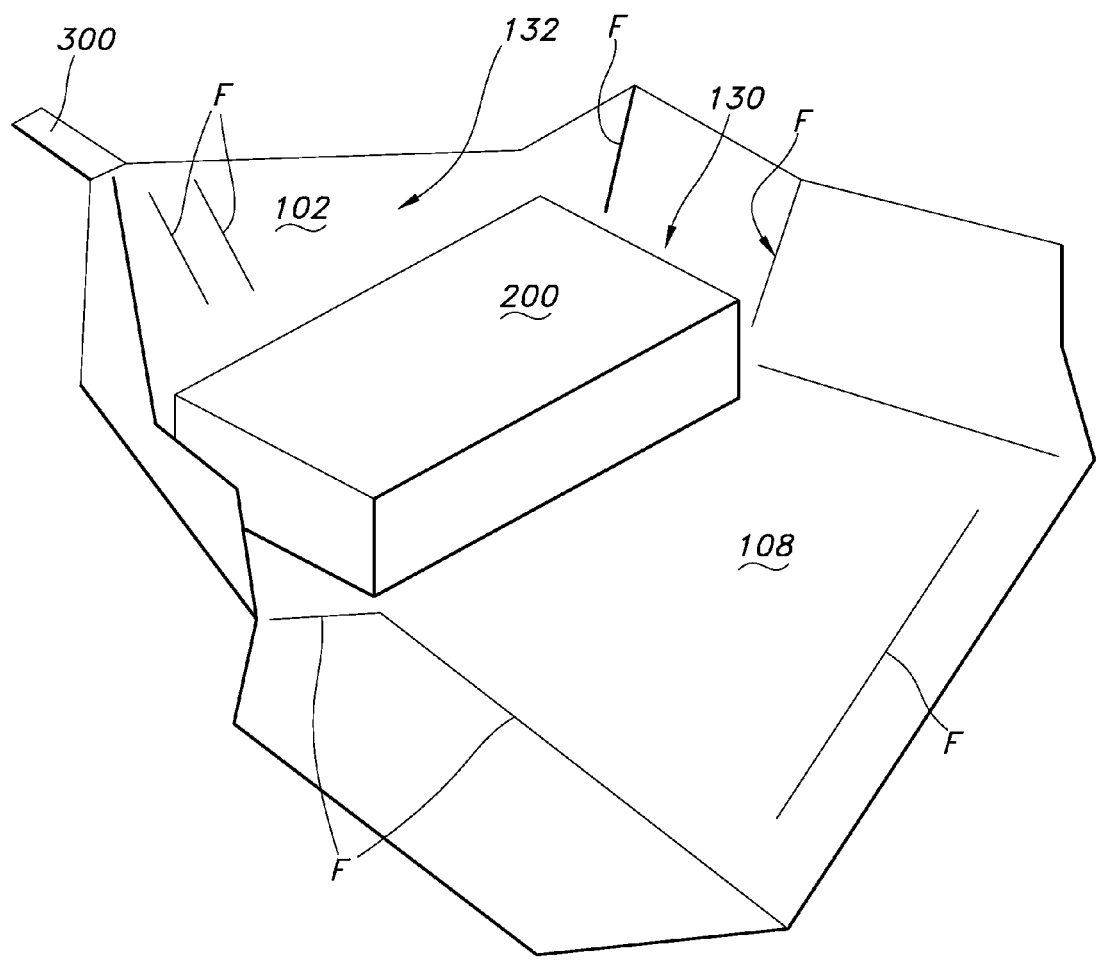
FIG. 8E is in illustration of sterilization assembly during unfolding highlighting imprinted creases, folds and other deformations that cause partially unfolded sides of the assembly to fold back up towards the sterilized article or tray while other portions of the assembly are being unfolded.

An important part of the multi-panel sterilization assembly of the present invention is the side tabs. These side tabs provide grip locations for folding and unfolding the barrier panel. Importantly, these side tabs help prevent unfolded portions of the barrier panel from folding back towards the sterilized contents during unfolding of other portions of the sterilization assembly, particularly after enhanced steam or heat sterilization. In the absence of these side tabs, the side edges of the barrier panel may fold back up towards or even onto the sterilized content. Referring now to FIGS. 8D and 8E, when a sterilization wrap or sterilization assembly composed of a material made from certain thermoplastic polymers are used in an steam or heat sterilization processes, the material may set or "imprint" the shape of the wrapped article or tray. During unwrapping of the article or tray 200, these imprinted creases, folds or other deformations identified as "F" in FIG. 8D must be overcome during unfolding so the sterilization assembly can lay substantially flat. If the sterilization assembly does not lie substantially flat, it is possible for previously unfolded sides of the sterilization assembly to fold back up towards the sterilized article or tray while other portions of the assembly are being unfolded. This phenomenon can compromise the sterility of the article or tray 200. Ordinarily, one would seek to make the material of the sterilization assembly or wrap softer, more flexible and compliant so it would fold and unfold easily and be able to lay flat during unwrapping/unfolding after sterilization. However, making the material softer or more flexible creates additional expense and may compromise the strength of the material. Alternatively, one might seek to reinforce the material and make it stiffer or add more material such as, for example, a wide strip along the edge of the barrier panel. However, it has been found that adding more material frequently tends to strengthen or enhance the tendency of the imprinted crease, fold or other deformation to fold back up. It is believed that adding more material at the "F" fold, crease or deformation locations allows more material to "heat set" thus increasing the resistance to unfolding. It is also thought that a very large amount of material is required to provide sufficient weight to begin to counterbalance the resistance to unfolding and that such a large amount of material is uneconomical to employ and would create difficulties during manufacture and use. The additional weight of material also lowers the breathability of the wrap.

It was unexpectedly discovered that adding side tabs to the sterilization assembly significantly reduces or eliminates the likelihood of previously unfolded sides of the sterilization wrap folding back up over the sterilized article or tray while other portions of the wrap are being unfolded. Joining the side tabs to the barrier panel at or near the edges of the barrier panel serves to add weight beyond the edges of the barrier panel, which relocates or shifts the center of mass of the side tab-assembly portions to help eliminate the likelihood of previously unfolded sides of the sterilization wrap folding back up over the sterilized article or tray while other portions of the wrap are being unfolded.

Referring to FIGS. 6 to 8C, the barrier panel 102 includes side tabs 400 located at or adjacent the first edge 120 and the third edge 124 of the barrier panel. These side tabs 400 help prevent the first and third edges of the barrier panel from folding back on itself during unfolding of the sterilization assembly, particularly after extended steam or heat sterilization. The side tabs 400 can be located at or adjacent the first and third edges (120 and 124, respectively) of the content covering region 132 of the barrier panel 102. Desirably, the bulk of a side tab 400 is located between the extremity "E" of the first end and the midpoint of the barrier panel and at or near the first edge and the third edge such that the side tab 400 spans the indicia 116 (also called pre-determined fold line 116). Generally speaking, the side tabs 400 may be located on the second opposing surface 112 of the barrier panel 102 as illustrated in FIGS. 6B, 7B, 7C, 7D and 8B. Alternatively and/or additionally, side tabs 400 may be located on the first surface 110 of the barrier panel 102. For example, the side tabs 400 may be configured such that a portion of the side tab is attached to the first surface 110 and another portion is attached to the second opposed surface 112.

An attached side tab that adjoins the content receiving region and with a weight of only 0.028 ounce has been found to be insufficient to shift the center of mass of the first or second portion to ensure aseptic opening of the assembly after wrapping and sterilizing; the weight contribution of the side tab, inclusive of any panel attachment means, needs to be greater than 0.028 ounce. That is, the weight contribution of the side tab, inclusive of any panel attachment means, may range from just above 0.028 ounce up to several ounces. Heavier weights are contemplated, but they may not provide particular advantage to offset the cost and complexity of provided the additional weight. While the inventors should not be held to any particular theory of operation, it has been found that only a relatively small amount of additional weight contribution by the side tabs is required to reliably provide for aseptic opening of the assembly after wrapping and sterilizing. That is, during unfolding of the assembly the user must release the side tabs 400 in order to grasp the second end 118 of the barrier panel (or to grasp the pull tab 300 and its spaced apart pull locations 500 located at/on the second end 118)—only a small amount of additional weight in appropriately positioned side tabs shifts the center of mass is required to reliably provide for aseptic opening of the assembly by helping reliably prevent unfolded sides of the sterilization assembly from folding back up over the sterilized article or tray while other portions of the wrap are being unfolded. For example, the weight contribution of the side tab, inclusive of any panel attachment means, may range from just above 0.028 ounce (~0.03 ounce) up to about 3 ounces. As another example, the weight contribution of the side tab, inclusive of any panel attachment means, may range from just above ~0.03 ounce up to 1 ounce. As yet another example, the weight contribution of the side tab may range from just above ~0.03 ounce up to 1 ounce. The weight contribution of the side tab may range from just above ~0.03 ounce up to 0.5 ounce. The weight contribution of the side tab may range from just above ~0.03 ounce up to 0.1 ounce. As another example, the weight contribution of the side tab may range from just above ~0.03 ounce up to 0.09 ounce.

In an aspect of the present invention, the sterilization assembly includes at least one pull tab 300 (or pull tab system 300) that provides spaced apart pull locations 500. Generally speaking, the pull tab system 300 may be located on the second opposing surface 112 of the barrier panel 102 as illustrated in FIGS. 6B, 7C, 7D and 8B. Alternatively and/or additionally, the pull tab system 300 may be partially located on the first surface 110 of the barrier panel 102. For example, the pull tab system 300 may be configured such that a portion of the pull tab is attached to the first surface 110 and another portion is attached to the second opposed surface 112.

In another aspect of the invention, the side tabs may be attached to the barrier panel such that the side tabs may be readily separated from the barrier panel after use (i.e., after sterilization and unfolding of the sterilization assembly to reveal the sterilized content). Alternatively and/or additionally, the attachment of the pull tabs may be such that the pull tabs may be readily separated from the barrier panel after use (i.e., after sterilization and unfolding of the sterilization assembly to reveal the sterilized content). This may be particularly advantageous where components such as panel attachments means are present on the side tabs and portions of the panel attachments means are made of a material that is incompatible for recycling with the material(s) that form other portions of the sterilization assembly. It is contemplated that the side tabs may be unitary or integral to the barrier panel (e.g., they may be formed from a single piece of material. In such case, the side tabs may include a frangible portion such that the side tabs may be readily separated from the barrier panel.

The side tabs (and/or the pull tab(s)) may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Nonwoven webs may include, for example, spunbond, meltblown, carded webs, wet formed or airlaid webs, hydroentangled fabric, or laminates of the same (e.g., spunbond/meltblown/spunbond). Such nonwoven webs may also include natural or synthetic materials or blends of the same. The side tabs may include one or more layers of material selected from permeable or impermeable films or laminates of the same. Permeable films may be apertured or be microporous. Apertured films may be obtained through mechanical aperturing, vacuum aperturing, or other commercially available techniques. Microporous films and other similar films may be produced as generally described at, for example, U.S. Pat. No. 5,695,868; U.S. Pat. No. 5,698,481; U.S. Pat. No. 5,855,999; and U.S. Pat. No. 6,277,479; the contents of which are incorporated herein by reference. Impermeable films can be monolayer or coextruded and can be comprised of film materials including, for example, polyethylenes, polypropylenes, copolymers thereof, vinyls, metal foils, and the like. It should also be noted said films may also be laminated with fibrous webs, described above.

For example, the side tabs (and/or the pull tab(s)) may be a layer or layers of nonwoven material that is joined to the barrier panel by adhesives, thermal bonding, ultrasonic bonding or other techniques or combinations of techniques. For example, each side tab may be a layer of nonwoven material such as, for example, a laminate of two layers of spunbond fabric sandwiching a layer of meltblown fabric (commonly referred to as "SMS" material). Each layer may extend directly from or generally adjacent the respective first and third edges of the barrier panel. For example, the side tab may extend from at or adjacent the edge to a few inches inward from the edge.

Each side tab may be joined to the barrier panel over only a portion of its surface that directly contacts the barrier panel. Alternatively, each side tab may be joined to the barrier panel over the entire surface of the side tab that directly contacts the barrier panel. For example, the side tab may be joined to the barrier panel utilizing a spray of adhesive, a slot-coat application of adhesive, swirl pattern of adhesive over that entire contacting surface—or over only a portion of that contacting surface and particularly to attach the portions of the side tabs that are inward from the edges of the barrier panel. The portions of the side tabs that are at or immediately adjacent from the edges of the barrier panel may be attached utilizing adhesives as described above or by ultrasonic bonding, thermal bonding, pressure bonding or other techniques. When adhesives are utilized, the adhesive should withstand sterilization conditions. It is contemplated that an adhesive which can add to the weight and/or stiffness of the side tab would be desirable.

The multi-panel sterilization assembly 100 may include a panel attachment means 106. For those embodiments where the side tabs have rectangular shapes the panel attachment means may desirably be located on a side tab 400 as generally illustrated in FIG. 8C.

Figure 7D:
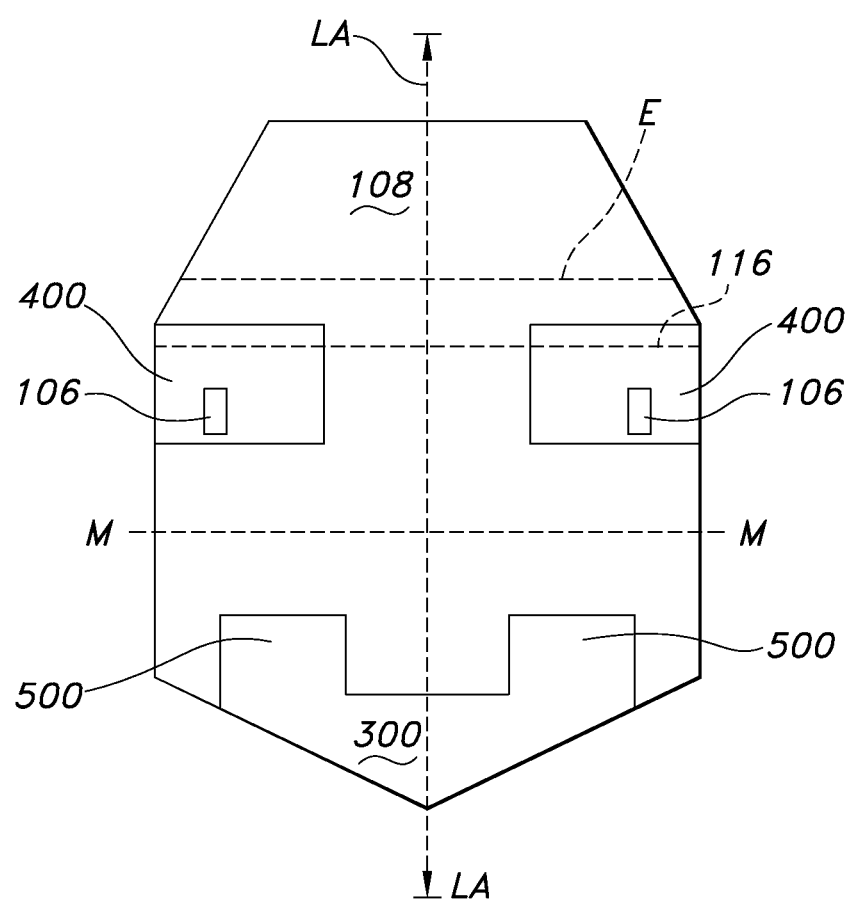
FIG. 7D is a bottom view illustration of an exemplary flexible multi-panel sterilization assembly including side tabs and a pull tab with spaced apart pull locations; the side tabs and pull tabs are folded over onto the barrier panel.

Each side tab 400 may include a proximal tab end 402 generally adjacent the respective first edge or third edge of the barrier panel, a first tab edge 404 generally perpendicular to the proximal tab end and at least a second tab edge 406 such that the first tab edge 404 and the second tab edge 406 define a tab width "TW" at the proximal tab end 402. The side tab may also have a distal tab end 412 opposite the proximal tab end 402. According to an aspect of the invention, the tab width "TW" should desirably extend a distance from a first location at or near the first end of the barrier panel (e.g., a location at or above the indicia 116 and at or below where the barrier panel 102 transitions to the fold protection panel 108—identified in FIG. 8C as extremity "E") to at least a second location below the indicia 116 and within the content receiving region (e.g., to a second location on the barrier panel 102 that is located below the indicia 116 in the direction toward the midpoint "M" of the barrier panel). The panel attachment means 106 is desirably located on a first tab surface 408 generally near the proximal tab end 402 (i.e., near the first edge 120 and/or or the third edge 124 of the barrier panel). Alternatively and/or additionally, the panel attachment means 106 may be located near the distal tab end or between the two tab ends. The panel attachment means should be located below the indicia 116 (the "pre-determined fold line") as generally illustrated in FIGS. 7D, 8B and 8C.

Alternatively and/or additionally, the panel attachment means 106 may be located at or adjacent the first edge 120 and the third edge 124 of the barrier panel. That is, the panel attachment means may be located directly on the first surface 110 of the barrier panel 102. In such a configuration, the panel attachment means 106 should be located below the indicia 116 (the "pre-determined fold line").

An imprinted crease, fold or other deformation occurs at the indicia 116 (also called the pre-determined fold line 116) as a result of sterilization. While the inventors should not be held to a particular theory of operation, it is believed that having the tab width "TW" of the side tab at the proximal tab end 402 span the indicia 116 enables the side tab to distribute forces during opening of the package to effectively and reliably prevent unfolded sides of the sterilization assembly from folding back up over the sterilized article or tray while other portions of the wrap are being unfolded. In addition, the unfolded side tabs 400 cause the center of mass of each of the assembly portions 600, 602 to shift by a sufficient amount to reliably prevent unfolded sides of the sterilization assembly from folding back up over the sterilized article or tray while other portions of the wrap are being unfolded.

The panel attachment means may be one large element or a number of discrete elements. Exemplary panel attachment means include, but are not limited to, adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof.

For example, the panel attachment means may be one or more lengths of adhesive tape having at least an end or portion that is stitched, ultrasonically bonded, thermo-mechanically bonded or adhered or adhesively bonded to the barrier panel. Desirably, the panel attachment means is a barrier panel attachment means located on the side tabs that is used to join one or more edges of the barrier panel that are folded around content to be sterilized. It has been found that barrier panel attachment means may be a double sided tape having the same or different levels of adhesive or tack strength of adhesive on each side. Alternatively and/or additionally, the panel attachment means may have a double sided tape structure in which the central layer sandwiched by the adhesive is a splittable or separable material such as a splittable paper, splittable laminate, splittable foam, cleavable paper, cleavable release structure, cleavable foam or other cleavable or separable laminate. Exemplary splittable or cleavable materials are disclosed at, for example, U.S. Pat. No. 5,702,555 issued to Caudal et al. on Dec. 30, 1997; U.S. Pat. No. 4,310,127 issued to Frye on Jan. 12, 1982; U.S. Pat. No. 3,675,844 issued to Sorrell on Jul. 11, 1972; and U.S. Pat. No. 2,205,956 issued to Humphner on Jun. 25, 1940; the contents of which are incorporated by reference.

Suitable panel attachment means 106 that include or incorporate adhesive tape may be in the form of an adhesive fastening tab or tape closure system such as the various types frequently used on diapers, incontinent garments and similar products. An exemplary tape closure system may be found at, for example, U.S. Pat. No. 4,410,325 issued to Lare on Oct. 18, 1983; the contents of which are incorporated by reference. This system utilizes an adhesive closure system (referred to herein as a "closure system") that is folded back on itself and which has a first end or portion that is attached to the article (e.g., one part of a garment). During use, the closure system is unfolded to reveal an exposed adhesive surface at least at a second end or portion of the closure system which is then adhered to a different part of the article (e.g., a second part of the garment) to secure the two parts of the garment in the desired configuration. Generally speaking, the closure system is desirably used on the side tabs 400 that are located at the first edge 120 and the third edge 124 (although it may be used directly on the barrier panel 102). The first end of the panel attachment means 106 (in the form of the closure system) would be secured on the first tab surface 408 or would be secured at or near the distal tab end 412 of the side tab 400 and the second end of the panel attachment means 106 would be folded back onto the first end. During use, the panel attachment means 106 would be unfolded to reveal an exposed adhesive surface or surfaces at least at the second end of the panel attachment means 106. The exposed adhesive surface(s) of the panel attachment means on the side tabs 400 at first edge 120 and/or third edge 124 of the barrier panel would be used to secure those portions of the barrier panel to each other and/or to other portions of the barrier panel after the barrier panel is folded about content to be sterilized.

It is contemplated that an optional attachment zone may be utilized. In embodiments that utilize adhesive or cohesive materials for the panel attachment means, an attachment zone may be an applied film, a more securely bonded portion of a nonwoven fabric, a separate piece of a material, a coating or the like that provides a suitable surface for the adhesive to bond securely so the folded barrier panel does not "pop" open or release when it should not do so. The attachment zone may be configured to signal to a user the appropriate location or locations to secure the panel attachment means. In such configuration, the attachment zone may be combined with or may incorporate indicia such as color, texture, alphanumeric characters or the like to direct a user. More importantly, the attachment zone can be configured to provide a suitable surface such that the force required to release the panel attachment means 106 is carefully controlled to preserve aseptic opening, avoid tearing or shredding of the barrier fabric, provide a satisfactory level of resistance to sheer forces, and/or provide a satisfactory or controlled level of resistance to peel forces.

Another exemplary tape closure system may be found at, for example, U.S. Pat. No. 4,585,450 issued to Rosch et al. on Apr. 29, 1986; the contents of which are incorporated by reference. This system utilizes an adhesive closure system (referred to herein as a "closure system") that includes a secondary tape element and a primary tape element. The closure system has a first end or portion that is attached to the article (e.g., one portion of a garment). The second end or portion contains the secondary tape element and primary tape element. During use, an adhesive surface of the primary tape element is exposed. The adhesive surface of the primary tape element is then adhered to a different part of the article (e.g., a second part of the garment) to secure the two parts of the garment in the desired configuration. An adhesive bond between the primary tape element and the secondary tape element has less strength than the adhesive bond between the primary tape element and the second part of the garment or article such that the bond between the primary tape element and secondary tape element may be reliably separated, repeatedly if necessary.

Generally speaking, the closure system is desirably used on the side tabs 400 that are located at the first edge 120 and the third edge 124 (although it may be used directly on the barrier panel 102). The first end or first side of the panel attachment means 106 (in the form of the closure system) would be secured on the first tab surface 408 or would be secured at or near the distal tab end 412 of the side tab 400 and the second end or the second side of the panel attachment means 106 would be folded back onto the first end or otherwise covered by a release element. During use, the primary tape element of the panel attachment means 106 (in the form of the closure system) would be unfolded or uncovered to reveal an exposed adhesive surface(s) at least at the second end or second side of the panel attachment means 106. The exposed adhesive surface(s) of the panel attachment means on the side tabs 400 at first edge 120 and/or third edge 124 of the barrier panel would be used to secure those portions of the barrier panel to each other and/or to other portions of the barrier panel after the barrier panel is folded about content to be sterilized. In such a configuration, the adhesive bond between the primary tape element and the secondary tape element has less strength than the adhesive bond between the primary tape element and the portion of the side tab to which it is adhered such that the bond between the primary tape element and secondary tape element may be reliably separated, repeatedly if necessary. In some respects, the primary tape element may function as an attachment zone. That is, after the primary tape element is adhered to the barrier panel to secure the barrier panel in a folded configuration, the primary tape element may provide a suitable surface such that the force required to overcome the adhesive bond between the primary tape element and the secondary tape element is carefully controlled to preserve aseptic opening, avoid tearing or shredding of the barrier fabric, provide a satisfactory level of resistance to sheer forces, and/or provide a satisfactory or controlled level of resistance to peel forces. In another aspect, the attachment zone as describe previously or in the form of the primary tape element may be used to allow a worker to re-open the wrapped barrier panel prior to inspect contents prior to sterilization and then re-attach the panel attachment means without having to destroy the multi-panel sterilization assembly.

As another example, the panel attachment means may be a hook fastener component from a hook and loop fastening system joined to the side tab (and/or to a portion of the barrier panel). It is contemplated that the barrier fabric itself may function as the loop component of a hook and loop fastening system such as hook and loop fastenings systems available as VELCRO® brand fastener products from Velcro Industries B. V. Other exemplary hook systems may be used such as the hook system described in U.S. Pat. No. 5,315,740 issued to Nestegard which relates to hooks having small dimensions so they engage low cost loop materials such as nonwoven webs.

It is contemplated that various elements or components of the panel attachment means, may be integrally formed, such as by molding, co-extrusion or the like, along with any associated substrate layer. For example, the individual hook elements may be integrally formed simultaneously with a hook base-layer by coextruding the base layer and hook elements from substantially the same polymer material.

The panel attachment means 106 may be a double sided tape having a length that is greater than its width. For example, the panel attachment means may be a double sided tape having a length that more than two times great than its width. As another example, the panel attachment means may be a double sided tape having a length that is four times great than its width to eight times greater than its width. Alternatively and/or additionally, the configuration of the panel attachment means may be a series of tape squares arranged along a dimension or within the dimensions of the side tab 400.

According to an aspect of the invention, the panel attachment means 106 may be located on the barrier panel or on the side tabs (or both) so that it is near the pre-determined fold line 116, but the panel attachment means 106 should avoid substantially spanning or crossing the pre-determined fold line 116. That is, the panel attachment means 106 should desirably avoid being in position such that it is creased or folded during folding of the multi-panel assembly into a package around an article. Desirably, the portion of the panel attachment means 106 closest to the pre-determined fold line 116 is less than about 3 inches away from the pre-determined fold line 116 in the direction toward the midpoint "M" of the barrier panel 102. More desirably, the portion of the panel attachment means 106 closest to the pre-determined fold line 116 is desirably less than about 2 inches from the pre-determined fold line 116. For example, the portion of the panel attachment means 106 closest to the pre-determined fold line 116 may be about 1 inch to about ½ inch from the pre-determined fold line 116.

Referring again to FIG. 6A, the fold protection panel 108 of the multi-panel sterilization assembly 100 is in juxtaposed communication with the barrier panel 102. That is, the fold protection panel 108 is in side-by-side relationship with or adjoins the barrier panel 102. Generally speaking, the fold protection panel 108 may be any suitable material but desirably is formed of a permeable sheet material. According to the invention, the fold protection panel includes a proximal end 142 generally adjacent the extremity "E" of the first end 114 of the barrier panel 102; a distal end 144 generally opposite the proximal end 142; and at least a first edge 146 and a second edge 148 extending from the proximal end 142 to the distal end 144. According to the present invention, the fold protection panel may have additional edges. For example and with reference to FIG. 7A, the fold protection panel may include at least a third edge 150 located at or along its distal end 144. As yet another example and referring now to FIG. 8A, the fold protection panel may include at least a third edge 150 located at or along its distal end 144 and a fourth edge 152 and a fifth edge 154.

Generally speaking, the fold protection panel may be a lightweight material such as a lightweight spunbond nonwoven material or a lightweight laminate of spunbond nonwoven material and meltblown nonwoven material. As such, the fold protection panel does not need to provide a higher level of barrier properties like the material that forms the barrier panel. The fold protection panel may be configured so it has barrier properties. For example, the fold protection panel may be formed of the same material as the barrier panel. It is contemplated that the fold protection panel may be a single layer of spunbond nonwoven material.

In an aspect of the invention, the fold protection panel desirably has a width that is the distance from the first edge to the second edge and a length that is the distance from the proximal end to the distal end. The fold protection panel may have a width of from about 12 inches (~30 cm) to about 50 inches (~127 cm). Desirably, the fold protection panel may have a width of from about 18 inches (~46 cm) to about 40 inches (~102 cm). Even more desirably, the fold protection panel may have a width of from about 20 inches (~51 cm) to about 48 inches (~122 cm). The fold protection panel may have a length of from about 6 inches (~15 cm) to about 30 inches (~76 cm). Desirably, the fold protection panel may have a length of from about 8 inches (~20 cm) to about 20 inches (~51 cm). Even more desirably, the fold protection panel may have a length of from about 12 inches (~30 cm) to about 15 inches (~38 cm).

During use, panel attachment means 106 are used to securely position the barrier panel's first edge 120 and third edge 124 to a portion of the content covering region 132 after the barrier panel 102 has been folded at or near its midpoint "M" such that its second end 118 is brought near its first end 114. It is contemplated that in some embodiments, the panel attachment means 106 may be used to securely position the barrier panel's first edge 120 and third edge 124 to each other.

According to an aspect of the invention, it is important that the adhesive force or the engagement force at which the panel attachment means securely position the respective edges of the barrier panel to the content covering region or to the edges themselves should be sufficient to maintain the barrier panel around the content thereby forming a package that is robust and able to withstand normal handling before as well as after sterilization.

In exemplary arrangements, especially where there are sufficiently high levels of engagement shear force provided by the panel attachment means, the fastening engagement may provide a peel force value of not less than a minimum of about 5 grams-force (gmf) (about 0.012 lbs-force) between the panel attachment means and the other portion of the barrier panel that it secures together. Generally speaking, the peel force should not be more than about 500 gmf, and desirably is not more than about 400 gmf to further provide improved benefits. In further arrangements, the fastening engagement may provide a peel force value of between about 6 gmf and about 50 gmf to provide improved advantages. In desired configurations, the fastening engagement may provide a peel force value about between about 10 gmf and about 400 gmf between the panel attachment means and the other portion of the barrier panel that it secures together. More desirably, the peel force value may be between about 15 gmf and about 300 gmf. When the peel force is greater than about 500 gmf, there is difficulty opening/unwrapping the folded assembly containing sterilized contents in an aseptic manner.

The engagement force between the panel attachment means and the other portion of the barrier panel that it secures together may additionally provide a shear force value that is desirably greater than about 1330 gmf.

It should be readily appreciated that the adhesive force or the engagement force at which the panel attachment means securely position the respective edges of the barrier panel to the content covering region of the barrier panel or to the edges themselves should be less than the peel strength of the bond that is used to join the panel attachment means to the underlying barrier panel or component such as the side tabs during construction of the assembly. For example, the peel strength of the bond (e.g., adhesive, mechanical, thermo-mechanical, ultrasonic, etc.) that is used to join the panel attachment means to the side tabs during construction should be much greater than the detachment force for the panel attachment means from the barrier panel. For a panel attachment means having a dimension of about 4 inches by 1 inch (about 10 cm by 2.5 cm) the bond joining the panel attachment means to the side tab should have a peel strength of at least 100 gmf. Desirably, the peel strength of the bond that is used to join the panel attachment means to the side tabs during construction should be greater than about 400 gmf. For example, the peel strength may be more than 100 gmf/square inch, and may be more than 4,000 gmf/square inch. When the panel attachment means are located on or joined to the side tabs 400, it is important that the adhesive force or the engagement force at which the panel attachment means join the respective edges of the barrier panel to the content covering region of the barrier panel or to the edges themselves should be less than the strength of the bond between the side tabs and the barrier panel.

Figure 9A:
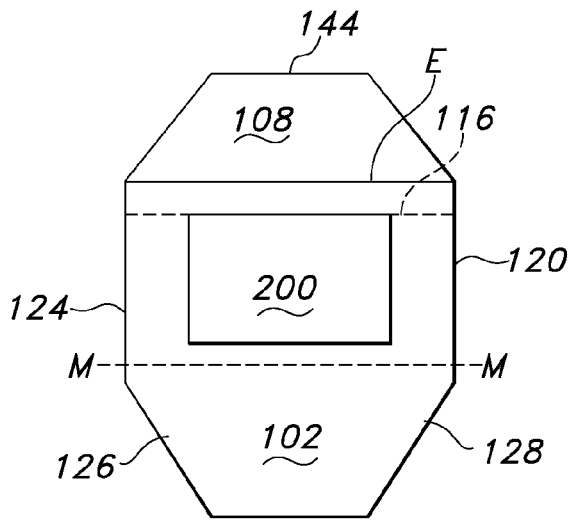
FIGS. 9A to 9G are illustrations of an exemplary sequence of folding an exemplary disposable flexible multi-panel sterilization assembly including side tabs and pull tabs having spaced apart pull locations.

Referring now to FIGS. 9A through 9G (and with additional reference to FIG. 8A), there is illustrated an example of a multi-panel sterilization assembly in an exemplary sequence of folding. FIG. 9A illustrates a multi-panel sterilization assembly 100 composed of barrier panel 102 which cooperates with the fold protection panel 108 and the panel attachment means 106 on the first surface 110 so the barrier panel 102 can be folded around the content 200 to form a package (such as the package 202 generally illustrated in FIGS. 9G and 10A). The barrier panel 102 is the portion of the flexible multi-panel sterilization assembly 100 that contacts and covers the content 202. The content 200 is placed in the content receiving 130.

Figure 9B:
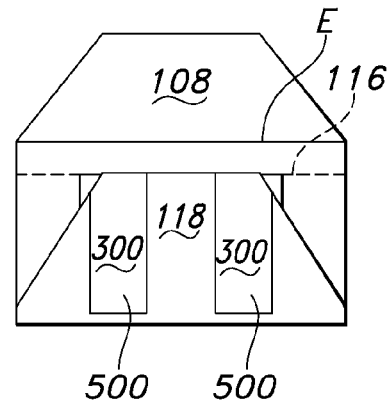

As generally illustrated in FIG. 9B, the second end 118 of the barrier panel 102 is folded up at the midpoint "M" and brought towards the first end 114 so the content covering region 132 of the barrier panel 102 extends over the content 200. As shown in FIG. 9B, the width of the barrier panel at the second end 118 is less than the width of the barrier panel at the first end 114. This is important when the panel attachment means 106 are located directly on the barrier panel (rather than being located on the side tabs 400) because it provides a configuration of the fourth edge 126 and the fifth edge 128 that allows access to the panel attachment means 106 after the second end 118 is brought up to the first end 114.

In some embodiments of the present invention, a pull tab system 300 and spaced apart pull locations 500 extend from the second end 118 so that the pull tab system 300 is positioned to be accessible during the final steps of unfolding or unwrapping a wrapped package. The pull tab system 300 desirably extends from or is joined to the second end 118 of the barrier panel on the second opposing surface 112 of the barrier panel 102. Referring briefly to FIG. 7D, there is shown a configuration in which the pull tab system 300 is a single tab that provides spaced apart pull locations 500. It is contemplated that the pull tab system 300 may be unitary or integral with the barrier panel. FIG. 7D also illustrates that pull tab system 300 is located on the second opposing surface 112 of the barrier panel 102. The distal end (i.e., the loose end) of the pull tab system 300 is desirably secured to the barrier panel with a light adhesive or an adhesive tab or sticker such that the pull tab system 300 does not flop around during wrapping and is in an appropriate position during unwrapping.

Figure 9C:
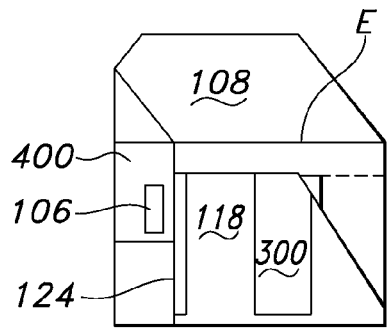

Referring now to FIG. 9C, that illustration shows that the third edge 124 of the barrier panel 102 is folded over the second end 118 (after the second end 118 is brought up to the first end 114). While not necessarily shown to scale, the third edge 124 of the barrier panel 102 after folding need not extend very far toward the middle of the assembly.

Figure 9D:
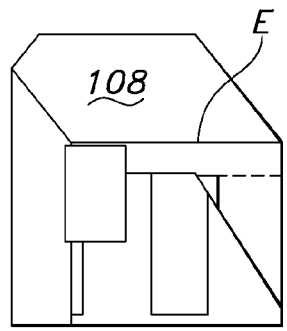
Figure 9E:
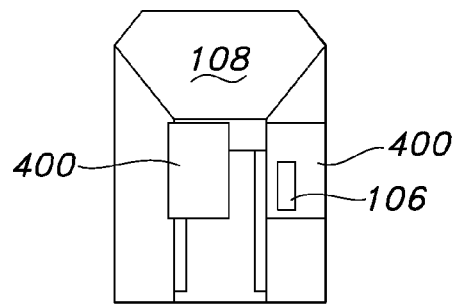

FIG. 9D illustrates that the side tab 400 on the third edge 124 is deployed so that the panel attachment means 106 is used to securely place the third edge against the second end 118 of the barrier panel (i.e., the content covering region). As can be seen in FIG. 9D, the panel attachment means 106 are positioned on the side tabs 400 so they attach to the second end 118 of the barrier panel (i.e., the content covering region) between the spaced apart pull locations 500 of the pull tab system 300. FIG. 9E illustrates that the first edge 120 of the barrier panel 102 is folded over the second end 118. While not necessarily shown to scale, the first edge 120 of the barrier panel 102 upon folding need not extend very far toward the middle of the assembly. Accordingly, it is evident that the third edge 124 and the first edge 120 generally do not overlap. Unlike conventional sterilization wrap in which the edges are intentionally overlapped as generally illustrated in FIGS. 4 and 5, the edges 120 and 124 of the barrier panel are separated by a distance. This difference highlights the importance of the panel attachment means 106 to hold the folded edges 120 and 124 of the barrier panel 102 in place about the content. Moreover, having these edges generally exposed highlights the importance of the fold protection panel 108.

Figure 9F:
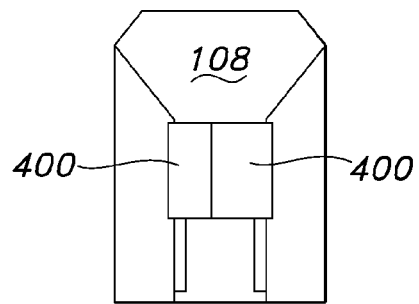
Figure 9G:
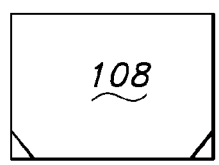

FIG. 9F illustrates that the side tab 400 on the first edge 120 is deployed so that the patent attachment means 106 is used to join this edge to the second end 118 of the barrier panel (i.e., the content covering region). As can be inferred from FIG. 9F, the panel attachment means 106 are positioned on the side tabs 400 so they attach to the second end 118 of the barrier panel (i.e., the content covering region) between the spaced apart pull locations 500 of the pull tab system 300.

Referring again to FIGS. 9D and 9F, the fold protection panel 108 and the portion of the barrier panel 102 between the extremity "E" at the first end 114 of the barrier panel and the pre-determined fold line 116 is folded over bringing the distal end 144 of the fold protection panel 108 over the second end 118 of the barrier panel. In some embodiments, a portion of the material adjacent the first edge 120 and the third edge 124 may be visible. With this configuration, the actual edges 120 and 124 of the barrier panel 102 are fully covered so the edges themselves are less susceptible to being accidently pulled open or breached during normal handling of the package. The fold protection panel is typically secured utilizing conventional tape that is used with sterilization wrap. Desirably, the fold protection panel covers the edges of the barrier protection panel after it is folded around the content to be sterilized to form a package. The fold protection panel covers these edges to prevent a worker inadvertently opening the folded barrier protection panel. In addition, the fold protection panel shields the edges from snags, pulls or other phenomenon that could impart a peel force to these edges that would cause the panel attachment means to detach. That is, the configuration of the multi-panel sterilization assembly utilizes the fold protection panel to protect exposed edges of the barrier panel after the barrier panel has been folded around content to be sterilized to form a package.

Figure 10A:
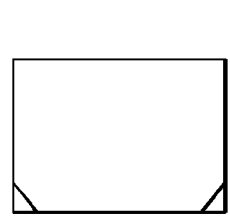
FIGS. 10A to 10D are illustrations of an exemplary sequence of unfolding an exemplary disposable flexible multi-panel sterilization assembly including side tabs and pull tabs having spaced apart pull locations.
Figure 10B:
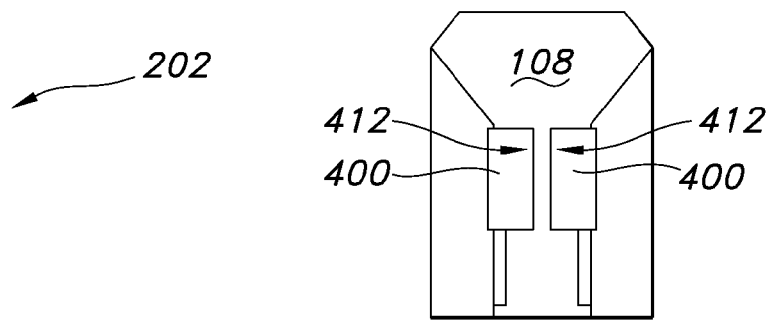
Figure 10C:
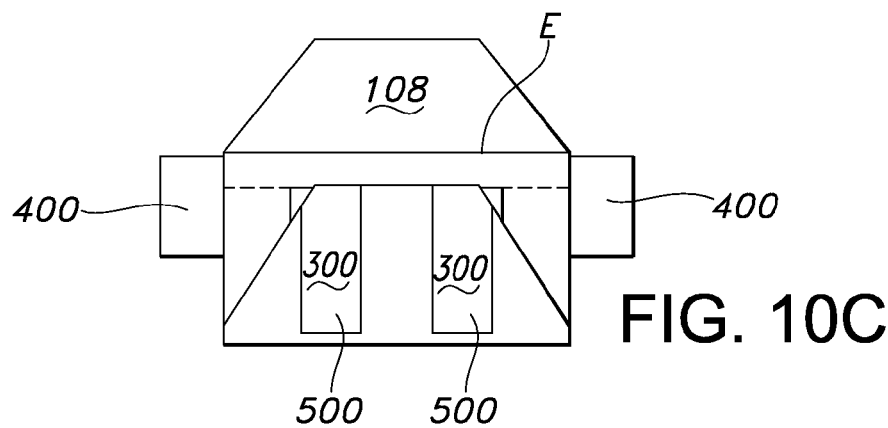
Figure 10D:
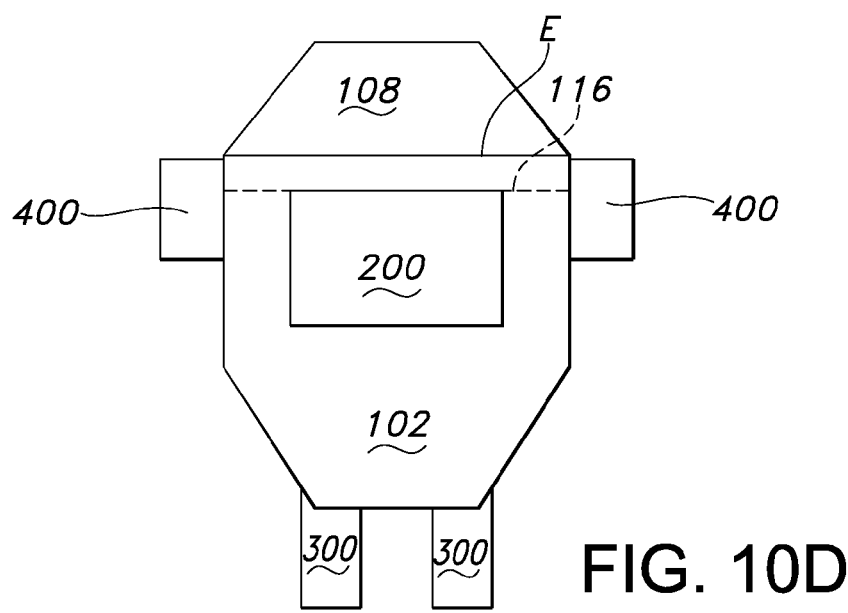

The sequence of unfolding the multi-panel sterilization assembly after it has wrapped around a tray or article and sterilized is generally the reverse of the folding sequence as generally illustrated in FIGS. 10A to 10D. For example, FIG. 10A illustrates a package 202 ready to be unwrapped or unfolded. A conventional tape securing the fold protection panel 108 is broken and the fold protection panel 108 is pulled back to expose the side tabs 400 as illustrated in FIG. 10B. The side tab distal end 412 (or other convenient portion) of each side tab may be grasped and the side tabs 400 may be pulled up and to the side (away from the center) to detach the panel attachment means such that the first edge 120 and the third edge 124 are unfolded to a configuration as generally illustrated by FIG. 10C. This step may be carried out by pulling the side tabs 400 simultaneously or sequentially. Importantly, the location/position of the side tabs 400, the weight of the side tabs (greater than 0.028 ounce), the ability to grip the side tabs without compromising sterility, and the leverage and distribution of forces provided by the extended side tabs help the fold protection panel, and the first edge 120 and the third edge 124 of the barrier panel remain in a generally flat, unfolded configuration which keeps them from folding back up over the content 200. FIG. 10D shows the sterilization assembly, side tabs and pull tabs completely unfolded and laying flat.

Referring briefly to FIG. 8C of the drawings, the configuration in which the panel attachment means 106 is located near the proximal tab end 402 provides a grip region "G" between panel attachment means 106 and the distal tab end 412. The distance between the distal tab end 412 and the panel attachment means may range from about ½ inch (e.g., a distance sufficient to avoid meaningful interference between a user's fingers and the panel attachment means) to a distance of up to about 6 inches or more. For example, the distance may be about ¾ inch to about 6 inches.

Of course, if the side tab 400 has a non-rectangular shape (e.g., is triangular or semi-circular, etc.), the position of the panel attachment means 106 from the distal end of the side tab will desirably provide a grip region. It is desirable that the panel attachment means 106 is positioned so that it is separated from the proximal tab end 402. For example, the panel attachment means 106 may be positioned so that it is separated from the proximal tab end 402 by a distance ranging from about ¼ inch up to 3 inches or more. During the sequence of unfolding the multi-panel sterilization assembly as illustrated at, for example, in FIGS. 10B and 10C, the separation distance is desirable because it generates disengagement of the panel attachment means from the barrier panel (or other component to which it is attached to keep the sterilization assembly in a folded configuration) prior to unfolding of the edges of the barrier panel.

These distances (i.e., to provide a grip region "G" and the separation between the panel attachment means 106 and the proximal tab end 402) singularly or in combination are also believed to help promote the opening of the multi-panel sterilization assembly (see, for example, FIGS. 10B and 10C) by a motion or orientation that provides primarily peel forces rather than shear forces to separate or disengage the panel attachment means 106. Such a configuration is advantageous because the peel force required to separate the panel attachment means is lower than the shear forces. When mechanical fastening systems such as, for example, hook and loop fasteners are used or when adhesive fastening systems are used in which the adhesive is applied directly to the barrier panel, such a configuration that promotes separation by peel force is thought to reduce the amount of broken fibers which may help reduce the possibility of contamination. The configuration also allows a user to disengage or separate the panel attachment means from the material to which it is attached before the edges of the package (e.g., the first edge 120 and the third edge 124) are unfolded to open the package. Furthermore, the configuration helps prevent a user from inserting a hand into the package under the edges (e.g., the first edge 120 and the third edge 124) to disengage the panel attachment means. The configuration illustrated in FIG. 8C also allows a user some freedom to manipulate the panel attachment means to increase engagement between the mechanical fasteners or adhesive and the material to which it is being attached to during folding—as well as to pull the material taut during folding.

As seen in FIG. 10C, unfolding the side tabs 400 exposes the spaced apart pull locations 500 of the pull tab system 300. Each pull location 500 is grasped at a convenient location or at the position when the pull tab system 300 is secured to the barrier panel with an adhesive tab or sticker and the tab or sticker is pulled up. The pull tab system 300 and the second end 118 of the barrier panel is pulled away from the content 200. The spaced apart pull locations 500 help the first edge 120 and the third edge 124 of the barrier panel remain in a generally flat, unfolded configuration which keeps them from folding back up over the content 200.

While the inventors should not be held to a particular theory of operation, it is believed that in addition the side tabs 400 having the tab width "TW" at the proximal tab end 402 that spans the indicia 116 to help the side tab 400 distribute forces during opening, the unfolded side tabs 400 shift the center of mass of each of the assembly portions 600, 602 by a sufficient amount to reliably prevent unfolded sides of the sterilization assembly from folding back up over the sterilized article or tray while other portions of the wrap are being unfolded. For example, in order for a user to unfold the second end 118 of the barrier panel 102 (after the first edge 120 and the third edge 124 have been unfolded by simultaneously or sequentially grasping and pulling the side tabs 400 up and to the side (away from the center) to detach the panel attachment means such that the first edge 120 and the third edge 124 are unfolded to a configuration as generally illustrated by FIG. 10C), the user must release the side tabs 400 in order to grasp the second end 118 of the barrier panel (or to grasp the pull tab 300 and its spaced apart pull locations 500 located at/on the second end 118). Each of the unfolded side tabs 400 (see FIG. 10C) shift the center of mass of each of assembly portion 600, 602 a sufficient amount away from the longitudinal axis "LA", respectively, to reliably prevent unfolded sides 120, 124 of the sterilization assembly from folding back up over the sterilized article or tray.

According to the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the barrier panel is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the sheet material of the barrier panel may range from 25 to about 500 cubic feet per minute (CFM) as characterized in terms of Frazier permeability. For example, the permeability of the sheet material barrier panel may range from 50 to about 400 cubic feet per minute. As yet another example, the permeability of the sheet material of the barrier panel may range from 100 to about 300 cubic feet per minute. Alternatively and/or additionally, the permeability of the barrier panel may range from 25 to about 500 cubic feet per minute (CFM) as characterized in terms of Frazier permeability. For example, the permeability of the barrier panel may range from 50 to about 400 cubic feet per minute. As yet another example, the permeability of the barrier panel may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A.

When the barrier panel is composed of or incorporates SMS material(s) that have basis weights ranging from about 1 osy (33 gsm) to about 2.6 osy (87 gsm), the permeability of the barrier panel may be lower than 25 cubic feet per minute. For example, when SMS materials having basis weights ranging from about 1 osy (33 gsm) to about 2.6 osy (87 gsm), the permeability of the barrier panel may range from about 20 cubic feet per minute to about 75 cubic feet per minute when determined generally in accordance with ISO 9237:1995 (measured with an automated air permeability machine using a 38 $cm^2$ head at a test pressure of 125 Pa—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

As noted above, the flexible multi-panel sterilization assembly 100 may include at least one pull tab system 300 extending from the second end 118 of the barrier panel 102. The pull tab system 300 may be formed of the same material as the barrier panel or may be formed of one or more different materials. The pull tab is a feature that can be grasped by a person to unfold the second end 118 without compromising the sterile field formed by the unfolded content-contacting portions of the barrier panel. The pull tab system 300 may be attached to the barrier panel or it may be integral or unitary with the barrier panel. In an aspect of the invention, the interface or transition of the barrier panel and the attached pull tab system 300 may be bonded or conditioned to result in a stiffening configuration. Such configurations may utilize a seam such as, for example, a stitched seam, an ultrasonic bond seam, adhesive bond seam, thermo-mechanical bond seam (e.g., a bar seal seam) thermal treatments, or combinations thereof to provide sufficient stiffness, rigidity or support to that portion of the barrier panel so that folding or creasing of the barrier panel is reduced or eliminated when force is applied to the pull tab system 300 during unwrapping. This is important to preserve the sterility of the contents during unwrapping. For example, the second edge 122 and the fourth edge 126 illustrated in FIG. 7B may be partially or substantially made to provide such a configuration. As another example, the second edge 122 illustrated in FIG. 8A may be partially or substantially bonded to provide the desired configuration. As yet another example, the second edge 122 and/or the fourth edge 126 and fifth edge 128 illustrated in FIG. 8A may be partially or substantially bonded to provide the desired configuration.

In an embodiment of the invention, the sterilization assembly may further include one or more discrete reinforcement elements in the content receiving region. In addition to reinforcing the barrier panel, the reinforcement element may define an area for receiving content to be sterilized. It is contemplated that the side tabs may extend into the content receiving region to reinforce the barrier panel and/or define an area for receiving content to be sterilized. Accordingly, the following discussion can be applied to the side tab if it is desired for that component to also serve as a reinforcement element in addition to providing a gripping region for the edges of the barrier panel during unfolding of the barrier panel. The reinforcement elements may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Nonwoven webs may include, for example, spunbond, meltblown, carded webs, wet formed or airlaid webs, or laminates of the same (e.g., spunbond/meltblown/spunbond). Such nonwoven webs may also include natural or synthetic materials or blends of the same. The reinforcement elements include one or more layers of material selected from permeable or impermeable films or laminates of the same. Permeable films may be apertured or be microporous. Apertured films may be obtained through mechanical aperturing, vacuum aperturing, or other commercially available techniques.

Reinforcement elements can be discrete zones of the barrier panel containing additional material or treatments to reduce the likelihood that the barrier panel will be compromised by pressure cuts, pressure holes, tears or the like in the locations where the content is likely to concentrate forces against the material(s) of the barrier panel. It is envisioned that relative to the material(s) of the barrier panel, the reinforcement elements can be less permeable or even impermeable to hot air, steam, or other sterilization gas, while still allowing for proper sterilization and removal of sterilant gas. It has been found that acceptable sterilization and removal of sterilant gas will take place if the permeability of the barrier panel is generally greater than about 25 cubic feet per minute (cfm) as characterized in terms of Frazier permeability. As such, a reinforcement element material that is impermeable or less permeable than the barrier panel is acceptable, as long as the barrier panel is adequately permeable (e.g., greater than about 10 cfm and more desirably greater than about 25 cfm).

The reinforcement elements may also be configured to identify the content receiving region 130 of the barrier panel 102. Alternatively and/or additionally the reinforcement elements may be configured to cooperate with the panel attachment means to identify the content receiving region 130 of the barrier panel 102. For example, the reinforcement elements may be in the form of discrete shapes placed within the content receiving region. FIGS. 11A through 11D are illustrations of exemplary flexible multi-panel sterilization assemblies 100 composed of a barrier panel 102 and a fold protection panel 108 and which further include reinforcement elements 302 (side tabs 400 and pull tab systems 300 not shown).

FIG. 11A illustrates a flexible multi-panel sterilization assembly 100 in which four reinforcement elements 302 are positioned at spaced apart locations in the content receiving region 130 of the barrier panel 102 generally at the locations that correspond to the corners of a sterilization tray or similar content. FIG. 11B illustrates a flexible multi-panel sterilization assembly 100 in which two reinforcement elements 302 are positioned at spaced apart locations on the barrier panel 102 extending from the pre-determined fold line 116 to a fourth edge 126 and a fifth edge 128 of the barrier panel 102 generally opposite the pre-determined fold line 116. The two reinforcement elements 302 are positioned in the content receiving region 130 generally at the locations that correspond to the corners of a sterilization tray or similar content. FIG. 11C illustrates a flexible multi-panel sterilization assembly 100 in which two reinforcement elements 302 are positioned at spaced apart locations on the barrier panel 102 generally parallel to the pre-determined fold line 116 between the two panel attachment means 106 at or adjacent a first edge 120 and a third edge 124. The two reinforcement elements 302 are positioned in the content receiving region 130 generally at the locations that correspond to the corners of a sterilization tray or similar content. It is contemplated that the reinforcement elements 302 may extend beyond the edges of the barrier panel and that the extended portion of the reinforcement elements 302 may serve or function as the pull tab system 300. For example, the extended portion may be folded back onto the second opposed side 112 of the barrier panel 102 (see, for example, FIGS. 7C and 8B).

FIG. 11D illustrates a flexible multi-panel sterilization assembly 100 in which two reinforcement elements 302 are positioned at spaced apart locations on the barrier panel 102 and the fold protection panel 108. The two reinforcement elements 302 extend in generally parallel configuration from a distal end 144 of the fold protection panel 108 to a fourth edge 126 and a fifth edge 128 of the barrier panel 102. The two reinforcement elements 302 are positioned in the content receiving region 130 generally at the locations that correspond to the corners of a sterilization tray or similar content.

Of course, the reinforcement elements may have a wide variety of shapes, sizes and other configurations. FIGS. 12A and 12B are illustrations of exemplary reinforcement elements 302. FIG. 12A illustrates reinforcement elements 302 having generally triangular configurations. FIG. 12B illustrates an exemplary reinforcement element 302 composed of several overlapping triangular elements. Alternatively and/or additionally, the reinforcement element 302 illustrated in FIG. 12B may be formed by a single piece of material. Other shapes and configurations are contemplated such, for example, "H" patterns, "X" patterns, or the like.

Figure 13:
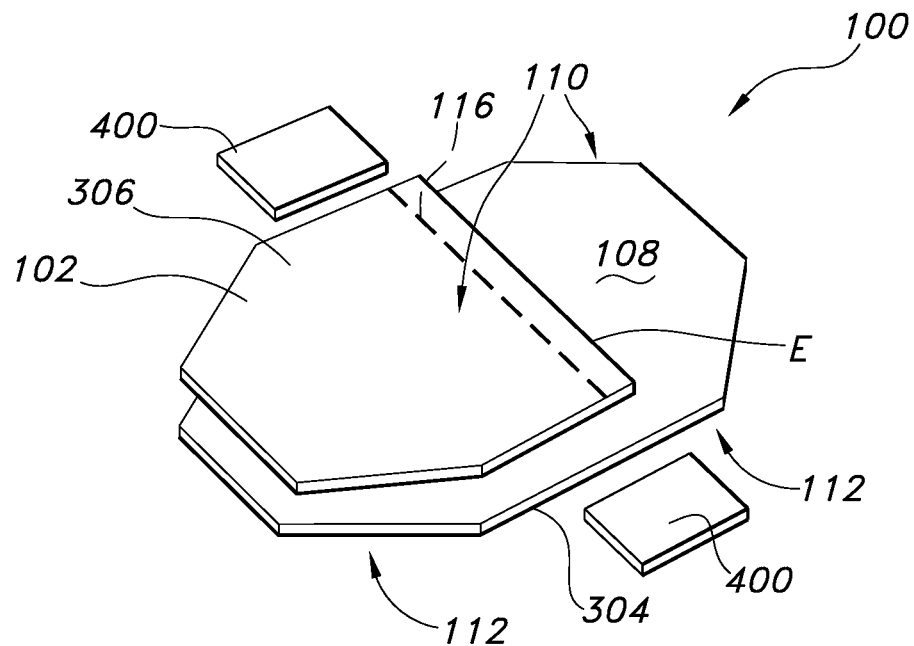
FIG. 13 is an illustration of an exploded or broken apart perspective view of exemplary features of an exemplary flexible multi-panel sterilization assembly.

In an embodiment of the invention, the construction of the disposable flexible multi-panel sterilization assembly may be based on two primary pieces of material. Referring now to FIG. 13, there is shown an illustration of an exemplary disposable flexible multi-panel sterilization assembly 100 in exploded or broken apart view revealing a first piece (layer) 304 of a material and a second piece (layer) 306 of material. In this configuration, the material overlap of the first layer 304 and the second layer 306 to define the barrier panel 102. Generally speaking, these layers may be joined by adhesives, ultrasonic bonding, thermo-mechanical bonding or the like. The layers are desirably joined at or adjacent at least two of the edges and along the second end. For example, the layers may be joined along the first edge 120 and the third edge 124. The bonding may be a complete seam or the edge may be partially bonded along only one or a few portions of the edge. Alternatively and/or additionally, the bonding may be intermittent or discontinuous along all or a portion of the respective edge. Of course, other edges may also be bonded or the layers may be bonded together across all or portions of their entire surface area. The region where there is no overlap of the first layer 304 of material and second layer 306 of material forms the fold protection panel 108. Generally speaking, the first layer 304 of material and the second layer 306 of material may be the same material or they may be different materials. For example, the first layer 304 of material may be single layer or multiple layers of spunbond nonwoven material, a lightweight nonwoven laminate material, or a material that lacks the level of barrier properties (or other characteristics) that may be desired for the barrier panel. The second layer 306 of material desirably has a higher level of barrier properties than the first layer 304 of material. For example, the second layer 306 of material may be a laminate of nonwoven fabrics such as "SMS" material. The second layer 306 of material may have a different color and/or pattern than the first layer 304 of material. For example, the first layer 304 of material may have a first color (e.g., a blue color), a dark color, or a specific color on a color scale and the second layer 306 of material may have no color (e.g., white), a second color (e.g., a light color), or a specific color on a color scale that contrasts with the first color. It is contemplated that the color differentiation or contrast between the first layer 304 of material and the second layer 306 of material may be useful to function as an indicator that barrier properties of the barrier panel may be compromised.

Figure 14:
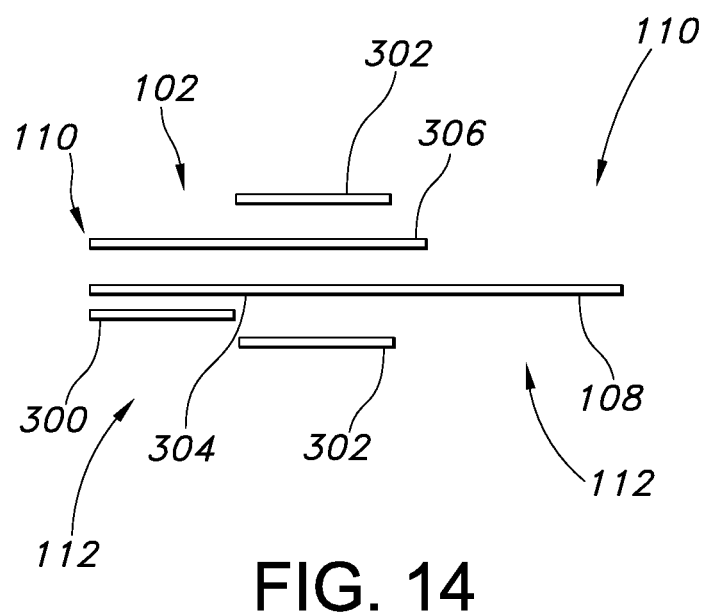
FIG. 14 is an illustration of an exploded or broken apart cross-section view of exemplary features of an exemplary flexible multi-panel sterilization assembly.

Referring now to FIG. 14, there is shown an illustration of an exemplary disposable flexible multi-panel sterilization assembly 100 (side tabs 400 not shown) in exploded or broken apart cross-sectional view revealing a first layer 304 of a material and a second layer 306 of material. In this configuration, the first layer 304 of material and the second layer 306 of material overlap to define the barrier panel 102. The region where there is no overlap of the first layer 304 of material and second layer 306 of material forms the fold protection panel 108. The cross-sectional view illustrates reinforcement elements 302 which may be located directly on the second layer 306 of material. The reinforcement elements 302 may be present on the first surface 110 to desirably identify the content receiving region 130 of the barrier panel 102. Alternatively and/or additionally, the reinforcement elements 302 may be located on the second opposing surface 112 of the barrier panel.

Sterilization wrap has many modes of failure involving tears, cuts, punctures, holes or other breaches. Any failures may have serious consequences. The more common modes of failure are conventionally believed to involve tears, holes or cuts initiating from the sterilization tray or other content that is wrapped by or otherwise enclosed by conventional sterilization wrap fabric. In other words, tears, cuts or holds were believed to begin at the interface between the sterilization tray or other content and the sterilization wrap fabric itself and propagate from the inside of the sterilization wrap fabric penetrating outwardly through the material ultimately creating a breach. Accordingly, much effort has been expended to develop corner guards and other types of protection that is placed between the sterilization tray or other content and the sterilization wrap.

In an aspect of the present invention, it has been discovered that pressure holes and pressure cuts of the type in which the fibers adjacent the hole or cut appear to have been fused or "welded" together most commonly propagate from the outside of a package (i.e., content enclosed by sterilization wrap fabric) rather than propagating the sterilization tray or other content that is wrapped by or otherwise enclosed by conventional sterilization wrap fabric. Desirable embodiments of sterilization assemblies locate the reinforcement elements 302 on the second opposing surface 112 of the barrier panel to provide an additional unexpected advantage because the second opposing surface 112 of the barrier panel 102 is the portion of the disposable flexible multi-panel sterilization assembly 100 that does not contact the content (e.g., sterilization tray) and which typically forms the outside of a wrapped package. Reinforcement elements 302 located on the second opposing surface 112 are thought to provide more efficient protection against pressure holes and pressure cuts because pressure holes and pressure cuts tend to propagate from the outside of a wrapped package. While the inventors should not be held to any particular theory of operation, it is believed that pressure cuts and pressure holes are more frequently caused when content enclosed by sterilization wrap contacts an irregular surface with sufficient force during a single contact event or during multiple contact events such that the irregular surface concentrates the force to generate energy that causes failure.

EXAMPLES

Aspects of the flexible multi-panel sterilization assembly with mass-balancing side tabs were evaluated in the following examples.

Exemplary flexible multi-panel sterilization assemblies were constructed to have eight (8) sides or edges. This geometry is generally as illustrated in FIGS. 8A-D; 9A-G and 10 A-D, except that the sterilization assemblies did not include pull tabs 300. That is, the sterilization assemblies were composed of a barrier panel 102, a fold protection panel 108, side tabs 400, reinforcement elements 302 and panel attachment means 106 located on the side tabs 400 as generally illustrated in these figures and as shown in FIGS. 15-19.

Each assembly of the invention has a bisecting longitudinal axis "LA" (sometimes referred to as a "bisecting axis of symmetry") and a barrier panel 102 with a defined second end 118. The intersection of the longitudinal axis "LA" and the second end 118 of the barrier panel of an unfolded assembly is arbitrarily chosen as the reference origin (x=0; y=0) in the following examples. (Other references origins are possible and assumed to be valid for determining the center of mass shifts; however the relative magnitudes of the shifts may differ from the following examples but the findings should translate once differences in origins are accounted for.)

Examples that typify the invention are given with dimensions according to Sizes 1, 3, 5, 7, 8, 4, 1A, 3A per Table A and are made from nonwoven fabrics of relatively uniform basis weights per combinations identified as 250, 450, 550, 650 per Table B; these examples are subsequently described.

Each example can be associated with a center of mass that corresponds to the first and/or second portion of the assembly and with centers of mass that correspond to any attached components. One way to determine these centers of mass separates them into rectangular, triangular, and semi-circular shapes as is illustrated in FIGS. 15-19.

In describing the determination details, the first or second portion 600, 602 to the right or left of the bisecting axis of symmetry "LA" of each assembly version (they are interchangeable) is referred as the assembly portion and both portions together are referred as the assembly. An origin point "O" is designated at the intersection of the axis of symmetry "LA" that bisects the assembly into equal halves and the extreme limit of the second end 118 of the barrier panel. (This origin is depicted in the figures as a circle around a cross.) The location of the center of mass is expressed via "x" coordinates in the X direction and "y" coordinates in the Y direction as shown in FIG. 18 with respect to this origin. These X and Y directions respectively coincide with the arrows identifying the CD and MD directions in FIGS. 15-19.

The perpendicular distances away from the bisecting axis of symmetry "LA" define x coordinates, the distances from the extremity (e.g., the second edge 122) of the second end 118 along the bisecting axis of symmetry "LA" define y coordinates. Respective center of mass locations are first calculated for each separated shape, then are combined via weighted averaging conventions to determine the centers of mass for the assembly, the assembly with panel attachment means, with the side tabs, and their combinations. Such combined or total center of mass determinations, with and without side tabs, distinguish embodiments of the invention from comparative examples.

The following steps give one method for center of mass determination via dimensions for the Size 5 assembly example and its related additional component elements. The steps of this method were used for determining the values given in Tables A-F. Other methods are possible, i.e. separation of the assemblies and components into different shapes and orientations from those described for the following Size 5 examples; selection of a different origin. (Changes in specific shapes and orientations with respect to the origin as described above will yield equivalent results; selection of a different origin will give different coordinates for the center of mass, yet the difference in the coordinates of the assembly with and without additional component elements will be consistently proportional if not the same.)

Figure 16B:
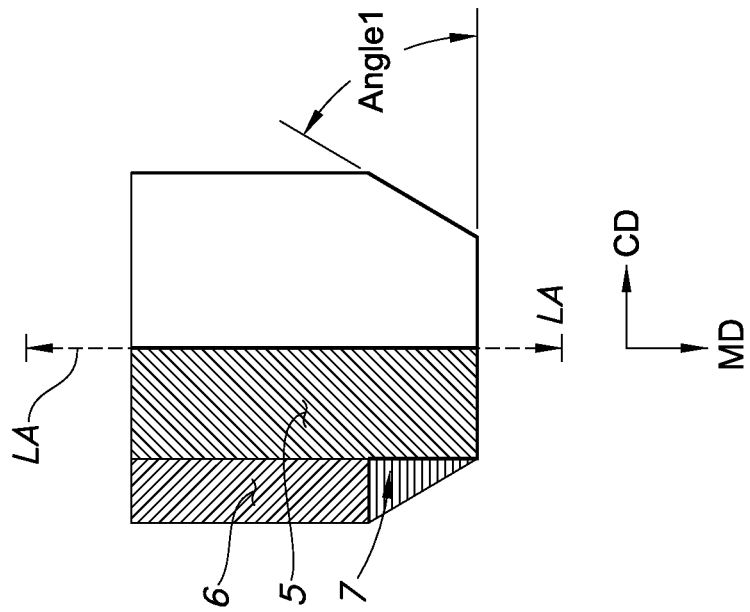
FIGS. 16A and 16B are illustrations of a top view showing a detail of a specific region of a portion of an exemplary assembly for determining center of mass values.
Figure 16A:
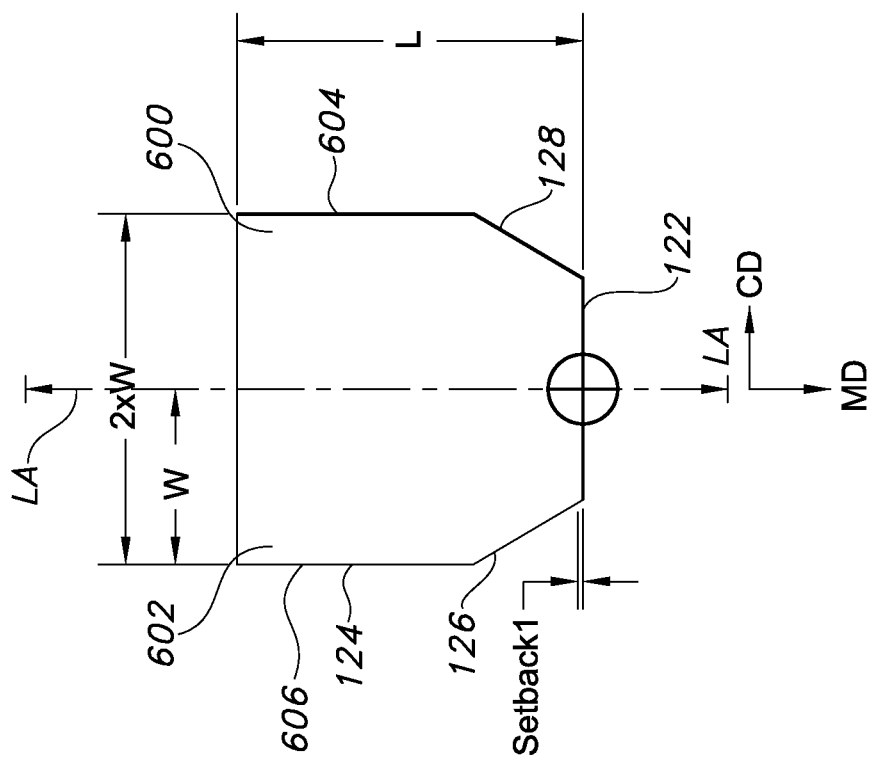
Figure 17B:
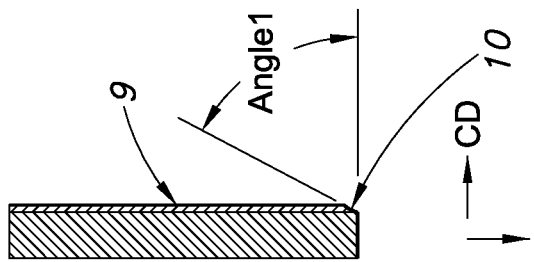
FIGS. 17A and 17B are illustrations of a top view showing a detail of an exemplary reinforcement element of an exemplary assembly for determining center of mass values.
Figure 17A:
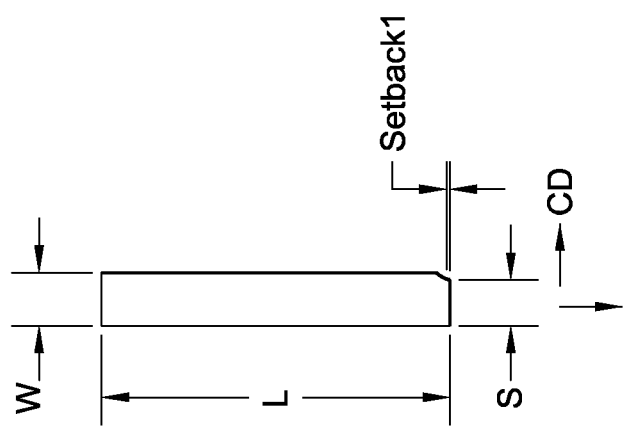
Figure 18:
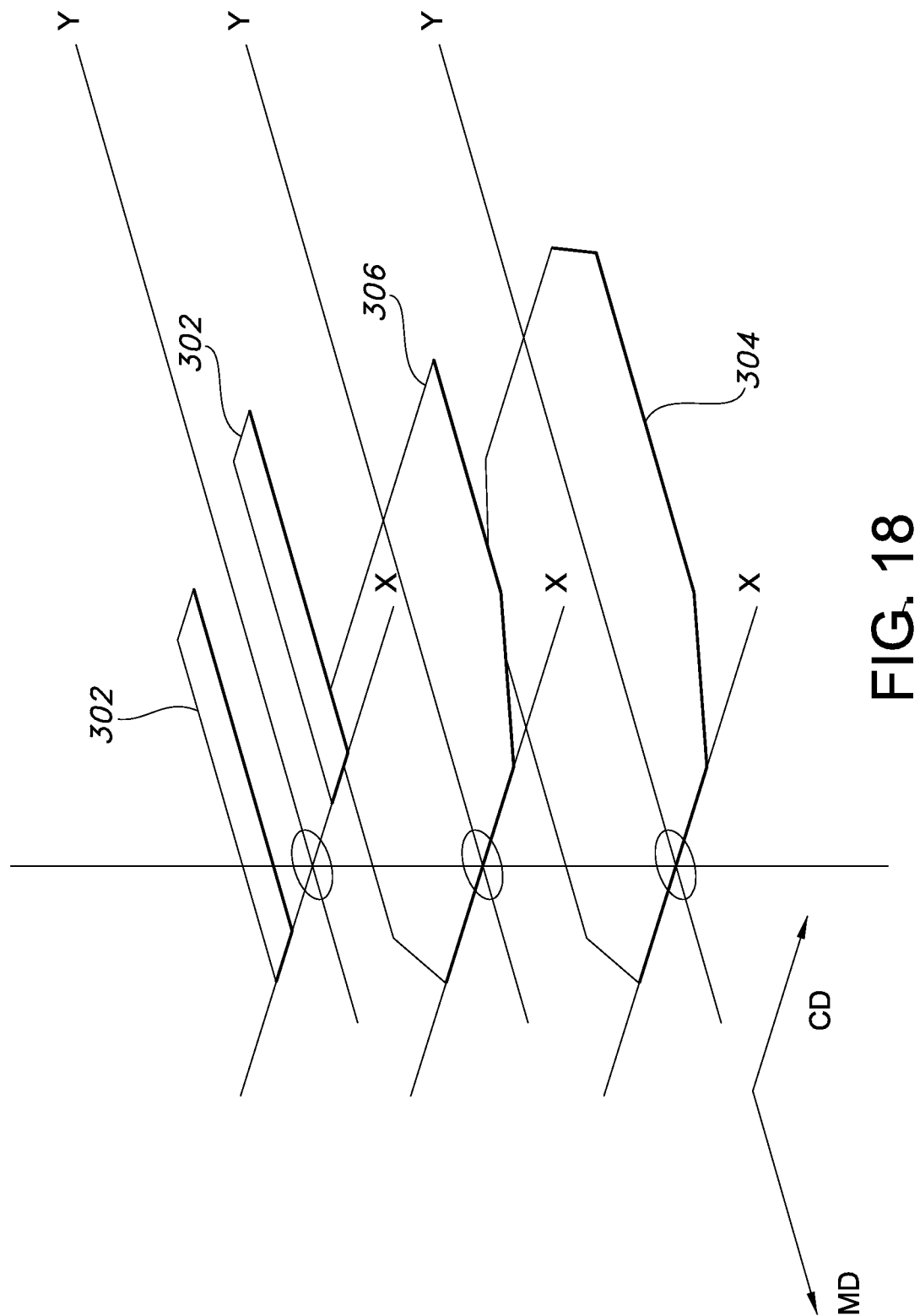
FIG. 18 is an illustration of an exploded or broken apart perspective view of exemplary features of an exemplary flexible multi-panel sterilization assembly and added reinforcement elements for determining center of mass values.
Figure 19:
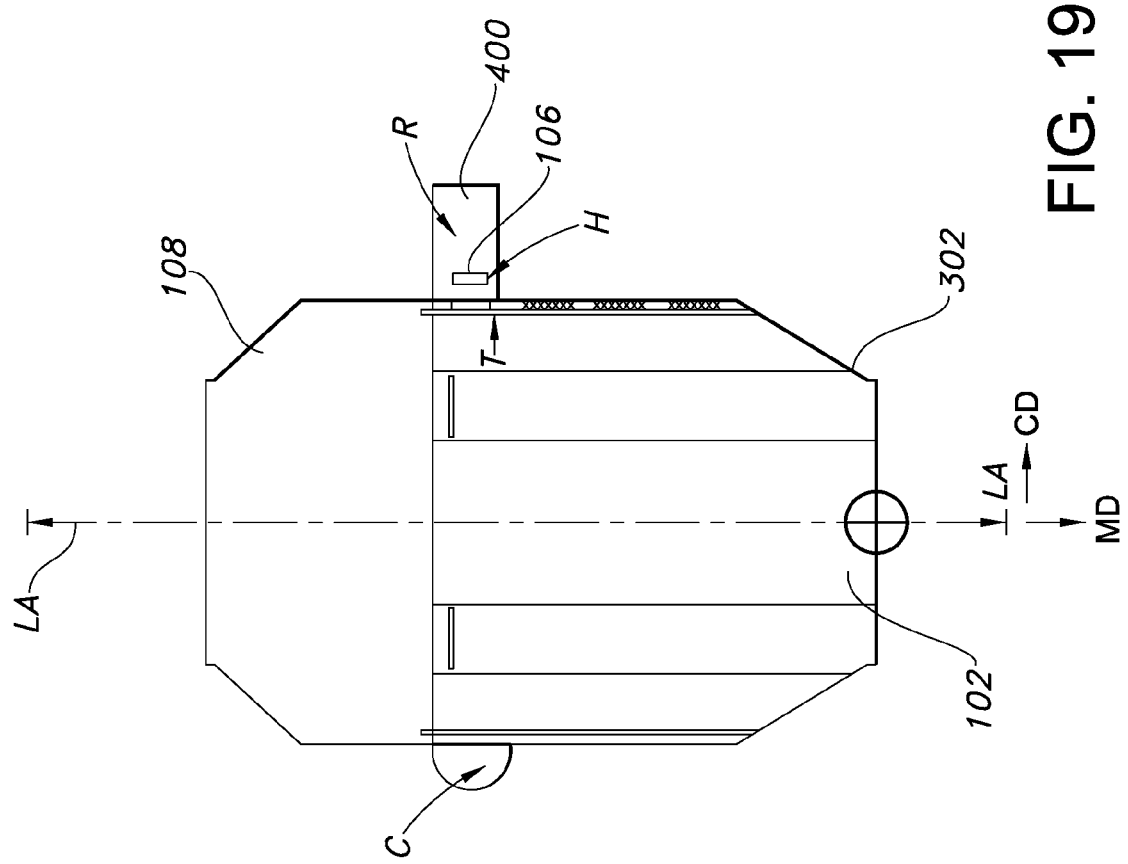
FIG. 19 is an illustration of a top view showing regions and areas of an exemplary assembly and added components for determining center of mass values.

For determination of the center of mass for each Size example with and without various component elements, first steps divide the assembly portion into: a "Base" as shown in FIG. 15, which consists of the fold protection panel and part of the barrier panel to one side of the bisecting axis of symmetry; an "Intermediate" as shown in FIG. 16, which consists of the rest of the barrier panel to one side of the bisecting axis of symmetry; one of the two symmetrically placed "Reinforcements" on each side of the bisecting axis of symmetry, one of which is shown in FIG. 17; and, as shown in FIG. 19, additional component elements of adhesive patch, hook arrays, semi-circular side tabs, and rectangular side tabs. (Specifics on these additional component elements are subsequently given and described.) The positional relationships of the base, intermediate and reinforcements are illustrated in FIG. 18 where each "division" (i.e. Base, Intermediate, and Reinforcement) is spatially associated with the bisecting axis of symmetry (in the Y direction), the second end of the barrier panel (in the X direction) and the origin. Each division has a maximum dimension W in the X direction, and a maximum dimension L in the Y direction as shown in FIGS. 15-17. Each Size example has its own set of W and L values.

Next, each division is separated into rectangular, triangular, and semi-circular shapes as appropriate. As indicated in FIG. 15 the Base is separated into two rectangular shapes denoted as 1 and 2, and two triangular shapes denoted as 3 and 4—the triangle shapes are right triangles. Similarly, as indicated in FIG. 16, the Intermediate is separated into two rectangular shapes denoted as 5 and 6 and one triangular shape, also a right triangle, denoted as 7, and as indicated in FIG. 17 one Reinforcement is separated into two rectangular shapes denoted as 8 and 9 and one triangular shape, also a right triangle, denoted as 10. And as indicated in FIG. 19, the adhesive patch, hook array, and rectangular side tab to one side of the bisecting axis of symmetry are represented as rectangles T, H, and W respectively; and semi-circular side tab is represented as the semi-circle C. Table J lists the dimensions for the Size 1, 3, 5, 7, 8, 4, 1A and 3A examples that correspond to the notations given on Figures A-C.

TABLE A

| Dimensions | | Size | | | | | | | |
|---|---|---|---|---|---|---|---|---|---|
| | | 1 | 3 | 5 | 7 | 8 | 4 | 1A | 3A |
| Base | L, inches | 45.25 | 53 | 54.5 | 39.75 | 44.25 | 45.25 | 47.25 | 55 |
| | W, inches | 20 | 20 | 18 | 16 | 11 | 14 | 20 | 20 |
| | Setback 1, inches | 0.5 | 0.5 | 0.5 | 0.5 | 0.5 | 0.5 | 0.5 | 0.5 |
| | Setback 2, inches | 0.5 | 0.5 | 0.5 | 0.5 | 0.5 | 0.5 | 0.5 | 0.5 |
| | Angle 1 | 53 | 59 | 59 | 45 | 55 | 63 | 53 | 59 |
| | Angle 2 | 32 | 47 | 47 | 42 | 51 | 54 | 32 | 47 |
| Intermediate | L, inches | 29.75 | 34.5 | 35.75 | 26.5 | 29.5 | 30.25 | 36.75 | 44.5 |
| | W, inches | 20 | 20 | 18 | 16 | 11 | 14 | 20 | 20 |
| | Setback 1, inches | 0.25 | 0.25 | 0.5 | 0.25 | 0.25 | 0.25 | 0.25 | 0.25 |
| | Angle 1 | 53 | 59 | 59 | 45 | 55 | 63 | 59 | 59 |
| Cut-Out, inches | | 11.5 | 11.5 | 11.5 | 11.25 | 6.125 | 8.5 | 11.5 | 11.5 |
| Reinforcement | L, inches | 29.75 | 34.5 | 35.75 | 26.5 | 29.5 | 30.25 | 36.25 | 44.5 |
| | W, inches | 5.5 | 5.5 | 5.5 | 5.5 | 5.5 | 5.5 | 5.5 | 5.5 |
| | Setback 1, inches | 0.25 | 0.25 | 0.25 | 0.25 | 0.25 | 0.25 | 0.25 | 0.25 |
| | Angle 1 | 53 | 59 | 59 | 45 | 55 | 63 | 59 | 59 |
| | S, inches | 3.5 | 3.88 | 4.88 | 4.38 | 4.25 | 3.25 | 3.88 | 3.88 |
| Separated Shape, square inches | 1 | 520.4 | 609.5 | 626.8 | 447.2 | 271.0 | 384.6 | 543.4 | 632.5 |
| | 2 | 235.1 | 244.3 | 232.1 | 141.2 | 147.8 | 125.3 | 252.1 | 632.5 |
| | 3 | 35.2 | 60.1 | 35.2 | 11.3 | 16.9 | 33.3 | 46.0 | 261.3 |
| | 4 | 22.6 | 38.7 | 22.7 | 10.2 | 14.7 | 25.7 | 22.6 | 60.1 |
| | 5 | 342.1 | 396.8 | 257.1 | 298.1 | 180.7 | 257.1 | 422.6 | 511.8 |
| | 6 | 154.9 | 170.9 | 98.4 | 102.1 | 108.8 | 98.4 | 214.4 | 255.9 |
| | 7 | 47.9 | 60.1 | 33.3 | 11.3 | 16.9 | 33.3 | 47.9 | 60.1 |
| | 8 | 104.1 | 133.9 | 174.5 | 116.1 | 373.6 | 98.3 | 128.6 | 17.5 |
| | 9 | 53.7 | 51.1 | 21.4 | 28.1 | 45.8 | 56.3 | 67.7 | 67.3 |
| | 10 | 0.3 | 2.2 | 0.3 | 0.6 | 0.7 | 5.6 | 0.3 | 2.2 |
| Rectangular Tab R | | | | | | | | | |
| | L, inches | 5.5 | 5.5 | 5.5 | 5.5 | 5.5 | 5.5 | 5.5 | 5.5 |
| | W, inches | 8.5 | 8.5 | 8.5 | 8.5 | 8.5 | 8.5 | 8.5 | 8.5 |
| Semi-circular tab C | | | | | | | | | |
| | L, inches | 6 | 6 | 6 | 6 | 6 | 6 | 6 | 6 |
| | W, inches | 3 | 3 | 3 | 3 | 3 | 3 | 3 | 3 |

Details of the determination steps follow using the dimensions of the Size 5 example (as given in Table A and shown in FIGS. 15-19).

The Base, as shown in FIG. 15, has a maximum length distance L of 54.5 inches, a maximum width distance W of 18 inches on each side of the bisecting axis of symmetry, and generally triangular cut-outs from the barrier panel and the fold protection panel ends (from the second end and distal end respectively) with those cut outs stepped back from the extremity of these respective ends per Setback 1 and 2 of 0.5 inches. The barrier panel cut-outs form Angle 1 of 59 degrees with respect to the second end's extremity and form a Cut-Out distance in the X direction at this extremity of 11.5 inches. In a similar manner, the fold protection panel cut-outs form Angle 2 of 47 degrees with respect to that end's extremity and also form the Cut-Out distance of 11.5 inches at this extremity. The rectangle 1 has a square inch area of 11.5*54.5. The triangular area 3 has a square inch area of 0.5*(18−11.5)*[(18−11.5)*sin 59/sin 31] where (18−11.5) represents the leg of the right triangle in the X direction and the bracketed terms [(18−11.5)*sin 59/sin 31] represents the other leg of the right triangle in the Y direction per trigonometric equation relationships that are known as the law of sines. The bracketed terms equate to 10.817816. The triangular area 4 has a square inch area of 0.5*(18−11.5)*[(18.5−11.5)*sin 47/sin 43] where these terms in parentheses and brackets similarly represent the legs of the right triangle, and the bracketed terms equate to 6.9703966. The rectangle area 2 has a square inch area of (54.5−6.9703966−10.817816−0.5−0.5)*(18−11.5).

The Intermediate, as show in FIG. 16, has a maximum length L of 35.75 inches, a maximum width W of 18 inches on each side of the bisecting axis of symmetry and generally triangular cut-outs from the barrier panel end (the second end) with those cut-outs stepped back 0.5 inches from the extremity of this end (for Setback 1). The barrier panel cut-outs form the same Angle 1 and the Cut-Out distance at this extremity as those of the base. The rectangle 5 has a square inch area of 11.5*35.75. The triangular shape 7 has a square inch area and leg dimensions that are the same as the right triangle denoted as 3 of the base. The rectangle 6 has a square inch area of (18−11.5)*(35.75−0.5−10.817816).

The Reinforcement, as shown in FIG. 17, has a maximum length L of 35.75 inches, a maximum width W of 5.5 inches and a triangular cut-out from the end nearest the barrier panel end (the second end) with that cut out stepped back 0.25 inches from the extremity of this end (for Setback 1). The cut-out for the Reinforcement forms the same Angle 1 at this extremity as those of the Base and Intermediate. The cut-out is aligned with the corresponding base and intermediate cut-outs at the Cut-Out distance and has a dimension at the second end S of 4.88. The rectangle 8 has a square inch area of 35.75*4.88. The triangular shape 10 has a square inch area of 0.5*(5.5−4.88)*[(5.5−4.88)*sin 59/sin 31] where these terms in parentheses and brackets represent the legs of the right triangle 10 and the bracketed terms equate to 1.0318533. The rectangle 9 has a square inch area of (35.75−0.25−1.0318533)*(5.5−4.88).

The additional component elements of adhesive patch T, hook array H, rectangular side tab R, semi-circular side tab C are shown in FIG. 19 along with their possible placements with respect to the base, intermediate and reinforcement to one side of the axis of symmetry. In general the additional component elements are likely to be placed on or near the assembly as pairs, e.g. two identical rectangular side tabs with one placed on each side of the axis of symmetry, rather than the illustration shown. Rectangular side tabs or semi-circular side tabs on both sides of the axis of symmetry are certainly embodiments of the invention and comparative examples. FIG. 19 shows one rectangular side tab R to one side of the bisecting axis of symmetry and a semi-circular side tab C to the other side. When including the rectangular or semi-circular side tabs with the assembly, they are located at the side edges between the midpoint and the first end of the barrier panel. Likewise the placement of adhesive patch T and hook array H in FIG. 19 is for illustrative purposes only and has no restrictions per se on embodiments of the invention and comparative examples. In FIG. 19 only one adhesive patch T and one hook array H are shown to one side of the bisecting axis of symmetry; such elements on both sides of the bisecting axis of symmetry are certainly among embodiments of the invention and comparative examples.

In FIG. 19 one edge of the side tabs is aligned to one side of the pre-determined fold line with the rest of the tab extending beyond the other side of the pre-determined fold line in the Y direction towards the midpoint of the barrier panel. This ensures that the side tab is effective in playing a contributing role in aseptic opening. The rectangular side tab R has a length dimension L of 5.5 inches and a width dimension W of 8.5 inches, thus it has a square inch area of 5.5×8.5. The semi-circular tab C has a diameter of 6 inches with this the L dimension and half this (6/2) the W dimension, and it has a square inch area of $0.5*\pi*(6/2)^2$. Preferred distances in the Y direction for the edge of the side tab R that is farthest from the midpoint (and the second end of the barrier panel) have been found to be ~0.5–3 inches away from the pre-determined fold line. In the Size examples, the distance in the Y-Direction for the farthest edge of tab R and the pre-determined fold line is 1.5 inches.

Adhesive patch T and hook array H are examples of panel attachment means. As shown in FIG. 19 both are aligned to start near the predetermined fold line and extend in a Y direction towards the midpoint of the barrier panel. The exemplary dimensions for both the adhesive patch T and hook array H have 1 inch width (X direction) and 4 inch length (Y direction) for a square inch area of 1*4. The adhesive patch T is shown near one side edge of the barrier panel; the hook array H is shown on the rectangular side tab R (these are illustrative placements only; placement of adhesive patch T and hook array H is possible in other orientations and configurations as well as on other side tabs). Each of the separated shapes and side tabs per the FIGS. 15, 16, 17 and 19 is made from nonwoven fabrics that are fairly uniform with respect to weight and thickness distribution. The Base, Intermediate, Reinforcement and side tabs have basis weights selected from these ounces per square yard (osy) values: 1.05, 1.20, 1.40, 1.85, 2.05, or 2.57. Various combinations of assemblies from among these basis weight fabrics are used for the Size examples of Table A and each combination is identified as 250, 450, 550, and 650 per Table B. Of course, basis weights between these values are also candidates for use in the invention and comparative examples. The 1 inch by 4 inch adhesive patch T has an attached weight of ~0.33 grams (without any removable protective covering). The 1 inch by 4 inch hook array has an attached weight of ~0.52 grams.

For calculating center of mass values these conversion factors were used: 1 square inch=0.0007716049327 square yard; 1 ounce=28.3495231 grams.

TABLE B

|  | Basis Weight Combinations | | | |
| --- | --- | --- | --- | --- |
|  | 250 | 450 | 550 | 650 |
| Base, osy | 1.2 | 1.85 | 2.05 | 2.57 |
| Intermediate, osy | 1.05 | 1.2 | 1.4 | 1.85 |
| Reinforcement, osy | 1.2 | 1.85 | 2.57 | 2.57 |
| Rectangular Tab, osy | 1.2 | 1.85 | 2.57 | 2.57 |
| Semi-circular tab, osy | 2.57 | 2.57 | 2.57 | 2.57 |

Using the preceding separated shapes, their respective center of mass locations, expressed as x and y coordinates from the indicated origin, were determined via these shape-related relationships: for each rectangle, its center; for each triangle, one-third of the distance out from the right angle along both legs (sides); for the semi-circle, with the orientation as shown in FIG. 19, $4/3\pi$ times the radius of the semi-circle for the x coordinate and half the distance of the diameter for the y coordinate. Determining such separated center of mass locations as x and y coordinates for all the Size examples in inches are done in the following manner and are listed in Table C.

TABLE C (in two sections)

| | | Size: 1 | | Size: 3 | | Size: 5 | | Size: 7 | |
|---|---|---|---|---|---|---|---|---|---|
| | | Ctr of mass coordinates, Inches: | | | | | | | |
| | | x | y | x | y | x | y | x | y |
| Separated | 1 | 5.75 | 22.63 | 5.75 | 26.50 | 5.75 | 27.25 | 5.63 | 19.88 |
| Shapes per | 2 | 15.75 | 25.61 | 15.75 | 29.02 | 14.75 | 29.17 | 13.63 | 20.11 |
| FIG. A-C | 3 | 14.33 | 8.02 | 14.33 | 9.93 | 13.67 | 7.71 | 12.83 | 3.67 |
| | 4 | 14.33 | 41.21 | 14.33 | 46.42 | 13.67 | 49.35 | 12.83 | 36.40 |
| | 5 | 5.75 | 14.88 | 5.75 | 17.25 | 5.75 | 17.88 | 5.63 | 13.25 |
| | 6 | 15.75 | 20.64 | 15.75 | 24.45 | 14.75 | 23.53 | 13.63 | 15.75 |
| | 7 | 14.33 | 7.77 | 14.33 | 9.68 | 13.67 | 7.71 | 12.83 | 3.42 |
| | 8 | 9.75 | 14.88 | 9.56 | 17.25 | 9.06 | 17.88 | 9.06 | 13.25 |
| | 9 | 12.50 | 16.33 | 12.31 | 18.72 | 11.81 | 18.52 | 11.81 | 13.94 |
| | 10 | 12.17 | 2.02 | 12.04 | 2.05 | 11.71 | 0.94 | 11.62 | 1.00 |
| Tab R | | 24.25 | 27.00 | 24.25 | 31.75 | 22.25 | 33.00 | 20.25 | 23.75 |
| Patch T at edge | | 19.50 | 26.75 | 19.50 | 31.00 | 17.50 | 32.75 | 15.50 | 23.00 |
| Tab C | | 21.27 | 26.75 | 21.27 | 31.50 | 19.27 | 32.75 | 21.27 | 26.75 |
| T on W | | 23.50 | 26.75 | 23.50 | 26.75 | 21.50 | 32.75 | 19.50 | 23.50 |
| Hook Array on R | | 23.50 | 26.75 | 23.50 | 26.75 | 21.50 | 32.75 | 19.50 | 23.50 |

| | | Size: 8 | | Size: 4 | | Size: 1A | | Size: 3A | |
|---|---|---|---|---|---|---|---|---|---|
| | | Ctr of mass coordinates, Inches: | | | | | | | |
| | | x | y | x | y | x | y | x | y |
| Separated | 1 | 3.06 | 22.13 | 4.25 | 22.63 | 5.75 | 23.63 | 5.75 | 27.50 |
| Shapes per | 2 | 8.56 | 22.58 | 11.25 | 24.00 | 15.75 | 26.61 | 15.75 | 30.02 |
| FIG. 15-17 | 3 | 7.75 | 5.11 | 10.33 | 8.58 | 14.33 | 8.02 | 14.33 | 9.93 |
| | 4 | 7.75 | 39.74 | 10.33 | 39.01 | 14.33 | 43.21 | 14.33 | 46.42 |
| | 5 | 3.06 | 14.75 | 4.25 | 15.13 | 5.75 | 18.38 | 5.75 | 22.25 |
| | 6 | 8.56 | 18.34 | 11.25 | 21.31 | 15.75 | 24.14 | 15.75 | 29.45 |
| | 7 | 7.75 | 4.86 | 10.33 | 8.33 | 14.33 | 7.77 | 14.33 | 9.68 |
| | 8 | 4.00 | 14.75 | 6.88 | 15.13 | 9.75 | 18.38 | 9.56 | 22.25 |
| | 9 | 6.75 | 15.77 | 9.63 | 17.73 | 12.50 | 19.83 | 12.31 | 23.72 |
| | 10 | 6.50 | 1.44 | 9.25 | 3.55 | 12.17 | 2.02 | 12.04 | 2.05 |
| Tab R | | 15.25 | 26.75 | 18.25 | 27.50 | 24.25 | 27.00 | 24.25 | 31.75 |
| Patch T at edge | | 10.50 | 26.00 | 13.50 | 26.75 | 19.50 | 26.75 | 19.50 | 31.00 |
| Tab C | | 12.27 | 26.50 | 15.27 | 27.25 | 21.27 | 26.75 | 21.27 | 31.50 |
| T on W | | 14.50 | 26.50 | 17.50 | 27.25 | 23.50 | 26.75 | 23.50 | 26.75 |
| Hook Array on R | | 14.50 | 26.50 | 17.50 | 27.25 | 23.50 | 26.75 | 23.50 | 26.75 |

Continuing with Size 5 as the illustrate example, the x and y coordinates for the center of mass for the separated shapes are determined for the base. For the rectangular shape 1, positioned with a corner at the origin and aligned with one side along the bisecting axis of symmetry, the x and y coordinates lie at the center with respect to the origin, that is x=11.5/2, i.e. 5.75 and y=54.5/2, i.e. 27.25. For the triangle shape 3: the x coordinate is one-third of the leg having the dimension of 6.5 (=18−11.5) plus the 11.5 distance that the right angle is away from the origin, i.e. 13.667; the y coordinate is two-thirds the dimension of the other leg plus the off-set of Setback 1, i.e. 0.5+0.666666*10.817816=−7.71. For the triangular shape 4: the x coordinate is the same as that of triangle 3, i.e. 13.667, the y coordinate is the result of subtracting from the maximum length the appropriate off-set of Setback 2 and two-thirds the dimension of the leg perpendicular to the leg used to determine the x coordinate, i.e. 54.5−0.5−0.666666666*6.9730966=49.35. For the rectangular shape 2: the x coordinate is half the width of 18−11.5 plus the 11.5 distance that the side of the rectangle is closest to the origin, i.e. 14.75; the y coordinate is half of the distance between the two adjacent triangles, i.e. (54.5−0.5−0.5−10.817816−6.9703966)/2), plus the appropriate off-set of Setback 1 and the dimension of the leg of triangle 3 in the Y direction, i.e. 0.5+10.817816, which equals ~29.174.

The following are the x and y coordinate determinations for the separated shapes from the intermediate. For the rectangular shape 5, positioned with a corner at the origin and aligned with one side along the bisecting axis of symmetry, the x and y coordinates are the center with respect to the origin, that is x=11.5/2, i.e. 5.75 and y=35.75/2, i.e. 17.875. For the triangle shape 7: the x coordinate is one-third of the leg having the dimension of 6.5 (=18−11.5) plus the 11.5 distance that the right angle is away from the origin, i.e. 13.667; the y coordinate is two-thirds the dimension of the other leg plus the off-set of Setback 1, i.e. 0.5+0.666666*10.817816=−7.71. For the rectangular shape 6: the x coordinate is half the width of 18−11.5 plus the 11.5 distance that the side of the rectangle is closest to the origin, i.e. 14.75; the y coordinate is half of the distance above the adjacent triangle, i.e. 35.75−10.817816−0.5)/2, plus the appropriate off-set of Setback 1 and the dimension of the leg of triangle 7 in the Y direction, i.e. 0.5+10.817816, which equals ~23.534.

The following are the x and y coordinate determinations for the separated shapes from the reinforcement. For the rectangular shape 8, the corner farthest from the origin in the X direction is at a distance of 11.5 and the x coordinate is 11.5 less half of the 4.88 dimension, i.e. ~9.06; the y coordinate is half the dimension in the Y direction, i.e. 35.75/2=17.875. For the triangle shape 10: the x coordinate is one-third of the leg having the dimension of 5.5–4.88 plus the 11.5 distance in the X direction that the right angle is from the origin, i.e. 0.3333333*(5.5–4.88)=~11.707; the y coordinate is the offset of Setback 1 plus two-thirds of the dimension of the other leg, i.e. 0.25+0.66666661.03185336.5=~0.938. For the rectangular shape 9: the x coordinate is half the dimension of 5.5–4.88 plus the 11.5 distance that the closest side of the rectangle is to the origin, i.e. 11.5+((5.5-4.88)/2)=11.81; the y coordinate is half of the distance above the adjacent triangle, i.e. 35.75−1.0318533−0.25)/2, plus the appropriate off-set of Setback 1 and the dimension of the leg of triangle 10 in the Y direction, i.e. 1.0318533+0.25, which equals ~18.526.

The following are the x and y coordinate determinations for the rectangular side tab R as it is attached per FIG. 19 to the first or third edge of the barrier panel. As indicated for the example shown in FIG. 19, the edge of the tab in the Y direction that is farthest from the origin lies 1.5 inches from the pre-determined fold line in the direction of the first end of the barrier panel. This 1.5 inch distance from the pre-determined fold line happens to coincide with the first end of barrier panel for this particular example, but in other embodiments of the invention this 1.5 inch distance (for placement of the side tab relative to the pre-determined fold line) does not coincide with the first end of the barrier panel. The x coordinate is half the width dimension plus the distance that the side tab is away from the bisecting axis of symmetry, i.e. (8.5/2)+18=22.25; the y coordinate is determined by subtracting from the maximum length of the intermediate (the maximum dimension in the Y direction) one-half of the tab's length dimension, i.e. 35.75−(5.5/2)=33.

The following are the x and y coordinate determinations for the semicircular side tab C as it is attached per FIG. 19 to the first or third edge of the barrier panel. The edge of tab C that coincides with the diameter dimension lies adjacent the first or third edge of the barrier panel and the corner that is farthest from the origin aligns with the first end of the barrier panel. The x coordinate is the radius times the factor ($4/3\pi$) plus the distance that the side tab is away from the bisecting axis of symmetry, i.e. $3*(4/3\pi)+18=\sim19.273$; the y coordinate is determined by subtracting from the maximum length of the intermediate (the maximum dimension in the Y direction) one-half of the tab's length dimension, which is the diameter dimension, i.e. 35.75−(6/2)=32.75.

The following are the x and y coordinate determinations for the adhesive patch T on the side of the barrier panel as illustrated in FIG. 19. For the adhesive patch on the barrier panel with the farthest edge of the patch with respect to the bisecting axis of symmetry adjacent the first or third edge, the coordinate is one-half the width dimension of the patch subtracted from the maximum width dimension of intermediate, i.e. 18−(½)=17.5. When the position of the adhesive patch along the first or third edge gives a distance of 1.0 in the Y direction between the first end of the barrier panel and the nearest edge of the patch relative to the first end, the y coordinate is the maximum length dimension of the intermediate less the given distance less one-half the length dimension of the patch, i.e. 35.75−1.0−(4/2)=32.75.

The following are the x and y coordinate determinations for the hook array H on the rectangular side tab as shown in FIG. 19 or for the adhesive patch T in place of the hook array H. The side tab R is attached so that it has x and y coordinates as previously described. Since the dimensions of the patch T and the hook array H elements are the same, their respective x and y coordinates when placed in the same location on the tab R are the same. When either of these elements (adhesive patch T or hook array H) is placed on the tab R so that the edges of the tab R and the element that are nearest the bisecting axis of symmetry are a distance 3 apart, the x coordinate of the element is one-half the width dimension of the element plus the 3 distance plus the maximum width of the intermediate from the bisecting axis of symmetry, i.e. (½)+3+18=21.5. When the element is placed so that the farthest edges of the element and the tab R with respect to the origin are a distance 1 inch apart, the y coordinate of the element is the maximum length of the intermediate less the 1 inch distance apart less one-half the length dimension of the element, i.e. 35.75−1−(4/2).

The centers of mass for the separated shapes and components are next weight averaged by their mass contributions. For the given Size examples the weight averaging uses values from Tables A-B, i.e. from Tables A and B the mass values for each separated shape are calculated and Table C provides the x and y coordinates. Continuing with the Size 5 as the illustrative example, Table D lists the x and y coordinates for the separated centers of mass and their corresponding mass values for the 650, 550, and 450.

TABLE D

Size 5 example

| Shape regions in: | Separated Center of Mass Coordinates, inches | | m, oz. | | |
|---|---|---|---|---|---|
| | x | y | 650 | 550 | 450 |
| | | | for fabric Basis Weight Combinations per: | | |
| | | | 2.57 osy | 2.05 osy | 1.85 osy |
| Base | | | | | |
| 1 | 5.750 | 27.250 | 1.243 | 0.991 | 0.895 |
| 2 | 14.750 | 29.174 | 0.460 | 0.367 | 0.331 |
| 3 | 13.667 | 7.712 | 0.070 | 0.056 | 0.050 |
| 4 | 13.667 | 49.351 | 0.045 | 0.036 | 0.032 |
| | | Mass SUM | 1.818 | 1.450 | 1.309 |

TABLE D-continued

Size 5 example

| Shape regions in: | Separated Center of Mass Coordinates, inches | | m, oz. | | |
|---|---|---|---|---|---|
| | x | y | 650 | 550 | 450 |
| | | | for fabric basis weight of | | |
| | | | 1.85 osy | 1.4 osy | 1.2 osy |
| Intermediate | | | | | |
| 5 | 5.750 | 17.875 | 0.587 | 0.444 | 0.381 |
| 6 | 14.750 | 23.534 | 0.227 | 0.172 | 0.147 |
| 7 | 13.667 | 7.711 | 0.050 | 0.038 | 0.033 |
| | | | Mass SUM 0.864 | 0.654 | 0.560 |
| | | | for fabric basis weight of | | |
| | | | 2.57 osy | 2.57 osy | 1.85 osy |
| Reinforcement | | | | | |
| 8 | 9.060 | 17.875 | 0.346 | 0.346 | 0.249 |
| 9 | 11.810 | 18.516 | 0.042 | 0.042 | 0.031 |
| 10 | 11.707 | 0.938 | 0.001 | 0.001 | 0.000 |
| | | | Mass SUM 0.389 | 0.389 | 0.280 |
| | | | for fabric basis weight of | | |
| | | | 2.57 osy | 2.57 osy | 1.85 osy |
| Rectangular tab R per FIG. 19 | 22.25 | 33 | 0.093 | 0.093 | 0.067 |
| | | | for fabric basis weight of | | |
| | | | 2.57 osy | 2.57 osy | 2.57 osy |
| Semi-circular tab C per FIG. 19 | 19.274 | 32.75 | 0.028 | 0.028 | 0.028 |
| Adhesive patch T per FIG. 19 | 17.5 | 32.25 | 0.012 | 0.012 | 0.012 |
| Hook array H per FIG. 19 | 21.5 | 32.75 | 0.018 | 0.018 | 0.018 |
| Adhesive patch T in place of hook array H per FIG. 19 | 21.5 | 32.75 | 0.012 | 0.012 | 0.012 |

With the separated center of mass locations and mass contributions identified, the next step is to combine these values together to give the center of mass for the assembly portion plus additional components. The total center of mass of the assembly portion is calculated as the average of all the separated center of mass locations of interest weighted by their masses. Since the locations are expressed as x and y coordinates, the average weighting is calculated to yield a single x and a single y coordinate for the assembly portion plus additional components, namely $x_{cm}$ and $y_{cm}$, according to these following relationships:

$$x_{cm} = \frac{1}{M_{total}} \sum (m_i * x_i)$$

$$y_{cm} = \frac{1}{M_{total}} \sum (m_i * y_i)$$

where $M_{total}$ the total mass of the assembly portion and components, $m_i$ represents the mass for each separated shape, and $x_i$ and $y_i$ represent the x and y coordinates for the center of mass for each separated shape. Table E lists the x and y shape coordinates per Table C for Size 5, their calculated mass values per Tables A and B using the 650 basis weight combination of fabrics, their respective product calculations of $(m_i*x_i)$ and $(m_i*y_i)$, and their appropriate sums, and the subsequent determination of $x_{cm}$ and $y_{cm}$ values.

TABLE E

Size 5 example

Center of Mass Coordinates, inches

|  | Shape regions | x | y | m, oz. | $x_i*m_i$ | $y_i*m_i$ |
|---|---|---|---|---|---|---|
|  |  |  |  | for 2.57 osy |  |  |
| Base | 1 | 5.750 | 27.250 | 1.243 | 7.146 | 33.868 |
|  | 2 | 14.750 | 29.174 | 0.460 | 6.790 | 13.429 |
|  | 3 | 13.667 | 7.712 | 0.070 | 0.953 | 0.538 |
|  | 4 | 13.667 | 49.351 | 0.045 | 0.614 | 2.217 |
|  |  | Base Subtotals |  | 1.818 | 15.503 | 50.052 |
|  |  |  |  | for 1.85 osy |  |  |
| Intermediate | 5 | 5.750 | 17.875 | 0.587 | 3.374 | 10.490 |
|  | 6 | 14.750 | 23.534 | 0.227 | 3.344 | 5.335 |
|  | 7 | 13.667 | 7.711 | 0.050 | 0.686 | 0.387 |
|  |  | Intermediate Subtotals |  | 0.864 | 7.404 | 16.212 |
|  |  |  |  | for 2.57 osy |  |  |
| Reinforcement | 8 | 9.060 | 17.875 | 0.346 | 3.134 | 6.184 |
|  | 9 | 11.810 | 18.516 | 0.042 | 0.500 | 0.785 |
|  | 10 | 11.707 | 0.938 | 0.001 | 0.007 | 0.001 |
|  |  | Reinforcement Subtotals |  | 0.389 | 3.642 | 6.969 |
|  |  | Total of Subtotals |  | 3.071 | 26.549 | 73.233 |
| Adhesive patch T per FIG. 19 |  | 17.500 | 32.250 | 0.012 | 0.202 | 0.372 |
| Hook array H per FIG. 19 |  | 21.500 | 32.750 | 0.018 | 0.396 | 0.603 |
| Adhesive patch T in place of hook array H per FIG. 19 |  | 21.500 | 32.750 | 0.012 | 0.248 | 0.378 |
| Rectangular tab W at 2.57 osy per FIG. 19 |  | 22.250 | 33.000 | 0.093 | 2.063 | 3.059 |
| Semi-circular tab C at 2.57 osy per FIG. 19 |  | 19.274 | 32.750 | 0.028 | 0.540 | 0.918 |
| Assembly (from Total of Subtotals) |  | 8.647 | 23.850 | 3.071 | 26.549 | 73.233 |
| Assembly with: |  |  |  |  |  |  |
| Rectangular tab R per FIG. 19 |  | 9.045 | 24.119 | 3.163 | 28.612 | 76.066 |
| Adhesive patch T per FIG. E |  | 8.680 | 23.884 | 3.082 | 26.751 | 73.612 |
| Adhesive patch T per FIG. 19 and semi-circular tab C per FIG. 19 |  | 8.775 | 23.963 | 3.110 | 27.291 | 74.302 |
| Rectangular tab R and hook array H per FIG. 19 |  | 9.117 | 24.168 | 3.182 | 29.008 | 76.897 |
| Rectangular tab R and Adhesive patch T in place of hook array H per FIG. 19 |  | 9.090 | 24.150 | 3.175 | 28.860 | 76.671 |

Table F lists the $x_{cm}$ and $y_{cm}$ values for all of the Size examples at their basis weight combinations (250, 450, 55, and 650).

As Tables E and F show, adding components onto an assembly shifts the center of mass. These shifts are linked to unfolding behavior as has been noted and is further commented below. From Table F, the ranking impact of adding components from least to most is: adhesive patch T to each side of the barrier panel (least impact); the preceding patch T plus the semicircular tab C of 2.57 osy basis weight; rectangular Tab R with basis weights per respective Basis Weight Combination (per Table B); Tab R with patch at the side of the barrier panel; patch T on tab R; hook array H on tab R. Given the location and orientation of the added components, the shift in the x coordinate tends to be greater than in the y coordinate, but there are definitely shifts in both X and Y directions.

Some of the assemblies of the Size examples with only the adhesive patch T at the sides of the barrier panel (per FIG. 19) encountered inappropriate unfolding after wrapping around contents and steam sterilization. Addition of respective rectangular tabs R (per the indicated basis weight combinations of Table B) to the location as generally shown in FIG. 19 resulted in acceptable unfolding (aseptic opening) for all Size examples. However, some of these assemblies with adhesive patches T and with added semi-circular tabs C per FIG. 19 failed to always yield acceptable unfolding. The semi-circular tabs C have a diameter of 6 inches and consisted of 2 plies of 2.57 osy SMS fabric, which results in a weight of 0.028 ounce as noted in Table D; rectangular tabs R, with dimensions of 5.5 inches×8.5 inches and made from one ply of 2.57 osy SMS have weights of 0.093 ounce, are 3.3 times the weight of tabs C.

These findings indicate that a certain weight over a specific location exists for a given assembly to ensure aseptic opening, and that such a weight and location translate into a critical center of mass (for each assembly portion with an appropriate side tab). For the assemblies of the Size examples, these critical values are either the x and y coordinates with the patch T on the side of the barrier panel and with the respective rectangular tab R per FIG. 19 or between them and the adhesive patch T and semi-circular tab C. The following analysis determines a range for critical center of mass coordinates that account for different dimensions and weights of assemblies.

Figure 20A:
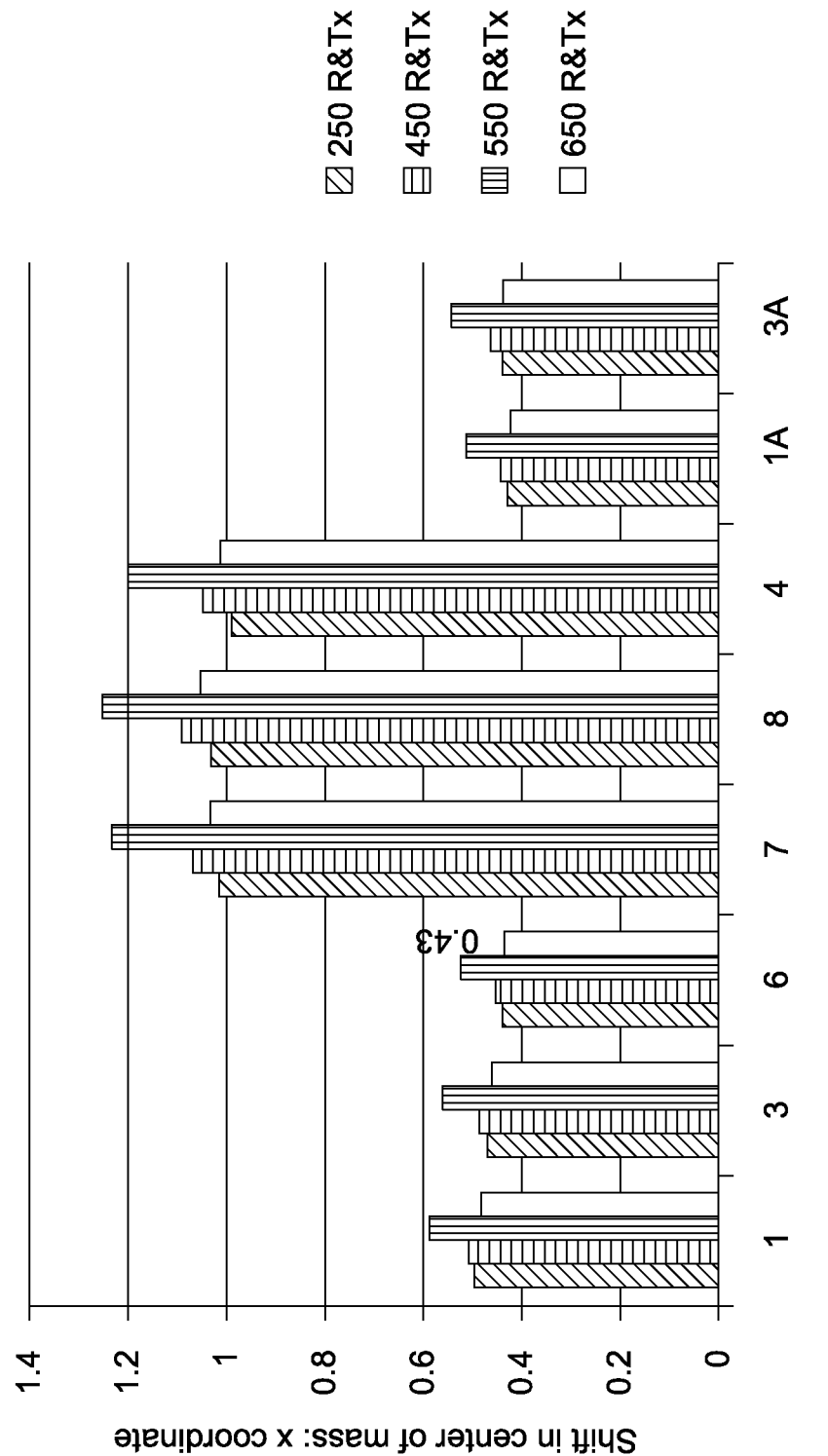
FIGS. 20A and 20B are illustrations of a graph of data showing the shifts in the centers of mass for examples of the invention and comparative examples.
Figure 20B:
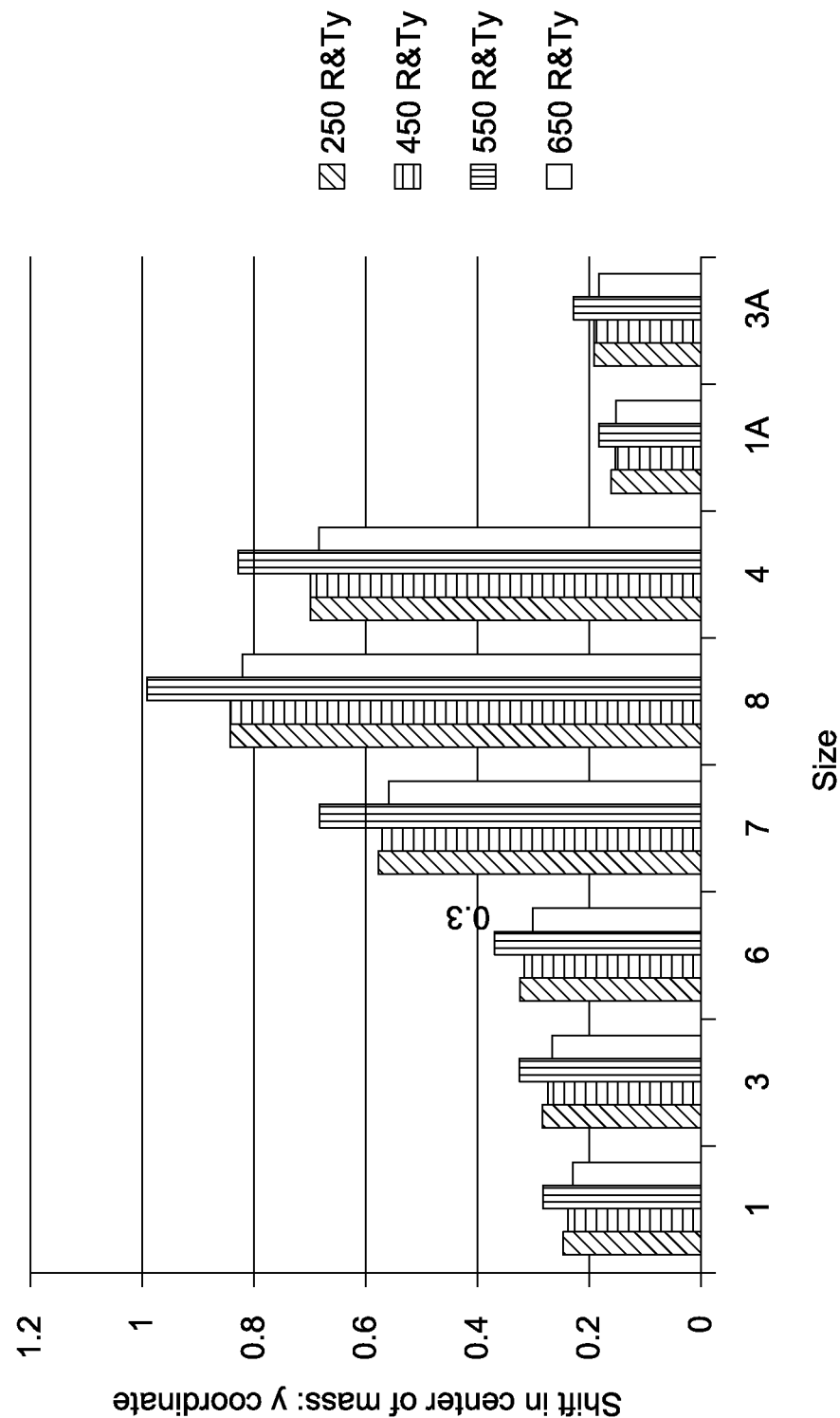
Figure 21A:
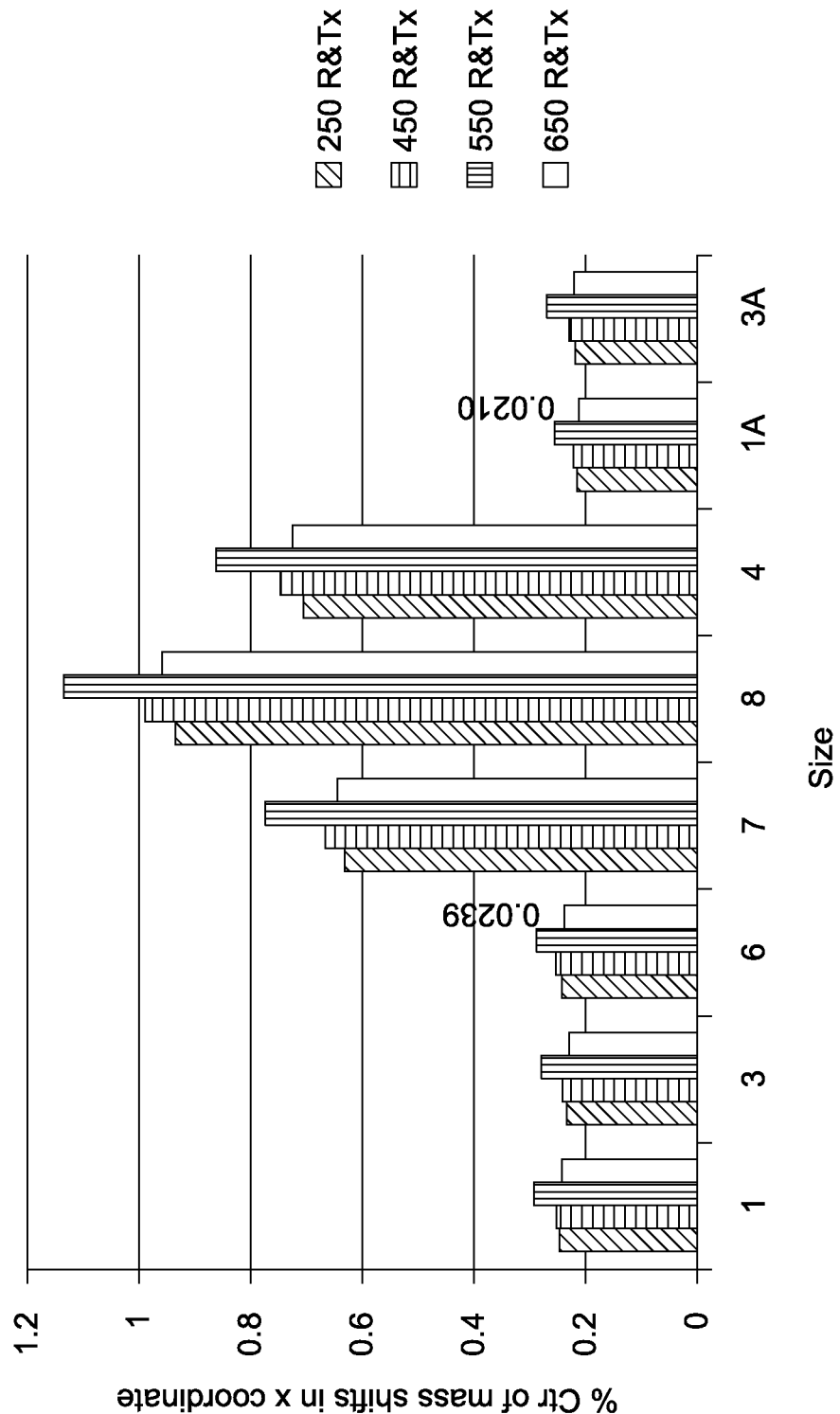
FIGS. 21A and 21B are illustrations of a graph of data showing the shifts in the centers of mass for examples of the invention and comparative examples.
Figure 21B:
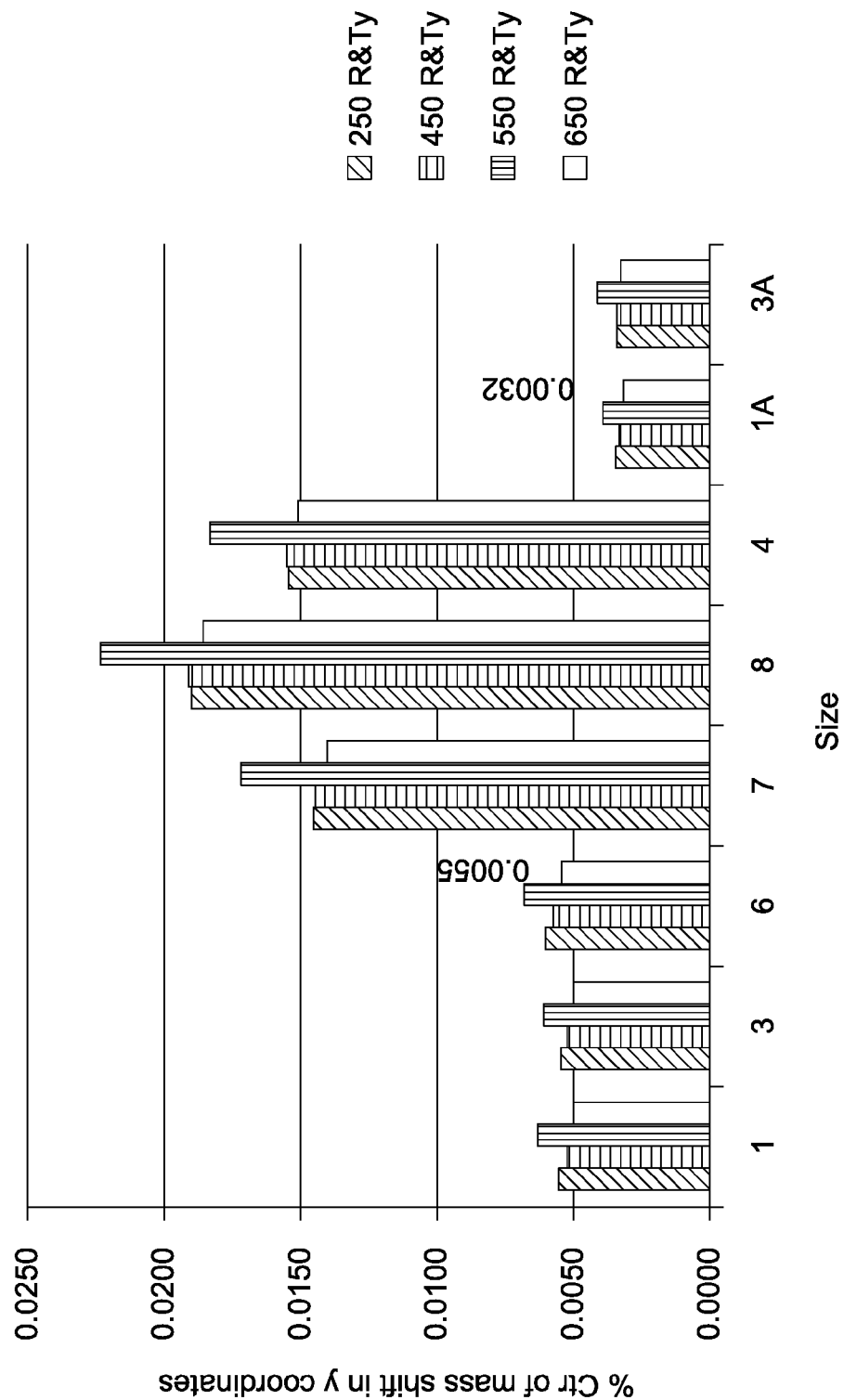
Figure 22A:
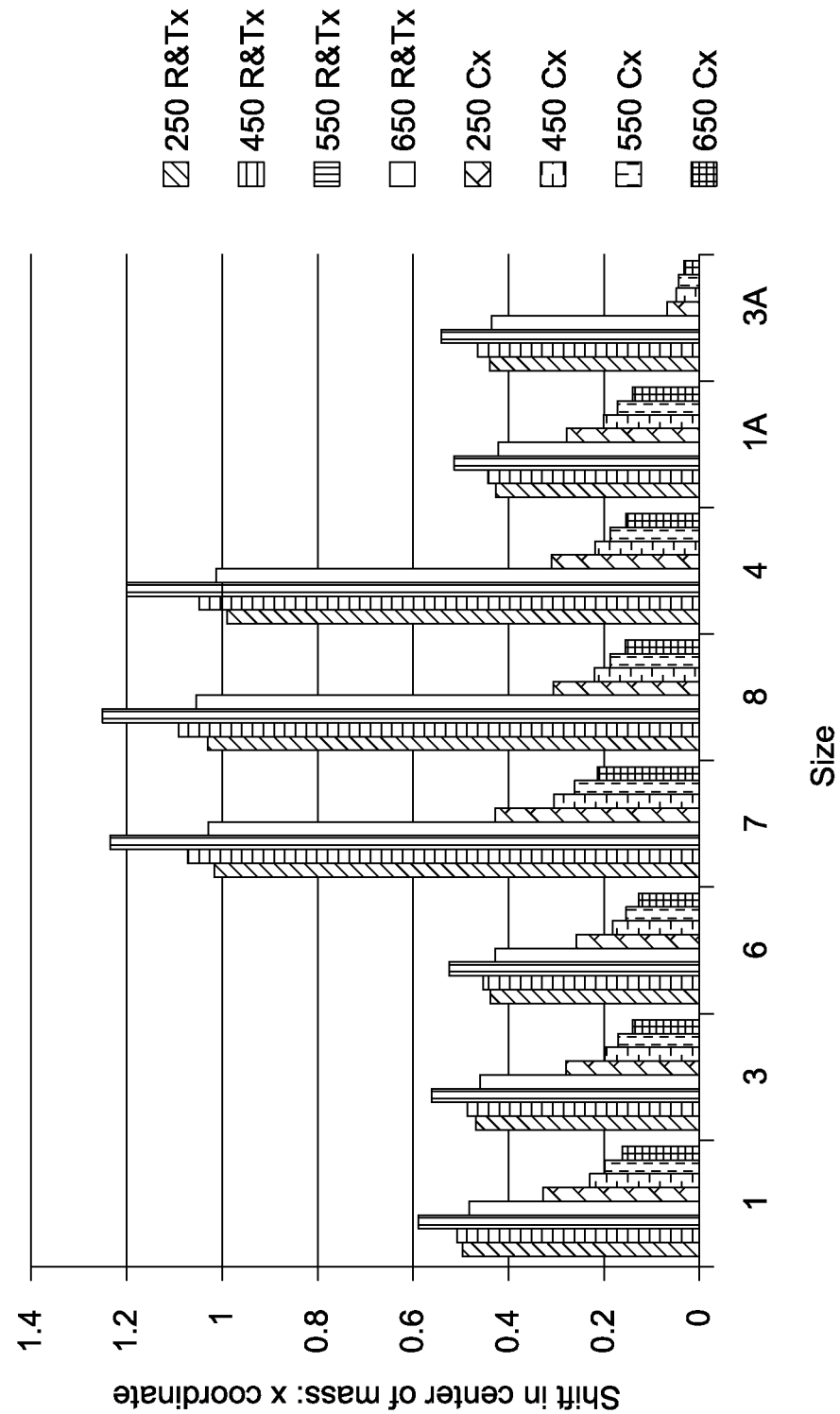
FIGS. 22A and 22B are illustrations of a graph of data showing the shifts in the centers of mass for examples of the invention and comparative examples.
Figure 22B:
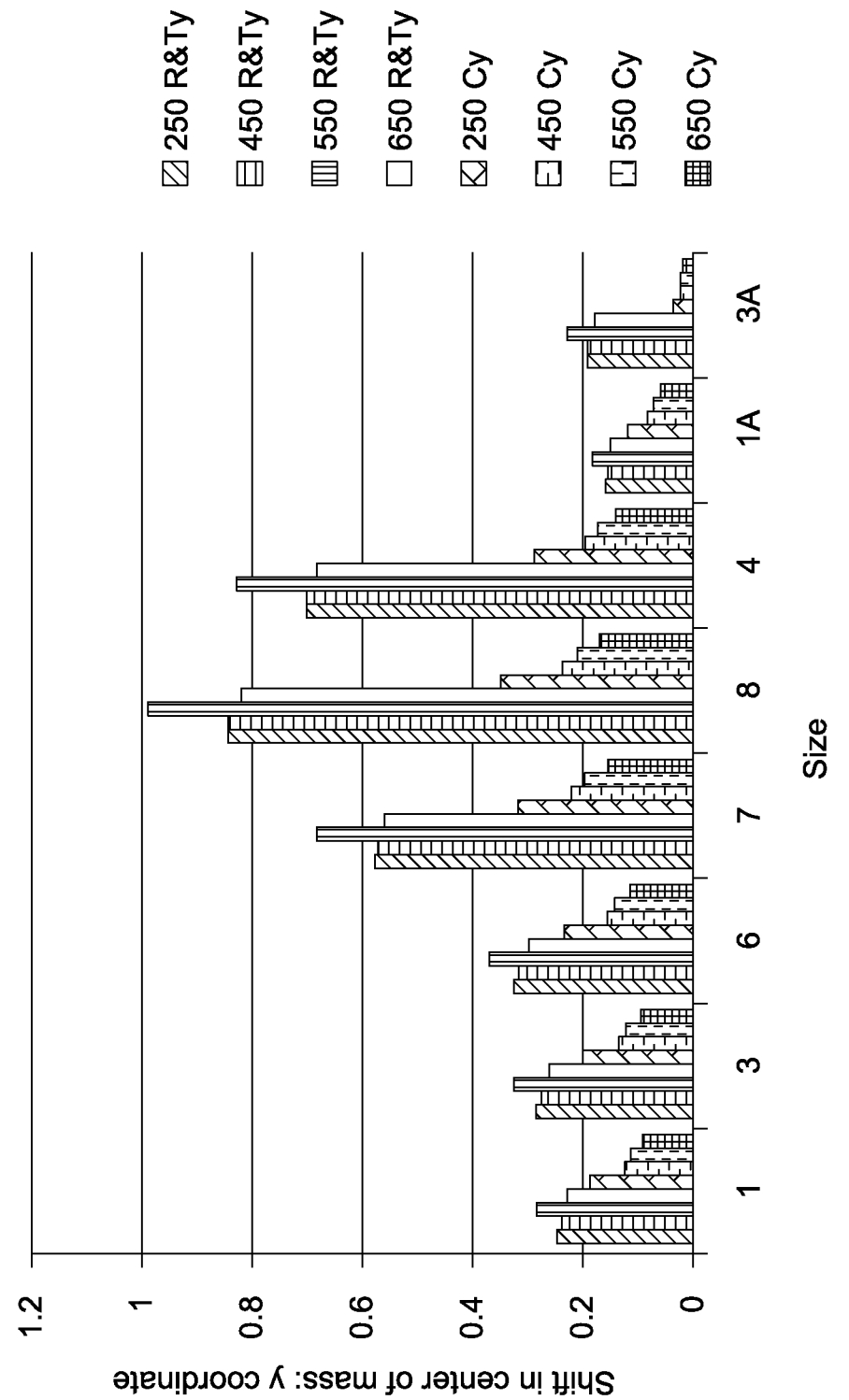
Figure 23A:
FIGS. 23A and 23B are illustrations of a graph of data showing the shifts in the centers of mass for examples of the invention and comparative examples.
Figure 23B:
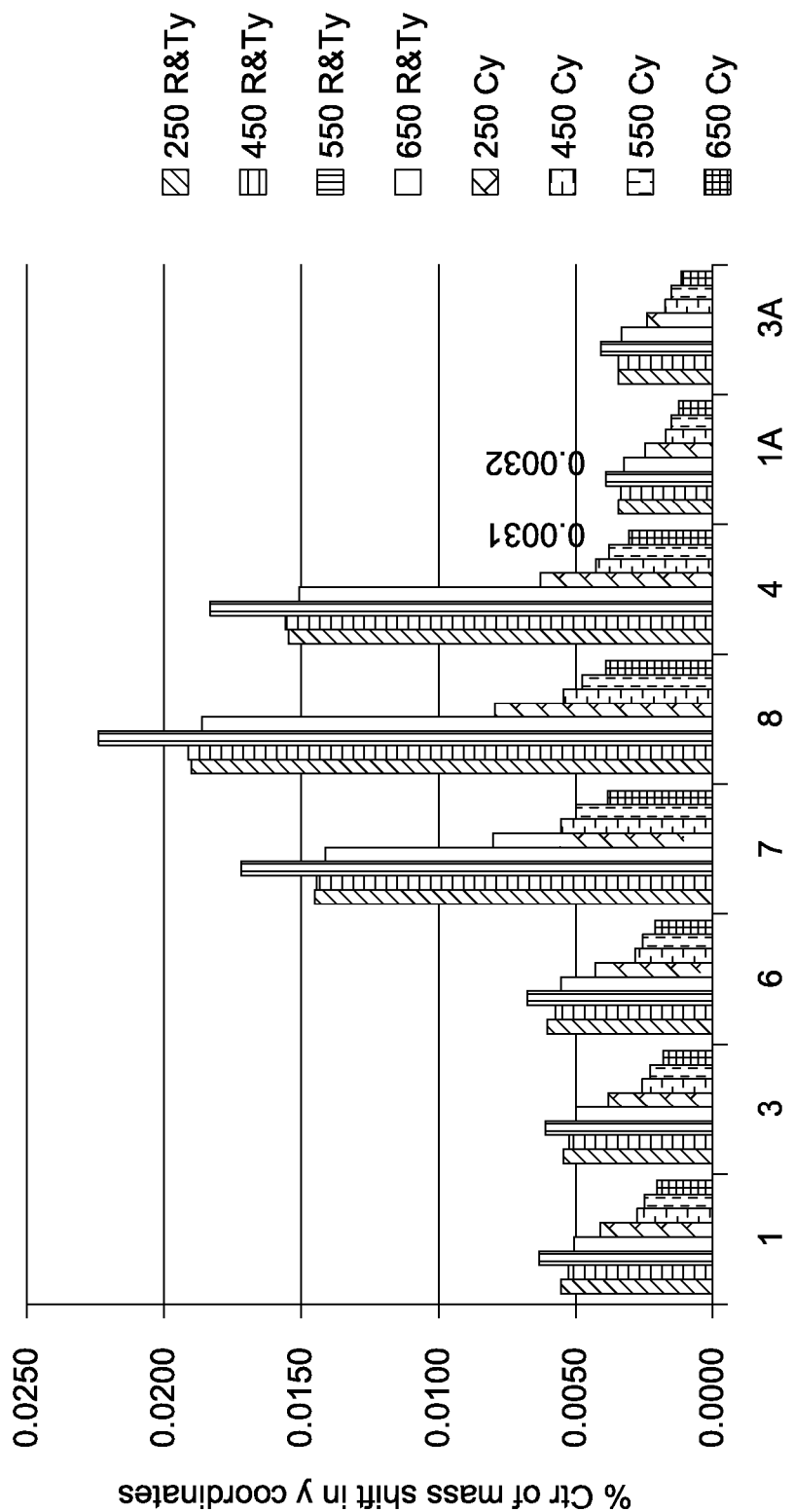

The differences or shifts in the centers of mass coordinates for the Size examples with adhesive patch T on the barrier panel sides (as indicated per FIG. 19) without and with their respective rectangular tabs R are shown in FIGS. 20A and 20B respectively (e.g. "250 R&Tx" and "250 R&Ty" indicate the shifts in the x and y coordinates at the 250 Basis Weight Combinations per Table B). To account for the different dimensions among the assemblies, as given in Table A, the respective x and y shifts are 'normalized' by their corresponding L and W dimensions of the Base. Such normalization is graphically shown in FIGS. 21A and 21B. Such normalization points out minimum % shifts among the Size examples, these minimums are for the Size 1A at the 650 Basis Weight Combination, i.e. % R&Tx=0.0210, % R&Ty=0.0032. All the other x and y coordinates with the respective rectangular tab R are believed to contribute excessive mass, and hence excessive weight beyond the side of the barrier panel than is needed to ensure aseptic opening. Note that the minimum normalized x value is different from the normalized y value.

Next, similar normalizations are done for the Size example assemblies with the semi-circular tab C with the adhesive patch T (as located per FIG. 19) and these are added to the previous Figures for comparison in FIGS. 22A, 22B, 23A and 23B. For FIGS. 22A, 22B, 23A and 23B, the "Cx" and "Cy" labeling corresponds to tab C with the patch T at the sides of the assemblies per FIG. 19). As evident, some normalized value for the semi-circular tab C (plus patch T) that is closest to being below or essentially the same as that for the minimum % values for the assemblies with adhesive patches T on their sides and rectangular tabs R further defines a range where the critical centers of mass lie that correspond to x and y coordinates for added components that ensure aseptic opening. The normalized values for the % Cx that are closest to the minimum % R&Tx value (for the rectangular tab R) is for the Size 8 at the 450 basis Weight Combination, i.e. 0.0200; the % Cy minimum closest to the % R&Ty minimum is for Size 4 at the 650 basis Weight Combination, i.e. 0.0031. Because these % Cx and % Cy minimums were for Size examples that were observed to open (unfold) acceptably, these are concluded to be the critical % shifts in center of mass needed to ensure aseptic opening.

From these concluded critical % shifts, corresponding critical x and y coordinate shifts that are needed for a given assembly portion with an added side tab component are determined via factoring in the W and L dimensions. Then these shifts are added to the respective x and y coordinates for the given assembly portion (without side tabs or other components) to yield final 'critical' center of mass coordinates (for the assembly portion plus any added components, e.g. side tabs and panel attachment means). Through selection of certain side tab dimensions and basis weights and for other added components, e.g. panel attachment means, the $x_{cm}$ and/or $y_{cm}$ average weighting relationships allow one to derive corresponding dimensions that produce the final critical centers of mass. In other words, from the known center of mass values (the assembly portion alone, the panel attachment means alone, and the critical coordinates) and the mass of the given assembly portion and the panel attachment means, the average weighting relationships are used to solve for the mass of the 'critical side tab'. Choosing a shape for the side tab and specifying certain parameters about weight distribution in the side tab results in identified dimensions, and hence weight. Such calculations are shown below using an assembly portion of Size 5 at the 650 Basis Weight Combination.

To solve for the critical side tab for Size 5, first the critical % shifts (0.0221 in the X direction; 0.0031 in the Y direction) are respectively multiplied by the intermediate L and W dimensions per Table A, i.e. 18, 54.5, to give critical shifts of 0.3978 for x coordinates and 0.16895 for y coordinates. Then these critical shifts are added respectively to known center of mass coordinates for the assembly portion alone or with panel attachment means directly on the barrier panel.

For the case when the assembly portion uses adhesive patch T as the panel attachment means and the patch T is on the side of the barrier panel (per FIG. 19), then from Table O: x=8.680 and y=23.884 is the appropriate known center of mass to which the critical shifts are added to give the final critical center of mass of: $x_{cm}$=9.0778, $y_{cm}$=24.05295. From Table E the mass of the assembly portion with the patch T is 3.0821. To simplify calculations, a rectangular side tab is chosen with an L dimension of 5.5 inches and placement that matches the y coordinate of Table E, i.e. 33; this allows use of the $y_{cm}$ average weighting relationship to solve for the mass of the critical side tab as follows:

$$24.05295 = \frac{23.884*3.0821 + 33*m}{3.0821 + m}$$

Solving for m yields 0.058199794 in terms of ounces. Choosing the critical side tab to be made from a material that matches the 650 Basis Weight Combination of Table B gives the material a basis weight of 2.57 osy. Thus, the W dimension of the rectangular tab for this assembly configuration (Patch T on sides of barrier panel) is determined as:

0.058199794/(2.57*5.5[0.0007716049327])= 5.336182079 inches where the bracketed term is the conversion factor for 1 square inch=0.0007716049327 square yard. This critical side tab has an area of ~30.4 square inches versus the 46.75 square inches for side tab R (which has a mass of 0.097395 ounces).

For the case when assembly portion uses adhesive patch T as the panel attachment means and the patch T is on the critical side tab at the location that matches the location of the rectangular side tab R, then appropriate known centers of mass are: for the assembly portion alone from Table F: $x_1$=8.646 and $y_1$=23.85; and for the patch T located the same as on side tab R rectangular tab from table N: $x_2$=21.5 and $y_2$=32.75. The critical shifts are added to the $x_1$ and $y_1$ coordinates (for the assembly portion alone) to give the final critical center of mass of: $x_{cm}$=9.0438, $y_{cm}$=24.01895. From Table E the mass of the assembly portion is 3.0705 and the patch T is 0.011538. To simplify calculations, a rectangular side tab is chosen with an L dimension of 5.5 inches and placement that matches the y coordinate of Table E, i.e. 33; this allows use of the $y_{cm}$ average weighting relationship to solve for the mass of the critical side tab as follows:

$$24.01895 = \frac{23.85*3.0705 + 33*m + 32.75*0.011538}{3.0705 + m + 0.011538}$$

Solving for m yields 0.046541 in terms of ounces. Choosing the critical side tab to be made from a material that matches the 650 Basis Weight Combination of Table B gives the material a basis weight of 2.57 osy. Thus, the W dimension of the rectangular tab for this assembly configuration (Patch T on sides of barrier panel) is determined as:

$$0.046541/(2.57*5.5[0.0007716049327])=4.26 \text{ inches}$$

where the bracketed term is the conversion factor for 1 square inch=0.0007716049327 square yard. This critical side tab has an area of ~23.4 square inches versus the 46.75 square inches for side tab R (which has a mass of 0.097395 ounces). Thus for this case (patch T on the critical side tab) there is a weight savings opportunity compared to having the patch T directly at the side of barrier panel.

For practicality reasons, the dimension of the side tab in the X direction must be no more than 8.5 inches. A dimension of 8.5 inches gives an appendage on the side of the assembly that lays relatively flat (without folding itself) when the sides of the assembly are folded over the contents to be wrapped. This maximum X direction dimension also ensures that a pair of such tabs on opposite sides of the barrier panel minimally interferes with each other when the sides of the assembly are folded over the contents to be wrapped.

TABLE F

| | Basis Wgt Combination: | | | | | | | |
|---|---|---|---|---|---|---|---|---|
| | 250 | | 450 | | 550 | | 650 | |
| | Ctr of mass, inches | | | | | | | |
| | x | y | x | y | x | y | x | y |
| Size 1 | | | | | | | | |
| Assembly portion | 9.439 | 20.032 | 9.448 | 20.418 | 9.482 | 20.209 | 9.445 | 20.289 |
| Assembly portion with: | | | | | | | | |
| Rectangular tab R | 9.855 | 20.232 | 9.901 | 20.624 | 10.022 | 20.463 | 9.886 | 20.494 |
| Adhesive patch at edge T | 9.525 | 20.089 | 9.509 | 20.456 | 9.535 | 20.244 | 9.488 | 20.316 |
| Semi-circular tab C & T at edge | 9.764 | 20.224 | 9.680 | 20.547 | 9.683 | 20.326 | 9.608 | 20.382 |
| T on R | 9.968 | 20.286 | 9.981 | 20.660 | 10.090 | 20.495 | 9.942 | 20.519 |
| Hook Array on R | 10.035 | 20.318 | 10.028 | 20.681 | 10.130 | 20.514 | 9.975 | 20.535 |
| Tab R & T at edge | 9.935 | 20.286 | 9.958 | 20.660 | 10.070 | 20.495 | 9.925 | 20.519 |
| Size 3 | | | | | | | | |
| Assembly portion | 9.360 | 23.124 | 9.366 | 23.550 | 9.393 | 23.305 | 9.364 | 23.408 |
| Assembly portion with: | | | | | | | | |
| Rectangular tab R | 9.761 | 23.357 | 9.802 | 23.791 | 9.913 | 23.600 | 9.789 | 23.646 |
| Adhesive patch at edge T | 9.434 | 23.182 | 9.418 | 23.589 | 9.439 | 23.339 | 9.401 | 23.436 |
| Semi-circular tab C & T at edge | 9.641 | 23.327 | 9.566 | 23.688 | 9.567 | 23.427 | 9.505 | 23.507 |
| T on R | 9.859 | 23.381 | 9.871 | 23.806 | 9.972 | 23.614 | 9.837 | 23.657 |
| Hook Array on R | 9.916 | 23.395 | 9.912 | 23.815 | 10.007 | 23.622 | 9.866 | 23.664 |
| Tab R & T at edge | 9.830 | 23.411 | 9.851 | 23.827 | 9.955 | 23.632 | 9.823 | 23.672 |
| Size 5 | | | | | | | | |
| Assembly portion | 8.642 | 23.560 | 8.649 | 23.996 | 8.670 | 23.735 | 8.646 | 23.850 |
| Assembly portion with: | | | | | | | | |
| Rectangular tab R | 9.019 | 23.821 | 9.058 | 24.267 | 9.157 | 24.067 | 9.045 | 24.118 |
| Adhesive patch at edge T | 8.709 | 23.629 | 8.696 | 24.042 | 8.711 | 23.777 | 8.680 | 23.884 |
| Semi-circular tab C & T at edge | 8.899 | 23.793 | 8.831 | 24.154 | 8.828 | 23.876 | 8.775 | 23.963 |

TABLE F-continued

| | Basis Wgt Combination: | | | | | | | |
|---|---|---|---|---|---|---|---|---|
| | 250 | | 450 | | 550 | | 650 | |
| | Ctr of mass, inches | | | | | | | |
| | x | y | x | y | x | y | x | y |
| T on R | 9.110 | 23.887 | 9.123 | 24.311 | 9.212 | 24.106 | 9.090 | 24.150 |
| Hook Array on R | 9.164 | 23.925 | 9.161 | 24.337 | 9.244 | 24.129 | 9.117 | 24.168 |
| Tab R & T at edge | 9.081 | 23.887 | 9.102 | 24.311 | 9.194 | 24.106 | 9.076 | 24.150 |
| Size 7 | | | | | | | | |
| Assembly portion | 7.999 | 17.014 | 8.017 | 17.326 | 8.068 | 17.140 | 8.011 | 17.222 |
| Assembly portion with: | | | | | | | | |
| Rectangular tab R | 8.947 | 17.536 | 9.042 | 17.864 | 9.269 | 17.791 | 9.011 | 17.755 |
| Adhesive patch at edge T | 8.082 | 17.081 | 8.075 | 17.370 | 8.119 | 17.183 | 8.052 | 17.254 |
| Semi-circular tab C & T at edge | 8.427 | 17.333 | 8.322 | 17.546 | 8.331 | 17.337 | 8.226 | 17.379 |
| T on R | 9.055 | 17.596 | 9.118 | 17.905 | 9.064 | 17.826 | 9.064 | 17.784 |
| Hook Array on R | 9.118 | 17.632 | 9.162 | 17.929 | 9.095 | 17.846 | 9.095 | 17.801 |
| Tab R & T at edge | 9.014 | 17.591 | 9.089 | 17.901 | 9.307 | 17.826 | 9.044 | 17.782 |
| Size 8 | | | | | | | | |
| Assembly portion | 5.111 | 18.825 | 5.097 | 19.112 | 5.075 | 18.870 | 5.101 | 19.017 |
| Assembly portion with: | | | | | | | | |
| Rectangular tab R | 6.086 | 19.588 | 6.148 | 19.903 | 6.295 | 19.814 | 6.127 | 19.799 |
| Adhesive patch at edge T | 5.186 | 18.926 | 5.150 | 19.180 | 5.121 | 18.929 | 5.139 | 19.065 |
| Semi-circular tab C & T at edge | 5.419 | 19.175 | 5.317 | 19.352 | 5.264 | 19.081 | 5.257 | 19.189 |
| T on R | 6.192 | 19.675 | 6.222 | 19.962 | 6.356 | 19.864 | 6.180 | 19.841 |
| Hook Array on R | 6.254 | 19.726 | 6.266 | 19.996 | 6.392 | 19.893 | 6.211 | 19.865 |
| Tab R & T at edge | 6.142 | 19.669 | 6.187 | 19.957 | 6.326 | 19.860 | 6.155 | 19.838 |
| Size 4 | | | | | | | | |
| Assembly portion | 6.686 | 19.622 | 6.699 | 19.938 | 6.745 | 19.720 | 6.694 | 19.833 |
| Assembly portion with: | | | | | | | | |
| Rectangular tab R | 7.616 | 20.256 | 7.703 | 20.596 | 7.915 | 20.511 | 7.674 | 20.483 |
| Adhesive patch at edge T | 6.764 | 19.705 | 6.754 | 19.993 | 6.792 | 19.769 | 6.733 | 19.872 |
| Semi-circular tab C & T at edge | 6.996 | 19.910 | 6.920 | 20.135 | 6.934 | 19.894 | 6.851 | 19.974 |
| T on R | 7.720 | 20.330 | 7.777 | 20.645 | 7.975 | 20.553 | 7.726 | 20.518 |
| Hook Array on R | 7.782 | 20.373 | 7.820 | 20.675 | 8.011 | 20.578 | 7.756 | 20.539 |
| Tab R & T at edge | 7.678 | 20.325 | 7.747 | 20.642 | 7.950 | 20.550 | 7.705 | 20.516 |

TABLE F-continued

| | Basis Wgt Combination: | | | | | | | |
|---|---|---|---|---|---|---|---|---|
| | 250 | | 450 | | 550 | | 650 | |
| | Ctr of mass, inches | | | | | | | |
| | x | y | x | y | x | y | x | y |
| Size 3A | | | | | | | | |
| Assembly portion | 9.450 | 25.594 | 9.448 | 25.809 | 9.479 | 25.664 | 9.448 | 25.736 |
| Assembly portion with: | | | | | | | | |
| Rectangular tab R | 9.824 | 25.749 | 9.864 | 25.976 | 9.980 | 25.871 | 9.850 | 25.900 |
| Adhesive patch at edge T | 9.519 | 25.631 | 9.498 | 25.834 | 9.522 | 25.688 | 9.483 | 25.755 |
| Semi-circular tab C & T at edge | 9.711 | 25.727 | 9.638 | 25.902 | 9.645 | 25.749 | 9.582 | 25.802 |
| T on R | 9.969 | 25.756 | 9.930 | 25.979 | 10.037 | 25.875 | 9.896 | 25.902 |
| Hook Array on R | 9.915 | 25.760 | 9.969 | 25.982 | 10.071 | 25.877 | 9.923 | 25.904 |
| Tab R & T at edge | 9.890 | 25.785 | 9.912 | 26.001 | 10.022 | 25.894 | 9.884 | 25.917 |
| Size 1A | | | | | | | | |
| Assembly portion | 9.556 | 21.835 | 9.564 | 22.082 | 9.599 | 21.941 | 9.562 | 21.999 |
| Assembly portion with: | | | | | | | | |
| Rectangular tab R | 9.918 | 21.965 | 9.962 | 22.218 | 10.070 | 22.107 | 9.947 | 22.134 |
| Adhesive patch at edge T | 9.631 | 21.868 | 9.617 | 22.104 | 9.644 | 21.960 | 9.599 | 22.015 |
| Semi-circular tab C & T at edge | 9.837 | 21.955 | 9.767 | 22.164 | 9.773 | 22.013 | 9.704 | 22.058 |
| T on R | 10.016 | 22.000 | 10.032 | 22.242 | 10.130 | 22.128 | 9.996 | 22.150 |
| Hook Array on R | 10.075 | 22.020 | 10.074 | 22.256 | 10.165 | 22.140 | 10.025 | 22.160 |
| Tab R & T at edge | 9.987 | 21.996 | 10.011 | 22.239 | 10.112 | 22.126 | 9.983 | 22.149 |

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description. The figures are not drawn to scale and related elements may be omitted so as to emphasize the novel features of the invention. Structural and functional details depicted in the figures are provided for the purpose of teaching the practice of the invention to those skilled in the art and are not intended to be considered limitations. Directional terms such as left, right, front or rear are provided to assist in the understanding of the invention and are not intended to be considered as limitations.

While particular embodiments of the present invention have been described herein; it will be apparent to those skilled in the art that alterations and modifications may be made to the described embodiments without departing from the scope of the appended claims.

What is claimed is:

1. A flexible multi-panel sterilization assembly comprising:
   a barrier panel comprising a nonwoven permeable sheet material having barrier properties and susceptible to heat set during sterilization, the barrier panel including:
      a first surface and a second opposing surface,
      a first end and a second end opposite the first end,
      a first edge and a third edge, each such edge being generally perpendicular to the first end, and
      a second edge that is generally opposite the first end;
   side tabs located between the first end and the midpoint of the barrier panel and at or near the first edge and the third edge, the side tabs including grip portions for folding or unfolding the barrier panel, wherein each side tab has a weight greater than 0.028 ounces;
   a longitudinal axis extending from at least the first end to the second end of the barrier panel such that it bisects the assembly into a first assembly portion and a substantially equal second assembly portion; and
   a fold protection panel in juxtaposed communication with the barrier panel, the fold protection panel comprising a permeable sheet material, the fold protection panel including:
      a proximal end generally adjacent the first end of the barrier panel, a distal end generally opposite the proximal end, and
at least a first edge and a second edge extending away from the proximal end, the fold protection panel having a maximum width that is the greatest distance from the first edge to the second edge and a maximum length that is the distance from the proximal end to the distal end, such that:
after the barrier panel has been folded so the barrier panel's second end is brought towards its first end and the side tab on the first edge and the side tab on the third edge are folded over the barrier panel towards or overlapping each other to form at least a partial enclosure, the distal end of the fold protection panel is configured to cover at least the first edge and the third edge of the folded barrier panel;
wherein the first assembly portion extends from the longitudinal axis to include the first edge of the barrier panel and the side tab and defines a respective center of mass, and the second assembly portion extends from the longitudinal axis to include the third edge of the barrier panel and the side tab and defines a second respective center of mass, whereby the center of mass of the first assembly portion is closer to the first edge than to the longitudinal axis and the center of mass of the second assembly portion is closer to the third edge than to the longitudinal axis, wherein the side tabs shift the center of mass of the first assembly portion and the second second assembly portion.

2. The assembly of claim 1, wherein the side tabs contribute to the respective centers of mass in a manner that ensures aseptic opening after the assembly is wrapped around contents to be sterilized.

3. The assembly of claim 1, wherein the side tabs prevent the first and third edges of the barrier panel from folding back on itself during unfolding of the barrier panel after steam or heat sterilization.

4. The assembly of claim 1, wherein the side tabs provide weight beyond the side edges of the assembly and also towards the first end of the barrier panel that is adjacent the proximal end of the fold protection panel.

5. The assembly of claim 1, wherein the side tabs position the centers of mass for each assembly portion by at least a pre-determined distance away from the longitudinal axis and at least a pre-determined distance in the direction towards the first end.

6. The assembly of claim 1, wherein the barrier panel has a maximum width that is the distance from the first edge to the third edge and a maximum length that is the distance from the first end to the second end, the barrier panel also has a midpoint along the length and extending between the first edge and the third edge to generally delineate the barrier panel into a content receiving region extending from approximately the first end to the midpoint and a content covering region extending from the midpoint to approximately the second end; and further wherein the side tabs adjacent the barrier panels have a part of each side tab within the upper boundary of the content receiving region.

7. The assembly of claim 1, wherein each side tab further comprises panel attachment means.

8. A flexible multi-panel sterilization assembly comprising:
a barrier panel comprising a sheet of nonwoven barrier material susceptible to heat set during sterilization, the sheet defining at least one panel edge, the barrier panel configured to fold into side portions and an end portion to form a package around content to be sterilized;
side tabs extending diametrically from a portion of the barrier panel for sequentially positioning the side portions of the barrier panel in a folded configuration over the end portion and around content to be sterilized, and providing grips for simultaneously unfolding the folded side portions of the barrier panel; and
a fold protection panel extending from the barrier panel, the fold protection panel including;
a proximal end generally adjacent the barrier panel,
a distal end generally opposite the proximal end, and
wherein the distal end of the fold protection panel covers the one or more panel edges of the barrier panel after folding the side and end portions of the barrier panel;
a longitudinal axis extending from at least the first end to the second end of the barrier panel such that it bisects the assembly into a first assembly portion and a substantially equal second assembly portion;
wherein the first assembly portion extends from the longitudinal axis to include the first edge of the barrier panel and the side tab and defines a respective center of mass, and the second assembly portion extends from the longitudinal axis to include the third edge of the barrier panel and the side tab and defines a second respective center of mass, whereby the center of mass of the first assembly portion is closer to the first edge than to the longitudinal axis and the center of mass of the second assembly portion is closer to the third edge than to the longitudinal axis, wherein each of the side tabs provides weight in excess of 0.028 ounces beyond the side edges of the assembly and also towards the first the barrier panel that is adjacent the proximal end of the fold protection panel, wherein the side tabs shift the center of mass of the first assembly portion and the second assembly portion.

9. The assembly of claim 8, wherein the side tabs contribute to the respective centers of mass in a manner that ensures aseptic opening after the assembly is wrapped around contents to be sterilized.

10. The assembly of claim 8, wherein the side tabs prevent the first and third edges of the barrier panel from folding back on itself during unfolding of the barrier panel after steam or heat sterilization.

11. The assembly of claim 8, wherein each side tab further comprises panel attachment means.

12. A flexible multi-panel sterilization assembly comprising:
a barrier panel comprising a nonwoven permeable sheet material having barrier properties and susceptible to heat set during sterilization, the barrier panel including:
a first surface and a second opposing surface,
a first end and a second end opposite the first end,
a first edge and a third edge, each such edge being generally perpendicular to the first end, and
a second edge that is generally opposite the first end,
the barrier panel having a maximum width that is the distance from the first edge to the third edge and a maximum length that is the distance from the first end to the second end, the barrier panel having a midpoint along the length and extending between the first edge and the third edge to generally delineate the barrier panel into a content receiving region extending from approximately the first end to the midpoint and a content covering region extending from the midpoint to approximately the second end;
side tabs located between the first end and the midpoint of the barrier panel and at or near the first edge and the third edge; the side tabs including grip portions for folding or unfolding the barrier panel, wherein each side tab has a weight greater than 0.028 ounces; and a fold protection panel in juxtaposed communication with the barrier panel, the fold protection panel comprising a permeable sheet material, the fold protection panel including:
- a proximal end generally adjacent the first end of the barrier panel,
- a distal end generally opposite the proximal end, and
- at least a first edge and a second edge extending away from the proximal end, the fold protection panel having a maximum width that is the greatest distance from the first edge to the second edge and a maximum length that is the distance from the proximal end to the distal end, such that:
  - after the barrier panel has been folded at or near the barrier panel's midpoint so the barrier panel's second end is brought towards its first end and the side tab on the first edge and the side tab on the third edge are folded over the barrier panel towards or overlapping each other to form at least a partial enclosure, the distal end of the fold protection panel is configured to cover at least the first edge and the third edge of the folded barrier panel, wherein the assembly has a longitudinal axis extending from at least the first end to the second end of the barrier panel such that it bisects the assembly into a first assembly portion that includes a side tab and the first edge of the barrier panel and a second assembly portion that includes a side tab and the third edge of the barrier panel, the assembly portions being substantially equal, whereby the center of mass of the first assembly portion is closer to the first edge than to the longitudinal axis and the center of mass of the second assembly portion is closer to the third edge than to the longitudinal axis, wherein the side tabs shift the center of mass of the first assembly portion and the second assembly portion.

13. The assembly of claim 12, wherein the side tabs contribute to the respective centers of mass in a manner that ensures aseptic opening after the assembly is wrapped around contents to be sterilized.

14. The assembly of claim 12, wherein the side tabs prevent the first and third edges of the barrier panel from folding back on itself during unfolding of the barrier panel after steam or heat sterilization.

15. The assembly of claim 13, wherein the side tabs adjacent the barrier panels have a part of each side tab within the upper boundary of the content receiving region.

16. The assembly of claim 12, wherein each side tab further comprises panel attachment means.

17. The assembly of claim 1, wherein each side tab has a weight greater than 0.028 ounces up to about 3 ounces.

18. The assembly of claim 8, wherein each of the side tabs provides weight in excess of 0.028 ounces up to about 3 ounces beyond the side edges of the assembly and also towards the first end of the barrier panel that is adjacent the proximal end of the fold protection panel.

19. The assembly of claim 12, wherein each side tab has a weight greater than 0.028 ounces up to about 3 ounces.

* * * * *